US011344515B2

(12) United States Patent
Chretien et al.

(10) Patent No.: US 11,344,515 B2
(45) Date of Patent: *May 31, 2022

(54) 5-HYDROXYTRYPTAMINE 1B RECEPTOR-STIMULATING AGENT FOR USE AS A PROMOTER OF SATELLITE CELLS SELF-RENEWAL AND/OR DIFFERENTIATION

(71) Applicants: INSTITUT PASTEUR, Paris (FR); UNIVERSITE PARIS DESCARTES, Paris (FR); CENTRE HOSPITALIER SAINTE ANNE PARIS, Paris (FR); INSTITUT GUSTAVE-ROUSSY, Villejuif (FR)

(72) Inventors: Fabrice Bruno Chretien, Paris (FR); Raphael Gaillard, Paris (FR); Pierre Rocheteau, Paris (FR); Olivier Mir, Paris (FR)

(73) Assignees: INSTITUT PASTEUR, Paris (FR); UNIVERSITE PARIS DESCARTES, Paris (FR); CENTRE HOSPITALIER SAINTE ANNE PARIS, Paris (FR); INISTITI IT GI ISTAV/E Dm ICCV, Paris (FR)

(*) Notice: Subject to any disclaimer, the term of this patent is extended or adjusted under 35 U.S.C. 154(b) by 111 days.

This patent is subject to a terminal disclaimer.

(21) Appl. No.: 16/669,626

(22) Filed: Oct. 31, 2019

(65) Prior Publication Data

US 2020/0060999 A1    Feb. 27, 2020

Related U.S. Application Data

(63) Continuation of application No. 15/744,345, filed as application No. PCT/EP2016/066948 on Jul. 15, 2016, now Pat. No. 10,493,046.

(60) Provisional application No. 62/193,714, filed on Jul. 17, 2015.

(30) Foreign Application Priority Data

Apr. 15, 2016 (EP) ................................. 16305444

(51) Int. Cl.
| *A61K 31/138* | (2006.01) |
| *A61K 31/495* | (2006.01) |
| *A61P 21/00* | (2006.01) |
| *A61K 31/496* | (2006.01) |
| *A61K 45/06* | (2006.01) |
| *C12N 5/077* | (2010.01) |
| *G01N 33/50* | (2006.01) |

(52) U.S. Cl.
CPC .......... *A61K 31/138* (2013.01); *A61K 31/495* (2013.01); *A61K 31/496* (2013.01); *A61K 45/06* (2013.01); *A61P 21/00* (2018.01); *C12N 5/0659* (2013.01); *G01N 33/5061* (2013.01); *C12N 2501/999* (2013.01)

(58) Field of Classification Search
CPC .... A61K 31/138; A61K 31/495; A61K 45/06; C12N 2501/999
See application file for complete search history.

(56) References Cited

U.S. PATENT DOCUMENTS

| 9,562,024 | B2 | 2/2017 | Song et al. | |
| 10,493,046 | B2 * | 12/2019 | Chretien | ............... A61K 31/496 |
| 2014/0121256 | A1 | 5/2014 | McMichael | |
| 2016/0200698 | A1 | 7/2016 | Song et al. | |

FOREIGN PATENT DOCUMENTS

| WO | 03/029232 A1 | 4/2003 |
| WO | 2007/148341 A2 | 12/2007 |
| WO | 2008/078353 A1 | 7/2008 |
| WO | 2010/125348 A1 | 11/2010 |
| WO | 2012/174537 A2 | 12/2012 |
| WO | 2013/076245 A1 | 5/2013 |
| WO | 2017/063771 A1 | 4/2014 |
| WO | 2014/190063 A1 | 11/2014 |
| WO | 2015/035802 A1 | 3/2015 |
| WO | 2017/013031 A1 | 1/2017 |
| WO | 2017/084774 A1 | 5/2017 |
| WO | 2018/011382 A1 | 1/2018 |

OTHER PUBLICATIONS

Pauwels, 1994, "The 5-HT1D Receptor antagonist GR127,935 is an agonist at Cloned Human 5-HT1Da Receptor Sites," Neuropharmacology, vol. 34, No. 2, pp. 235-237 (1995).
Sauer, 2003, "Effect of antidepressants and their relative affinity for the Serotonin Transporter on the Risk of Myocardial Infarction.," Circulation, vol. 108, pp. 32-36.
Jiang, 2004, "Should SSRI be prescribed to all Patients with Ischemic Heart Disease?" Current Psychiatry Reports, urrent Science, vol. 6, pp. 202-209.
Malick, 2014, "Desvenlafaxine reduces apoptosis in amygdala after myocardial infarction," Brain Research Bulletin, vol. 109, pp. 158-163.
Droggrell, 2003, "The role of 5-HT on the cardiovascular and renal systems and the clinical potential of 5-HT modulation," Expert Opin. INvestig. Drugs, vol. 12, pp. 805-823.
Husamettin, 2002, "Amplification of sumatriptan-induced contractions with phenylephrine, histamine and KCI in the isolated human mesenteric artery: in vitro evidence for sumatriptan-induced mesenteric ischaemia," Naunyn-Schmiedeberg's Arch Pharmacol, vol. 366, pp. 254-261.

(Continued)

*Primary Examiner* — Olga N Chernyshev
(74) *Attorney, Agent, or Firm* — Arrigo, Lee, Guttman & Mouta-Bellum LLP

(57) ABSTRACT

The present invention relates to the field of muscle regeneration, and more particularly to the replenishment of the in vivo muscle stem cells pool. It more specifically relates to a 5-hydroxytryptamine B1 receptor-stimulating agent, and to a composition comprising said agent, for use as i) a promoter of satellite cells self-renewal and/or differentiation, and/or ii) an agent preventing and/or inhibiting the satellite cells pool exhaustion. The invention further encompasses therapeutic and screening methods.

27 Claims, 51 Drawing Sheets

(56) References Cited

OTHER PUBLICATIONS

Malinin, 2003, "Treatment with selective serotonin reuptake inhibitors for enhancing wound healing," Medical Hypotheses, vol. 63, pp. 103-109.
Nguyen, {Abstract} 2016, "Serotonin as a potential therapeutic target for mesenchymal stem cell—Mediated mprovement of wound healing," Journal of Investigative Dermatology, S133.
Villamil-Hernandez et al., Pharmacological evidence that 5-HT1A/1B/1D, α2-adrenoceptors and D2-like receptors mediate ergotamine-induced inhibition of the vasopressor sympathetic outflow in pithed rats, European Journal of Pharmacology 740 (2014), 512-521.
Tfelt-Hansen et al., Triptans in Migraine—A Comparative Review of Pharmacology, Pharmacokinetics and Efficacy, Drugs Dec. 2000; 60 (6): 1259-1287.
Sanchez et al., Vortioxetine, a novel antidepressant with multimodal activity: Review of preclinical and clinical data, Pharmacology & Therapeutics 145 (2015) 43-57.

\* cited by examiner

Number of vessels (CD31) in matrigel plugs after fluoxetine treatment

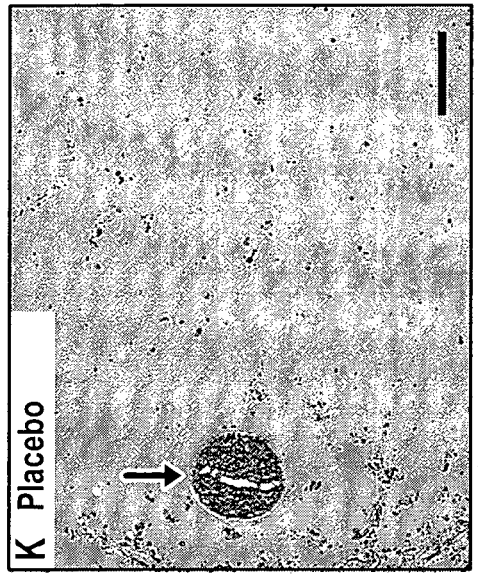
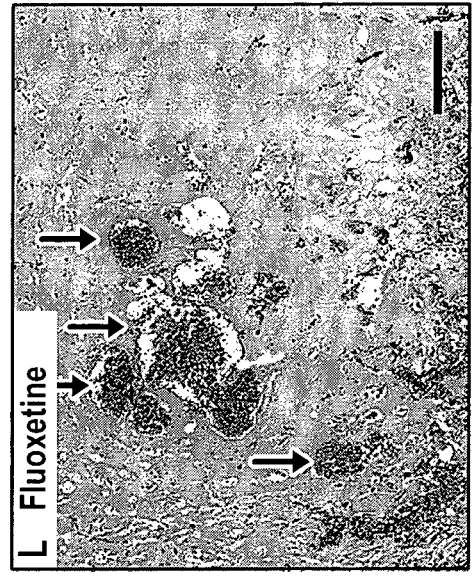
FIG. 2 (continued)
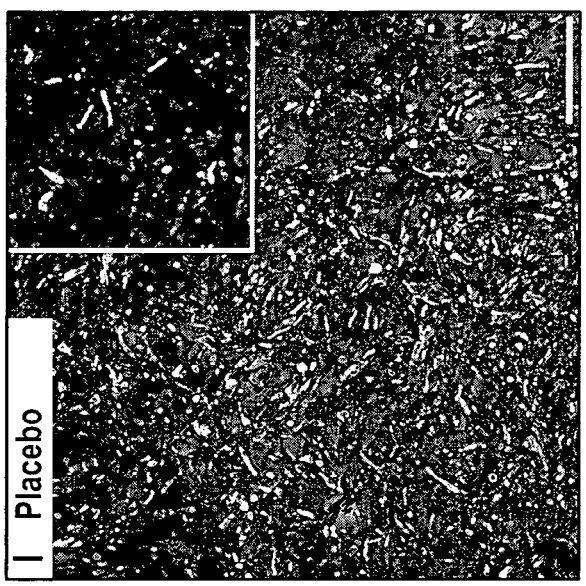
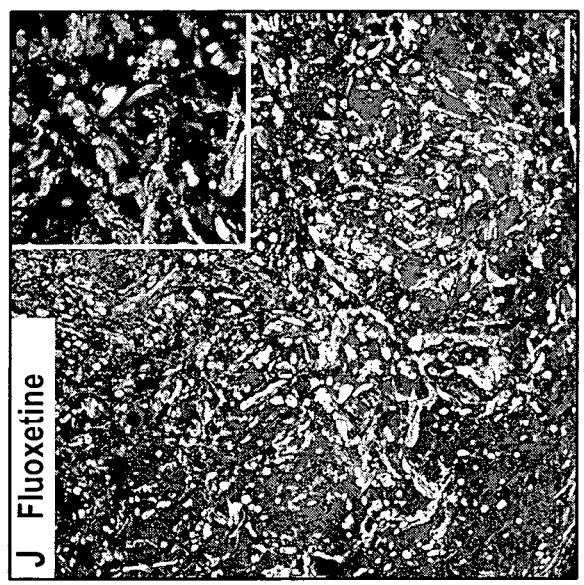

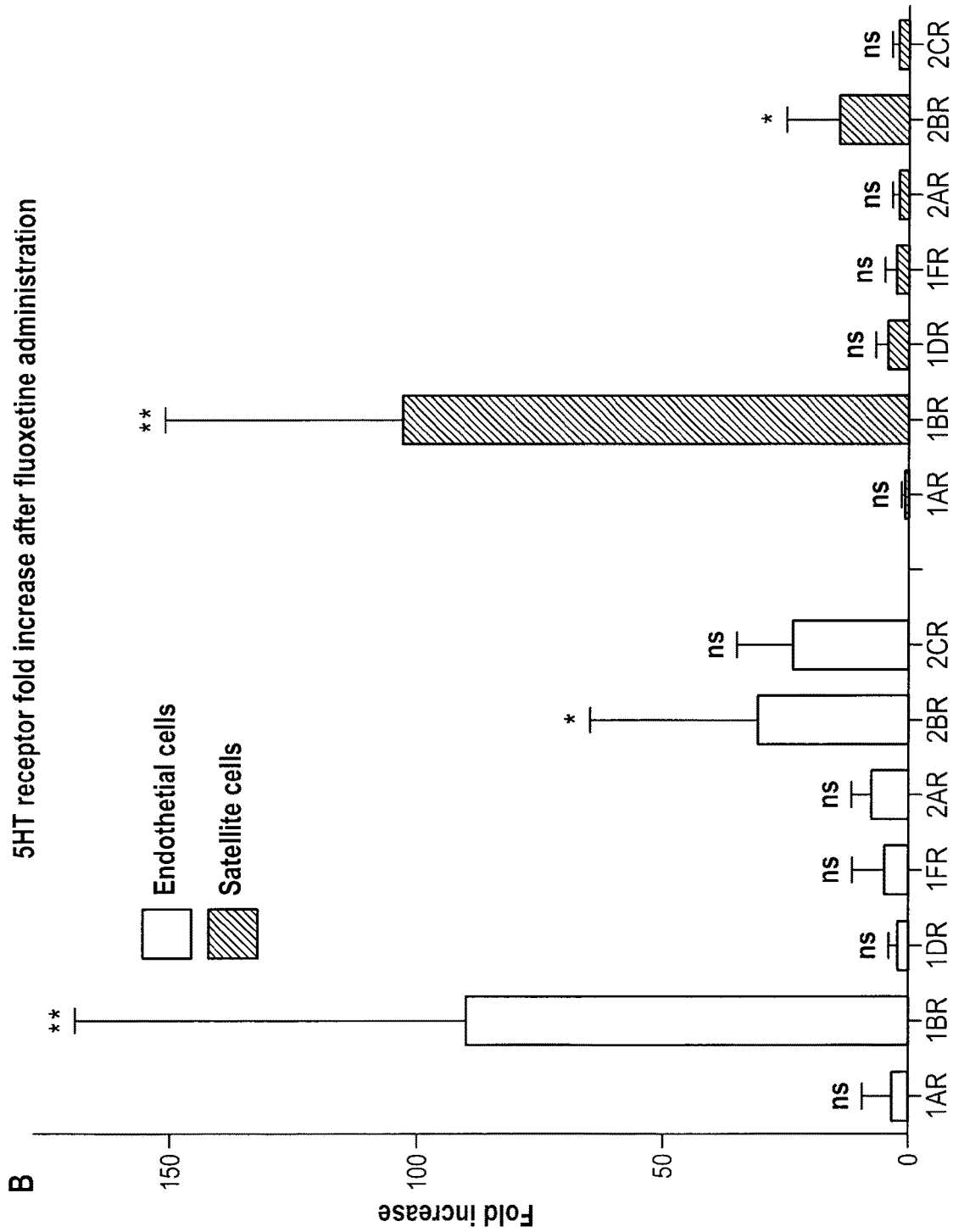

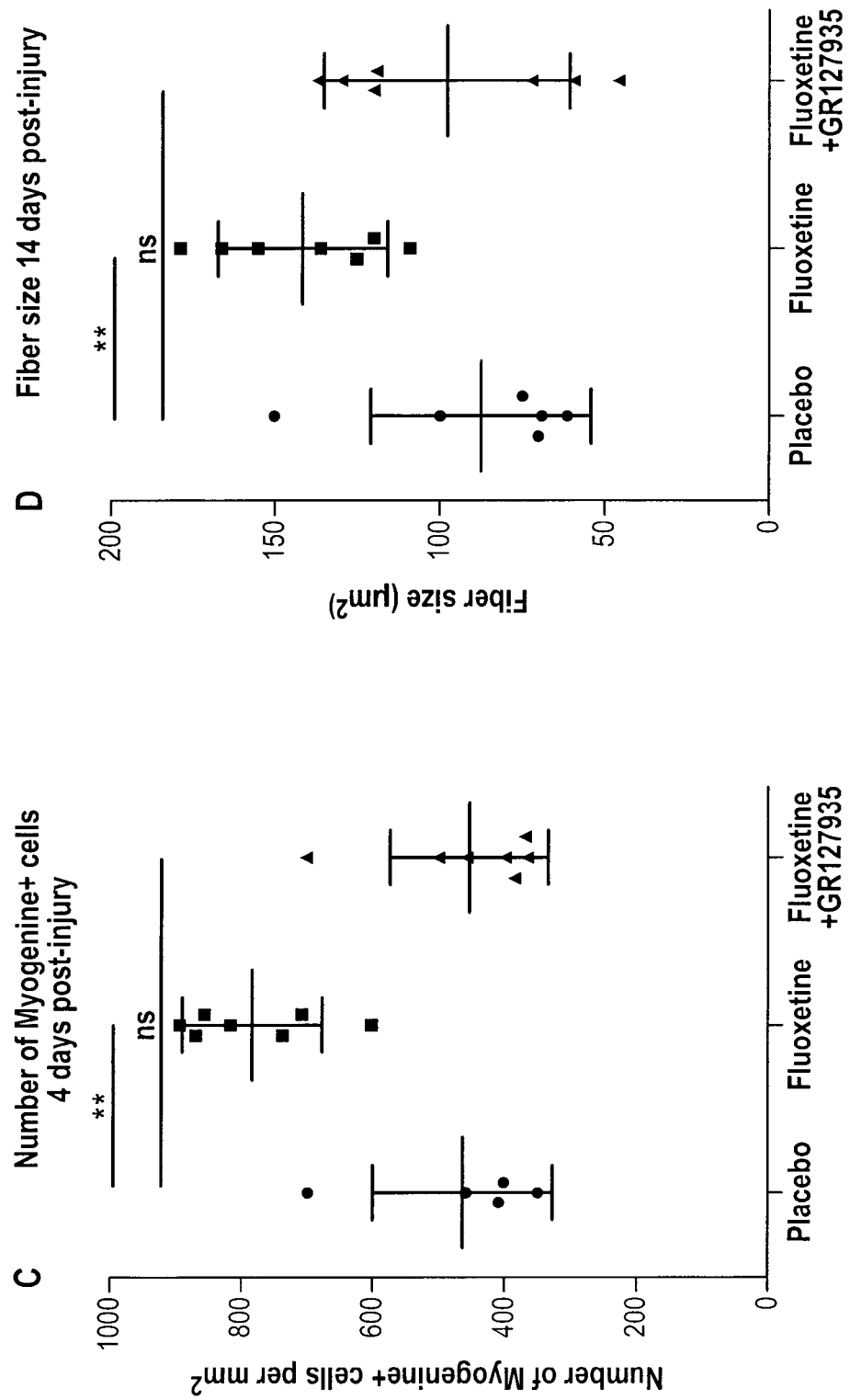

E  Number of Myogenine+ cells 4 days post-injury, fluoxetine and 5HT2B inhibition F  Number of SC after fluoxetine and 5HT2B inhibition G  Number of vessels after fluoxetine and 5HT2B inhibition

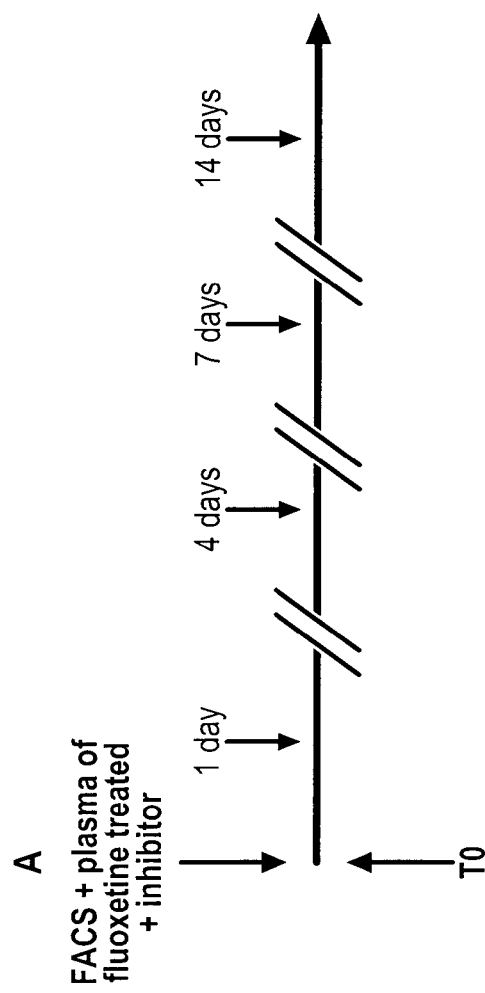

E  Myogenin expression overtime *in vitro* in plasma from fluoxetine treated mice D  Myod expression overtime *in vitro* in plasma from fluoxetine treated mice

5-HYDROXYTRYPTAMINE 1B RECEPTOR-STIMULATING AGENT FOR USE AS A PROMOTER OF SATELLITE CELLS SELF-RENEWAL AND/OR DIFFERENTIATION

INTRODUCTION

The present invention relates to the field of muscle regeneration, and more particularly to the replenishment of the in vivo muscle stem cells pool. It more specifically relates to an agent stimulating, either directly or indirectly, the 5-hydroxytryptamine 1B receptor, and to a composition comprising said agent, for use as i) a promoter of satellite cells self-renewal and/or differentiation, and/or ii) an agent preventing and/or inhibiting the satellite cells pool exhaustion. The invention further encompasses therapeutic and screening methods.

Satellite cells are muscle stem cells that are located between a myofiber and its basal lamina, and that participate in the development and regeneration of muscle tissue.

In mature muscles, satellite cells are typically quiescent but can be recruited as needed, following subtle or massive muscle trauma. When muscle damage is minimal, satellite cells and/or their progeny fuse with existing myofibers; in contrast, upon massive muscle damage, satellite cells fuse with each other to form new myofibers (Grounds and Yablonka-Reuveni, 1993; Hawke and Garry, 2001). However, since subtle myofiber injuries occur routinely during normal muscle activity, the need for ongoing repair is essential for muscle maintenance. This repair is possible thanks to a continuous self-renewal of the satellite cells which involves a complex process comprising not only the proliferation of these cells, but also their stocking and differentiation into mature myocytes.

The proliferation of satellite cells is typically activated upon minor or major injury or disruption of the muscle basal lamina, which ultimately leads some of these cells to differentiate into new myogenic cells and some others to re-establish a residual in vivo reserve of quiescent cells that have the capacity of supporting additional rounds of regeneration (Moss and Leblond, 1971; Schulz and Jaryszak, 1985; Bischoff, 1994). This "two-fate" process more specifically occurs according to the following stages, which can be tracked by monitoring the transcriptome and molecular profile of biomarkers expressed in these cells: in regenerating muscle, the satellite cell pool contains heterogeneous Pax7+ cells, most notably distinguished based on the expression of Myf5 at some point in their lineage. The Pax7+/Myf5− cells (i.e. cells that have never expressed Myf5 and also have not had ancestors who expressed Myf5) represent a population capable of self-renewal and differentiation into the Pax7+/Myf5+ cells. Once Myf5 expression has occurred in a cell, said cell and its progeny are committed to proliferation and differentiation (Kuang, Kuroda et al. 2007). These differences are achieved via asymmetric cell division that is governed by the physical properties of the satellite cell pool. Each satellite cell has indeed a basal side in contact with the basal lamina and an apical side in contact with the host myofiber. When a satellite cell divides, the daughter cell next to the basal lamina undergoes self-renewal while the daughter cell in contact with the myofiber will undergo transient amplification and differentiation. As the myogenic pathway progresses, MyoD becomes also expressed in Pax7+/Myf5+ activated cells (i.e. self-renewing cells). It has nevertheless been observed that there is a population of self-renewing MyoD− cells that express Myf5 when satellite cells are forced to differentiate: these cells actually dedifferentiate and replenish the satellite cell niche (Baroffio, Hamman et al., 1996; Beauchamp, Helsop et al., 2000). Along with a continued expression of MyoD and Myf5, myogenin and MRF4 expression (among others) becomes upregulated in differentiating cells, while the expression of Pax7 decreases (Smith, Janney et al., 1994; Yablonka-Reuveni, 1994; Cornelison and Wold, 1997). This leads to cell cycle arrest through the activation of p21, and to expression of muscle-specific proteins such as myosin heavy chain (Charge and Rudnicki, 2004), followed by an upregulation of the expression of M-cadherin, m-caplain, and intermediate filament proteins such as desmin, and vimentin in order to form a mature, multinucleated myofiber (Kuch et al.; 1997; Kwak et al., 1993; Smythe et al, 2001; Vaittinen et al., 2001). Thus, muscle regeneration is a complex multistep process initiated by the activation of satellite cells, which drives both their self-renewal and differentiation into mature myofibers.

The regenerative capacity of satellite cells is nevertheless not unlimited. Indeed, a decline in the satellite cells abundance and/or function with age may further limit myofiber repair and contribute to the age-associated muscle loss (Bentzinger et al., 2014; Cosgrove et al., 2014; Bernet al., 2014; Goodell et al., 2015). Age-related myopathies, such as sarcopenia, have been reported both in humans and animals, and are characterized by a decline in mass, strength and endurance of skeletal muscles, which can in turn lead to an increased susceptibility to contraction-induced muscle damage. It has also been established that exhaustion of the satellite cell population is an important factor in the deterioration and demise of patients affected by congenital myopathies such as Duchenne Muscular Dystrophy. Kudryashova et al. (2012) notably reported that satellite cells senescence is an underlying feature of myopathies in a rodent model of muscular dystrophy. The precise implication of satellite cells into congenital and acquired myopathies is nevertheless not fully understood.

Hence, there is a continuous demand for functional satellite cells throughout life, whether the decline in their in vivo pool results from a natural (age-related) or pathological (congenital or injury-related) loss and/or damage and/or impairment of skeletal muscle tissue(s).

The present invention addresses the above discussed need in the art.

In particular, the inventors have surprisingly and unexpectedly discovered that fluoxetine and vortioxetine promote satellite cells proliferation, by notably increasing their division rate. They notably increase the muscle fiber diameter in an in vivo model of Duchenne muscular dystrophy, and also enhance muscle regeneration in a sustainable way even after multiple rounds of injury. The present results thus demonstrate that these antidepressant agents can be used to induce muscle regeneration and slow the progression of muscular dystrophies. The inventors further discovered that these surprising effects were mediated by the 5-hydroxytryptamine 1B receptor expressed in muscle tissue, which suggests that any agent (selective or non-selective) that stimulates the 5-hydroxytryptamine 1B receptor, directly or indirectly, would exert similar advantageous action on satellite cells.

Accordingly, the present invention is directed to a 5-hydroxytryptamine 1B receptor-stimulating agent, and to a composition comprising said agent, for use as:

i) a promoter of satellite cells self-renewal and/or differentiation, and/or ii) an agent preventing and/or inhibiting the satellite cells pool exhaustion.

The invention further encompasses in vitro uses, as well as therapeutic and screening methods.

DETAILED DESCRIPTION OF THE INVENTION

Unless stated otherwise, scientific and technical terms used in connection with the present invention shall have the meanings that are commonly understood by those of ordinary skill in the art. Furthermore, unless otherwise required by context, nomenclatures used herein, and techniques of molecular biology, cell culture, and pharmacology are those well-known and commonly used in the art. Such techniques are fully explained in the literature (see Ausubel et al., Current Protocols in Molecular Biology, Eds., John Wiley & Sons, Inc. New York, 2013; Remington: The Science and Practice of Pharmacy, 22nd ed., Mack Publishing Co., Easton, Pa., 2012).

Nevertheless, with respect to the use of different terms throughout the current specification, the following definitions more particularly apply.

In the context of the present invention, the term "5-hydroxytryptamine receptor", "5-HT receptor", "5-HT R" or "serotonin receptor", refers to a superfamily of single-polypeptide 7 transmembrane receptors, found in the central and peripheral nervous systems of almost all animals, that act through the activation of G protein signaling pathways and/or as ligand-gated ion channels. 5-hydroxytryptamine receptors are activated by their natural ligand, serotonin, in order to modulate the release of many neurotransmitters, such as glutamate, GABA, dopamine, epinephrine/norepinephrine, and acetylcholine, as well as many hormones such as oxytocin, prolactin, vasopressin, cortisol, corticotropin, and substance P, among others.

The 5-hydroxytryptamine receptors are further categorized into 7 groups according to their G-protein coupling, among which the 5-HT1 group, which is of a particular interest in the context of the present invention.

The "5-HT1 receptor group" comprises the 5-HT1 A, B, D, E and F subtypes, which share in humans between 40 to 63% structural homology, and preferentially couples to Gαi/o proteins. Activation of the 5-HT1 receptor subtypes typically elicits an inhibitory neurotransmission through activation of potassium channels, which decreases intracellular cAMP production.

Among the 5-HT1 receptor group, the "5-HT1 B receptor" ("5-hydroxytryptamine 1B receptor", "5-hydroxytryptamine receptor 1B", "5-HT-1B", "5-HT-1 D-beta", "serotonin 1D beta receptor", or "serotonin receptor 1B") has been identified and characterized in 1992 by Jin et al. In humans, it is encoded by the HTB1R gene (NCBI RefSeq accession and version numbers NM_000863.1 and GI: 4504532; corresponding encoded protein: NCBI RefSeq accession and version numbers NP_000854.1 and GI:4504533), which is localized on chromosome 6 in position 6q13. The sequence of this receptor is highly conserved in humans, chimpanzee, Rhesus monkey, dog, cow, mouse, rat, chicken, zebrafish, *C. elegans*, and frog; and so far 135 organisms are known to have orthologs with the human gene HTR1B.

By "5-hydroxytryptamine 1B receptor (5-HT1 BR)-stimulating agent", or "5-HT1 BR-stimulating agent", it is meant herein an active agent capable of stimulating, either directly or indirectly, the activity of the 5-hydroxytryptamine 1B receptor, or in other words, capable of mimicking or enhancing the effects that are usually exerted by the natural ligand of said receptor (i.e. serotonin). A direct stimulation requires the binding of the agent to said receptor, while an indirect stimulation does not involve the binding of said agent to said receptor (i.e. it acts on the receptor via another mechanism of action). The capacity of a candidate agent to activate said receptor can be assessed by methods well-known in the art, for example by overexpressing 5-HT1 BR in cells and measuring intracellular cAMP production before and after contact of the recombinant cells with said candidate agent. Other methods for measuring the activity of 5-HT1 BR have been described in the art, and include, among others, a reverse phase high performance liquid chromatography coupled to an electrochemical detector (HPLC-ED) using an amperometric detector. In the context of the present invention, said agent can be selective for the 5-hydroxytryptamine 1B receptor, or may act not only on the 5-hydroxytryptamine 1B receptor but also on other receptors such as other 5-HT receptors. In any case, the promotion of satellite cells self-renewal and/or differentiation, and/or the prevention and/or inhibition of satellite cells pool exhaustion, as proposed herein, is mediated via the direct or indirect stimulation of the 5-hydroxytryptamine 1B receptor by the agents of the invention.

According to the different aspects and embodiments of the invention described herein, a "subject" or "host" refers to a subject possessing a serotonergic system, said system comprising more particularly 5-hydroxytryptamine receptors, including notably the 5-hydroxytryptamine 1B receptor. Said subject thus preferably includes animals and humans.

In addition, by "satellite cells", it is meant herein small mononuclear stem cells that are naturally located underneath the basal lamina of the myofiber, and that are capable of self-renewal and of forming new skeletal muscle cells (i.e. myogenic). The most definitive marker of satellite cells is Pax7, which is present in all satellite cells of post-natal muscles and expressed in proliferating myoblasts until they begin to differentiate. Other transcription factors common to quiescent satellite cells include Foxk1 and Pax3. Cell surface markers can also be used to distinguish satellite cells from surrounding tissue, including CD56 (the neural cell adhesion molecule, or NCAM), the hepatic growth factor (HGF) receptor, and c-Met. M-cadherin (Cdh15) is also typically present in quiescent satellite cells and is upregulated once they become activated. Other markers include CD106 (VCAM-1), CD34, syndecans 3 and 4, Sox8 and Sox15. MyoD, Myf6 and Myf5 expression begins once satellite cells become activated, followed by the expression of myogenin (MyoG), Desmin, and MRF4 which indicates that the cells are undergoing differentiation into myotubes. The main cell markers expressed at each stage of the muscle regeneration process are summarized on FIG. 1. It is within the skill of the person in the art to assess the presence or absence of said cell markers by methods well-known in the art, such as by FACS (fluorescence-activated cell sorting).

By "satellite cells pool", it is meant herein the natural in vivo reserve or stock of satellite cells existing in a subject, that is located between the plasmalemma and basal lamina of the muscle fiber. This pool solely consists in quiescent (i.e. dormant) satellite cells, of which the cell phenotype is Pax7+ and/or Pax3+. Particularly, said phenotype may be CD34+, Cdh15+, Foxk1+, Met+, Pax3+, Pax7+, Sdc3/4+, Sox8+, Sox15+, VCAM1+, Myf5−, Myf6−, MyoD−, Desmin−, MyoG−, and MRF4−. More particularly, the cell phenotype of quiescent (i.e. dormant) satellite cells may be CD34+, Cdh15+, Foxk1+, Met+, Pax3+, Pax7+, Sdc3/4+, Sox8+, Sox15+, VCAM1+, Myf5−, Myf6−, MyoD−, Desmin−, MyoG−, MRF4−, CD56+, and MyHC−.

The "satellite cells pool exhaustion" thus refers to the depletion or decrease of said quiescent cells. The term "self-renewal of satellite cells" means herein that said cells proliferate or divide so as to generate a progeny, which will either become quiescent or undergo cellular differentiation. Accordingly, the cell phenotype of proliferative or self-renewing satellite cells is Pax7+, Myf5+, MyoD+, Desmin−, MyoG− and MRF4−. Particularly, said phenotype may be CD34+, Cdh15+, Foxk1+, Met+, Pax3+, Pax7+, Sdc3/4+, Sox8+, Sox15+, VCAM1+, Myf5+, Myf6+, MyoD+, Desmin−, MyoG−, and MRF4−. More particularly, the cell phenotype of proliferative or self-renewing satellite cells may be CD34+, Cdh15+, Foxk1+, Met+, Pax3+, Pax7+, Sdc3/4+, Sox8+, Sox15+, VCAM1+, Myf5+, Myf6+, MyoD+, Desmin−, MyoG−, MRF4−, CD56+, and MyHC−.

The term "differentiation of satellite cells" refers herein to the cellular process by which said cells change from one cell phenotype to another in order to form mature muscle fibers, more particularly from a self-renewing cell phenotype to a myoblast phenotype, then to a myotube phenotype. Accordingly, the cell phenotype of differentiating satellite cells is Desmin+, MyoG+ and MRF4+, while the cell phenotype of fully differentiated satellite cells is MyHC+. Particularly, the phenotype of differentiating satellite cells may be CD34+, Cdh15+, Foxk1+, Met+, Pax3+, Pax7+ Sdc3/4+, Sox8+, Sox15+, VCAM1+, Myf5+, Myf6+, MyoD+, Desmin+, MyoG+, and MRF4+(i.e. myoblast phenotype), while the cell phenotype of fully differentiated satellite cells may be CD34−, Cdh15−, Foxk1−, Met−, Pax3−, Pax7−, Sdc3/4−, Sox8−, Sox15−, VCAM1−, Myf5+, Myf6+, MyoD+, Desmin+, MyoG+, and MRF4+ and MyHC+(i.e. myotube phenotype). More particularly, the cell phenotype of differentiating satellite cells may be CD34+, Cdh15+, Foxk1+, Met+, Pax3+, Pax7+/−, Sdc3/4+, Sox8+, Sox15+, VCAM1+, Myf5+, Myf6+, MyoD+, Desmin+, MyoG+, MRF4+, CD56+/−, and MyHC+/−(i.e. myoblast phenotype), while the cell phenotype of fully differentiated satellite cells may be CD34−, Cdh15−, Foxk1−, Met−, Pax3−, Pax7−, Sdc3/4−, Sox8−, Sox15−, VCAM1−, Myf5+, Myf6+, MyoD+, Desmin+, MyoG+, MRF4+, CD56−, and MyHC+ (i.e. myotube phenotype).

Additional definitions are provided throughout the specification.

The present invention may be understood more readily by reference to the following detailed description, including preferred embodiments of the invention, and examples included herein.

The present inventors have discovered that, upon contact with fluoxetine or vortioxetine, well-known inhibitors of serotonin reuptake which increase serotonin levels and in turn stimulate 5-HT1 BR (the fluoxetine acting indirectly on 5-HT1 BR and the vortioxetine acting indirectly as well as directly on 5-HT1 BR as a partial agonist of said receptor), satellite cells present in injured muscle undergo a more active as well as a faster cell division as compared to non-treated animals, which leads to the differentiation of satellite cells into mature myotubes and to the apparition of new reserve quiescent satellite cells. They further demonstrated that fluoxetine improved the muscular phenotype in a Duchenne muscular mouse model (Mdx), by notably reducing the necrosis of myofibers, increasing the size of myofibers, and decreasing markers of inflammation.

The present invention thus proposes to use agents stimulating 5-HT1 BR activity as novel drugs for favoring the proliferation and differentiation of satellite cells and preventing their in vivo exhaustion, thereby promoting muscle regeneration.

Thus, in a first aspect, the present invention is directed to a 5-hydroxytryptamine 1B receptor (5-HT1 BR)-stimulating agent, for use as:
 i) a promoter of satellite cells self-renewal and/or differentiation; and/or
 ii) an agent preventing and/or inhibiting the satellite cells pool exhaustion.

As stated above, said agent can either act directly or indirectly on said 5-HT1 BR.

More precisely, the invention relates to the use of a 5-hydroxytryptamine 1B receptor (5-HT1 BR)-stimulating agent as described herein, for i) promoting satellite cells self-renewal and/or differentiation and/or ii) preventing and/or inhibiting the satellite cells pool exhaustion.

Said use may be an in vivo or an in vitro use, preferably an in vivo use.

More particularly, the invention relates to the use of a 5-hydroxytryptamine 1B receptor (5-HT1 BR)-stimulating agent as described herein, for manufacturing a medicament to i) promote satellite cells self-renewal and/or differentiation and/or ii) prevent and/or inhibit the satellite cells pool exhaustion.

In other words, the invention relates to a method for i) promoting satellite cells self-renewal and/or differentiation and/or ii) preventing and/or inhibiting the satellite cells pool exhaustion, comprising the step of administering an effective amount of a 5-hydroxytryptamine 1B receptor (5-HT1 BR)-stimulating agent as described herein, to a subject in need thereof.

The invention also relates to the in vitro use of a 5-hydroxytryptamine 1B receptor (5-HT1 BR)-stimulating agent as described herein, for i) promoting satellite cells self-renewal and/or differentiation.

In other words, the invention relates to an vitro method for i) promoting satellite cells self-renewal and/or differentiation, comprising the step of administering an effective amount of a 5-hydroxytryptamine 1B receptor (5-HT1 BR)-stimulating agent as described herein to an isolated biological sample comprising satellite cells, in particular a satellite cells pool. Said biological sample can be herein a muscle sample.

By "effective amount", it is meant herein that the agent of the invention is administered in a quantity sufficient to provide the effect for which it is indicated, i.e. promotion of satellite cells self-renewal and/or differentiation, and/or prevention and/or inhibition of the satellite cells pool exhaustion.

The satellite cell self-renewal and/or differentiation and replenishment of the satellite pools can be assessed by analyzing the satellite cells phenotype as described above.

According to a further preferred embodiment, the 5-hydroxytryptamine 1B receptor (5-HT1 BR)-stimulating agent is used in the present invention in a subject affected by a natural or by a pathological loss and/or damage and/or impairment of skeletal muscle tissue(s).

The term "natural loss and/or damage and/or impairment of skeletal muscle tissue(s)" encompasses herein the natural process of muscle ageing, which results in progressive skeletal muscle loss. It includes, without limitation, sarcopenia and its related complications, such as decreased muscle strength (i.e. muscle weakness), bone fractures, and loss of mobility and physical function. Typically, modest amounts of muscle mass start to decrease at age 30 in humans, but the resulting loss of strength increases exponentially with age.

The prevalence of muscle loss is known to increase from 15-25% among people under 70 years old to more than 50% among those over 80 years old. Accordingly, in a preferred embodiment, said subject affected by a natural loss and/or damage and/or impairment of skeletal muscle tissue(s) is an adult subject, preferably of at least 30 years of age, more preferably of at least 70 years of age, and even more preferably of at least 80 years of age. With regard to sarcopenia, class I sarcopenia has been defined in the literature by Messier et al. (2009) as an appendicular lean body mass index (ALBMI)<or=6.44 kg·m$^{-2}$ (appendicular lean body mass/height), which can be identified by scanning of the legs and/or arms to determine muscle bulk. Accordingly, in a preferred embodiment, said subject affected by a natural loss and/or damage and/or impairment of skeletal muscle tissue(s) has an ALBMI inferior or equal to about 6 kg/m$^2$, preferably inferior or equal to about 6.3 kg/m$^2$, more preferably inferior or equal to about 6.4 kg/m$^2$, and even more preferably inferior or equal to about 6.44 kg/m$^2$. Sarcopenia can also be identified by measuring anthropometric measurements, such as arm muscle circumference and calf circumference to determine a below normal amount of limb skeletal muscle (Bauer et al., 2008). Baumgartner et al. (1998) further identified sarcopenia when skeletal muscle mass in an older subject is more than 2 standard deviations below the mean for healthy younger adults.

By "pathological loss and/or damage and/or impairment of skeletal muscle tissue(s)", it is meant herein any congenital or acquired muscular degenerescence, weakness, dysfunction and/or loss affecting the skeletal muscle(s). Typical congenital pathologies affecting the skeletal muscle(s) include, without limitation, myopathies such Duchenne muscular dystrophy (DMD), Becker muscular dystrophy, Congenital muscular dystrophy, Limb Girdle muscular dystrophy (LGMD), facioscapulohumeral muscular dystrophy, myotonic muscular dystrophy, oculopharyngeal muscular dystrophy, distal muscular dystrophy, and Emery-Dreifuss muscular dystrophy. In contrast, acquired pathologies affecting the skeletal muscle(s) are not inherited and can be induced by inflammation (inflammatory myopathies), drugs (drug-induced myopathy), a traumatism or injury (trauma-induced myopathy, or surgery-induced myopathy), connective tissue and muscle ischemia (Buerger disease), cancer (cancer-induced sarcopenia) or even diet (diet-induced myopathy).

According to a preferred embodiment, the 5-HT1 BR-stimulating agent used in the present invention is selected from the group consisting of antidepressant agents and antimigraine drugs, pharmaceutically acceptable derivatives, analogs, isomers, metabolites, salts, solvates, clathrates, polymorphs, and co-crystals thereof, and combinations thereof.

By "derivative", it is meant herein a compound that is directly derived from a chemical compound of interest (i.e. 5-HT1 BR-stimulating agent) and is structurally similar though non-identical to said compound, and which retains the same biological activity and/or physico-chemical properties.

By "analog", or "functional analog", it is meant herein a compound that is not directly derived from a chemical compound of interest and is thus structurally different, but exhibits the same biological activity and/or physico-chemical properties, such as isosters.

"Derivatives" and "analogs" of the 5-HT1 BR-stimulating agents according to the invention encompass herein compounds that retain the 5-HT1 BR-stimulating activity as defined above, but that do not cross the blood-brain barrier, as further described below.

By "isomer", it is meant herein a compound having the same chemical formula as a compound of interest, but a different chemical structure. This term encompasses structural isomers and stereoisomers. Should the isomer of the invention be a stereoisomer, the individual stereoisomers (enantiomers and diastereoisomers) and mixtures thereof are included within the scope of the invention. Some of the compounds according to the invention may exist in tautomeric forms (a type of structural isomer), which are also included within the scope of the invention.

By "metabolite" as used herein, it is meant any compound that is an intermediate and/or a product of metabolism. A metabolite from a chemical compound is usually formed as part of the natural biochemical process of degrading and eliminating the compound of interest in a subject to which it is administered. Examples of metabolites of antidepressant agents according to the invention are provided further below.

The term "pharmaceutically acceptable salt" or "salt" as used herein refers to a salt that is physiologically tolerated (i.e. non-toxic) when used in an appropriate manner in the context of the present invention, particularly when used on mammals. Pharmaceutically acceptable salts include those derived from pharmaceutically acceptable inorganic and organic acids and bases. Examples of suitable acids according to the invention include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric, benzenesulfonic, gluconic, glutamic, bis-methylenesalicylic, ethanedisulfonic, propionic, p-amino-benzoic, malic, mandelic, cinnamic, citraconic, aspartic, stearic, palmitic, itaconic and sulfamic acids, as well as theophylline acetic acids and 8-halotheophyllines such as the 8-bromotheophylline. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal, (e.g., magnesium), ammonium and N—(C1-C4 alkyl)$_4^+$ salts.

The term "solvate" according to the invention should be understood as meaning any form of the active agent in accordance with the invention (i.e. 5-HT1 BR-stimulating agent), in which said compound is linked through non-covalent interactions to another molecule (normally a polar solvent), including especially hydrates and alcoholates, such as methanolate. Methods of solvation are well-known in the art.

By "clathrate", it is meant herein a chemical substance consisting of a lattice or cage that entraps or contains a second type of molecule/compound of interest, and which can be used to increase the stability and solubility in water of the molecule/compound of interest. Clathrates are typically polymeric.

The term "polymorphs" means herein different crystalline forms of a compound of interest in which molecules have different arrangements and/or different molecular conformation. It includes crystalline liquid form or crystalline solid form of a compound of interest. Hydrates and clathrates can be polymorphs.

By "co-crystal", it is meant herein a crystalline structure composed of at least two components, where the components may be atoms, ions or molecules. Solvates and clathrates may be co-crystals in certain conditions.

In the context of the present invention, the pharmaceutically acceptable derivatives, analogs, isomers, metabolites, salts, solvates, clathrates, polymorphs, and co-crystals as defined above are active, i.e. they exhibit a 5-HT1 BR-stimulating activity. Said activity can be assessed as described above.

It shall further be understood that the 5-HT1 BR-stimulating agents as described herein, or their derivatives, analogs, isomers, metabolites, salts, solvates, clathrates, polymorphs, and co-crystals are preferably in pharmaceutically acceptable or substantially pure form. By pharmaceutically acceptable form, it is meant, inter alia, having a pharmaceutically acceptable level of purity, i.e. excluding normal pharmaceutical additives, such as diluents and carriers, and any material considered toxic at normal dosage levels. In the context of the present invention, purity levels are preferably above 98%, more preferably above 99%, and even more preferably above 99.9%. In a preferred embodiment, said purity level is 99.9%.

As stated above, the 5-HT1 BR-stimulating agents according to the invention can be selected among antimigraine drugs, such as triptans or ergotamine. Triptans are well-known in the art as tryptamine-based drugs used in the treatment of migraines and cluster headaches, thanks to their agonistic effects on 5-HT1 BR and 5-HT1 DR. Examples of triptans according to the invention include, but are not limited to, sumatriptan, rizatriptan, zolmitriptan, eletriptan, almotriptan, frovatriptan, naratriptan, avitriptan, and donitriptan. Non limitative examples of salts of said compounds are donitriptan hydrochloride, eletriptan hydrobromide, and rizatriptan benzoate.

Ergotamine:

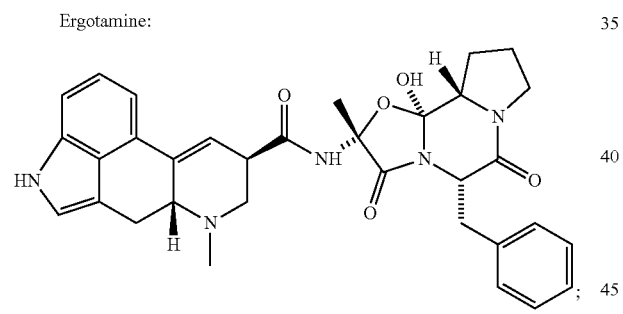

Sumatriptan:

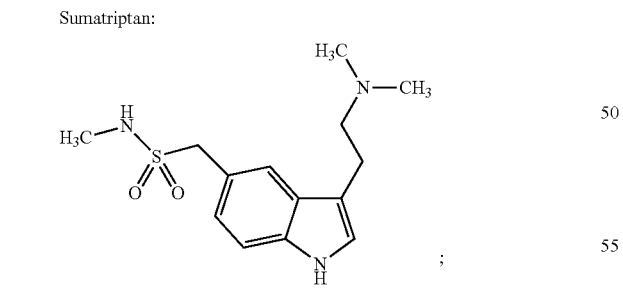

Rizatriptan:

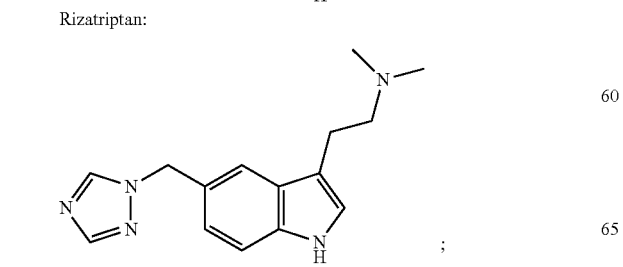

Zolmitriptan:

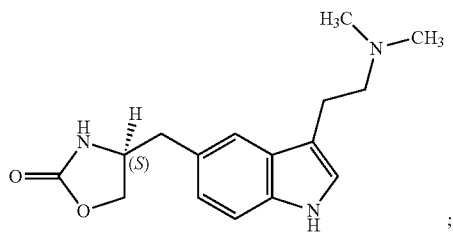

Eletriptan:

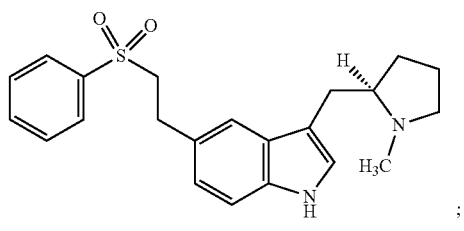

Almotriptan:

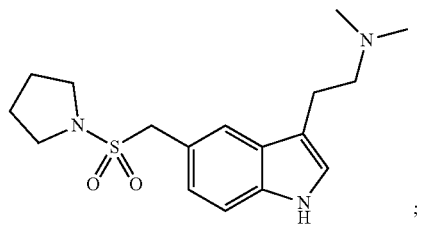

Frovatriptan:

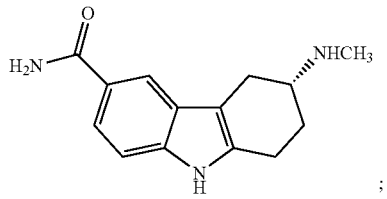

Naratriptan:

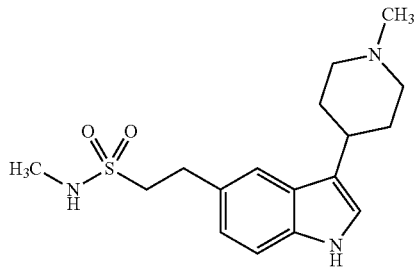

Avitriptan:

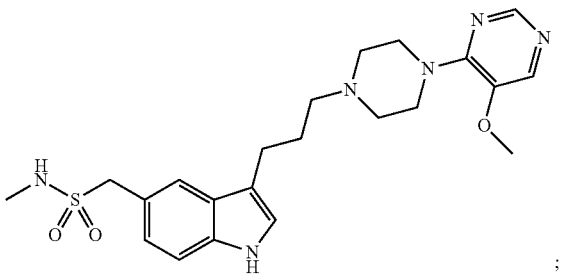

Donitriptan:

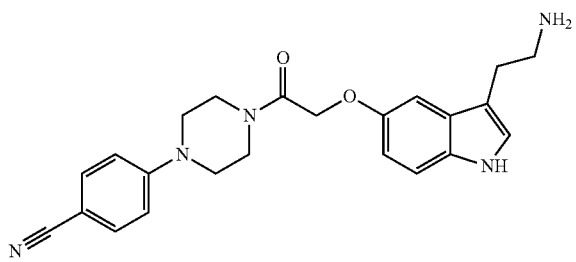

Particularly preferred triptans according to the invention are selected from the group consisting of sumatriptan, rizatriptan, zolmitriptan, eletriptan, almotriptan, and frovatriptan.

The 5-HT1 BR-stimulating agents according to the invention can alternatively be selected among antidepressant agents.

By "antidepressant agent", it is meant herein an active agent that is capable to treat mood disorders, such as depression (including severe depression) and/or dysthymia. Antidepressant agents according to the invention include, without limitation, serotonin reuptake inhibitors (SRIs); tricyclic antidepressants (TCAs); monoamine oxidase inhibitors (MAOs); noradrenergic and specific serotoninergic antidepressants (NaSSAs); atypical antidepressants or antidepressant enhancers.

Serotonin reuptake inhibitors (SRIs) designate a class of compounds that typically act by inhibiting the reuptake of the serotonin neurotransmitter into the presynaptic terminal, thereby increasing the serotonin extracellular level and thus serotoninergic transmission. Such compounds can act selectively or non-selectively on the neurotransmitter serotonin. SRIs can indeed also display various degrees of selectivity towards the other monoamine reuptake systems, in particular the transporters for norepinephrine and dopamine. SRIs typically include selective serotonin reuptake inhibitors (SSRIs), serotonine and norepinephrine reuptake inhibitors (SNRIs) and serotonin-norepinephrine-dopamine reuptake inhibitor (SNDRIs).

Examples of selective serotonin reuptake inhibitors (SSRIs) include, without limitation, fluoxetine, citalopram, escitalopram, sertraline, norsertraline, paroxetine, fluvoxamine, femoxetine, indalpine, alaproclate, cericlamine, ifoxetine, zimelidine, dapoxetine, and etoperidone, preferably fluoxetine, citalopram, escitalopram, sertraline, norsertraline, paroxetine, fluvoxamine, femoxetine, indalpine, alaproclate, cericlamine, ifoxetine and zimelidine.

Fluoxetine:

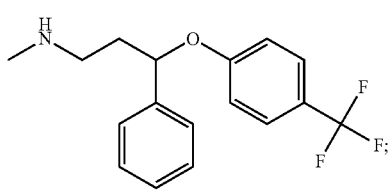

Citalopram:

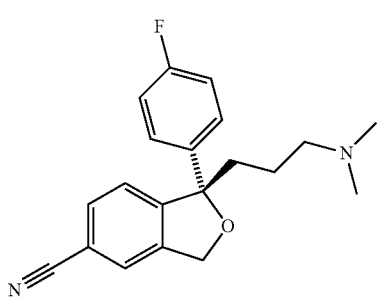

Examples of active SSRIs metabolites include, without limitation, desmethylcitalopram, didesmethylcitalopram, and seproxetine (i.e. (S)-norfluoxetine).

Examples of serotonine and norepinephrine reuptake inhibitors (SNRIs) include, without limitation, duloxetine, venlafaxine, desvenlafaxine, milnacipran, levominalcipran, and sibutramine.

Examples of serotonin-norepinephrine-dopamine reuptake inhibitor (SNDRIs) (also known as triple reuptake inhibitor or TRI) include, without limitation, bicifadine, brasofensine, tesofensine and nomifensine, preferably bicifadine.

Examples of tricyclic antidepressants (TCAs) according to the invention include, without limitation, clomipramine, amoxapine, nortriptyline, maprotiline, trimipramine, imipramine, desipramine and protriptyline.

Examples of monoamine oxidase inhibitors (MAOs) according to the invention include, without limitation, iproniazide, phenelzine, tranylcipromine, moclobemide, selegiline and rasagiline.

Examples of noradrenergic and specific serotoninergic antidepressants (NaSSAs), acting preferably by blocking presynaptic alpha-2 adrenergic receptors, include, among others, mirtazapine, mianserin, aptazapine, esmirtazapine, setiptiline and S32212 (also known as N-[4-methoxy-3-(4-methylpiperazin-1-yl)phenyl]-1,2-dihydro-3H-benzo[e]indole-3-carbo-xamide), preferably mirtazapine and mianserin.

Examples of atypical antidepressants (defined as such as they do not belong to any of the foregoing classes of antidepressants) or antidepressant enhancers include, without limitation, bisarylsulfanyl amines such as vortioxetine, as well as tianeptine, agomelatine, nefazodone, trazodone, buspirone, tandospirone, and ketamine, preferably vortioxetine, tianeptine, agomelatine, nefazodone, trazodone, buspirone, tandospirone, and ketamine.

Bisarylsulfanyl amines have been disclosed in patent application WO 2003/029232, incorporated by reference, and are within the scope of the 5-HT1 BR-stimulating agents according to the invention. Said compounds can be described according to the following general formula (A):

(A)

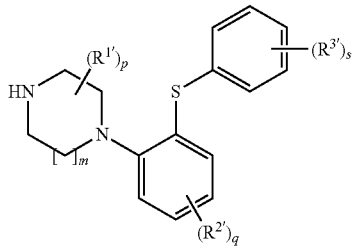

wherein
m is 1 or 2;
p is 0, 1, 2, 3, 4, 5, 6, 7 or 8;
q is 0, 1, 2, 3 or 4;
s is 1 or 2;
each $R^{1'}$ is independently selected from the group represented by $C_{1-6}$-alkyl, or two $R^{1'}$ attached to the same carbon atom may form a 3-6-membered spiro-attached cycloalkyl;
each $R^{2'}$ is independently selected from the groups represented by halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl, $C_{1-6}$-alk(en/yn)ylsulfonyl, or —NRxRy; —NRxCO—$C_{1-6}$-alk(en/yn)yl;
each $R^{3'}$ is independently selected from a group represented by halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, $C_{1-6}$-alk(en/yn)ylsulfonyl, aryl, $C_{1-6}$-alk(en/yn)yloxycarbonyl, acyl, —$NR^xCO$—$C_{1-6}$-alk(en/yn)yl, $CONR^xR^y$ or $NR^xR^y$;
or two adjacent $R^{3'}$ substituents together form a heterocycle fused to the phenyl ring selected from the group consisting of

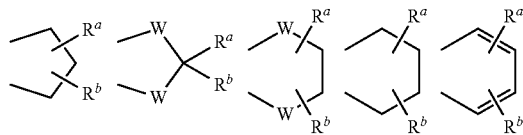

wherein W is O or S, and Ra and $R^{1'}$ are hydrogen or $C_{1-6}$-alkyl; or two adjacent $R^{3'}$ substituents together form a fused heteroaromatic system containing one, two or three heteroatoms,
wherein each $R^x$ and $R^y$ is independently selected from the group represented by hydrogen, $C_{1-6}$-alk(en/yn)yl, $C_{3-8}$-cycloalk(en)yl, $C_{3-8}$-cycloalk(en)yl-$C_{1-6}$-alk(en/yn)yl, or aryl; or $R^x$ and $R^y$ together with the nitrogen to which they are attached form a 3-7-membered ring which optionally contains one further heteroatom;
or a pharmaceutically acceptable salt thereof.

Synthesis of compounds of general formula (A) is fully described in WO 2003/029232 and therefore does not need to be detailed herein.

A preferred embodiment of general formula (A) is wherein p is 0.

A preferred embodiment of general formula (A) is wherein m is 1 or 2.

A preferred embodiment of general formula (A) is wherein $R^{2'}$ is trifluoromethyl, or $C_{1-6}$-alkyl.

A preferred embodiment of general formula (A) is wherein $R^{3'}$ is selected from the group consisting of halogen, $C_{1-6}$-alkoxy, $C_{1-6}$-sulfanyl, $C_{1-6}$— alkyl hydroxy and trifluoromethyl.

A more preferred embodiment of general formula (A) is wherein m=1, p=0, q=0, $R^{3'}$ is methyl and s=2.

Particularly preferred embodiment of general formula (A) is wherein the compound of formula (A) is any of the following:
1-[2-(2-Trifluoromethylphenylsulfanyl)phenyl]piperazine,
1-[2-(4-Bromophenylsulfanyl)phenyl]piperazine,
1-{2-[4-(Methylsulfanyl)phenylsulfanyl]phenyl}piperazine,
1-[2-(4-Hydroxyphenylsulfanyl]phenyl}piperazine,
1-[2-(2,4-Dimethylphenylsulfanyl)phenyl]piperazine, also known as vortioxetine Vortioxetine:

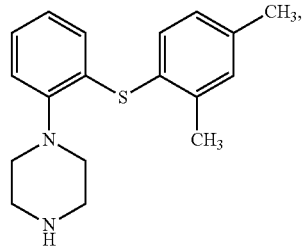

1-[2-(3,5-Dimethylphenylsulfanyl)phenyl]piperazine,
1-[2-(2,6-Dimethylphenylsulfanyl)phenyl]piperazine,
1-[2-(2,5-Dimethylphenylsulfanyl)phenyl]piperazine,
1-[2-(2-Trifluoromethylphenylsulfanyl)phenyl][1,4]diazepane,
1-[2-(3-Methylphenylsulfanyl)phenyl]-[1,4]-diazepane,
2-(4-Methylphenylsulfanyl)phenyl-1-piperazine,
1-[2-(4-Chlorophenylsulfanyl)phenyl]-piperazine,
1-[2-(4-Methoxyphenylsulfanyl)-4-chlorophenyl]piperazine,
1-[2-(4-Methoxyphenylsulfanyl)-4-methylphenyl]piperazine,
1-[2-(4-Methoxyphenylsulfanyl)-5-methylphenyl]piperazine,
1-[2-(4-Fluorophenylsulfanyl)-5-methylphenyl]piperazine,
1-[2-(4-Methoxyphenylsulfanyl)-5-trifluoromethylphenyl]piperazine,
1-[2-(4-Chlorophenylsulfanyl)phenyl]-3-methylpiperazine,
1-[2-(4-Chlorophenylsulfanyl)phenyl]-3,5-dimethylpiperazine,
or a pharmaceutically acceptable salt thereof.

Most preferred embodiment is wherein the compound of formula (A) is 1-[2-(2,4-Dimethylphenylsulfanyl)phenyl]piperazine (i.e. vortioxetine).

"Halogen" means herein fluoro (F), chloro (Cl), bromo (Br) or iodo (I).

"Alkyl", "alkenyl", "alkynyl", and "aryl" are further defined below.

The expression $C_{1-6}$-alk(en/yn)yl means a $C_{1-6}$-alkyl, $C_{2-6}$-alkenyl or a $C_{2-6}$-alkynyl group.

The expression $C_{3-8}$-cycloalk(en)yl means a $C_{3-8}$-cycloalkyl- or cycloalkenyl group.

The term $C_{1-8}$ alkyl refers to a branched or unbranched alkyl group having from one to six carbon atoms, including but not limited to methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms, including one double bond and one triple bond respectively, including but not limited to ethenyl, propenyl, butenyl, ethynyl, propynyl and butynyl.

The term $C_{3-8}$ cycloalkyl designates a monocyclic or bicyclic carbocycle having three to eight C-atoms, including but not limited to cyclopropyl, cyclopentyl, cyclohexyl, etc.

The term $C_{3-8}$ cycloalkenyl designates a monocyclic or bicyclic carbocycle having three to eight C-atoms and including one double bond.

In the term $C_{3-8}$-cycloalk(en)yl-$C_{1-6}$-alk(en/yn)yl, $C_{3-8}$-cycloalk(en)yl and $C_{1-6}$-alk(en/yn)yl are as defined above.

The terms $C_{1-6}$-alk(en/yn)yloxy, $C_{1-6}$ alk(en/yn)ylsulfanyl, hydroxy-$C_{1-6}$-alk(en/yn)yl, halo-$C_{1-6}$-alk(en/yn)yl, halo-$C_{1-6}$-alk(en/yn)yloxy, $C_{1-6}$-alk(en/yn)ylsulfonyl etc. designate such groups in which the $C_{1-6}$-alk(en/yn)yl are as defined above.

As used herein, the term $C_{1-6}$-alk(en/yn)yloxycarbonyl refers to groups of the formula $C_{1-6}$-alk(en/yn)yl —O—CO—, wherein $C_{1-6}$-alk(en/yn)yl are as defined above.

As used herein, the term acyl refers to formyl, $C_{1-6}$-alk(en/yn)ylcarbonyl, arylcarbonyl, aryl-$C_{1-6}$-alk(en/yn)ylcarbonyl, $C_{3-8}$-cycloalk(en)ylcarbonyl or a $C_{3-8}$-cycloalk(en)yl-$C_{1-6}$— alk(en/yn)yl-carbonyl group.

The term 3-7-membered ring optionally containing one further heteroatom as used herein refers to ring systems such as 1-morpholinyl, 1-piperidinyl, 1-azepinyl, 1-piperazinyl, 1-homopiperazinyl, 1-imidazolyl, 1-pyrrolyl or pyrazolyl, all of which may be further substituted with $C_{1-6}$-alkyl.

The heterocycles formed by two adjacent $R^{3'}$ substituents and fused to the parent ring may together form rings such as 5-membered monocyclic rings such as 3H-1,2,3-oxathiazole, 1,3,2-oxathiazole, 1,3,2-dioxazole, 3H-1,2,3-dithiazole, 1,3,2-dithiazole, 1,2,3-oxadiazole, 1,2,3-thiadiazole, 1H-1,2,3-triazole, isoxazole, oxazole, isothiazole, thiazole, 1H-imidazole, 1H-pyrazole, 1H-pyrrole, furan or thiophene and 6-membered monocyclic rings such as 1,2,3-oxathiazine, 1,2,4-oxathiazine, 1,2,5-oxathiazine, 1,4,2-oxathiazine, 1,4,3-oxathiazine, 1,2,3-dioxazine, 1,2,4-dioxazine, 4H-1,3,2-dioxazine, 1,4,2-dioxazine, 2H-1,5,2-dioxazine, 1,2,3-dithiazine, 1,2,4-dithiazine, 4H-1,3,2-dithiazine, 1,4,2-dithiazine, 2H-1,5,2-dithiazine, 2H-1,2,3-oxadiazine, 2H-1,2,4-oxadiazine, 2H-1,2,5-oxadiazine, 2H-1,2,b-oxadiazine, 2H-1,3,4-oxadiazine, 2H-1,2,3-thiadiazine, 2H-1,2,4-thiadiazine, 2H-1,2,5-thiadiazine, 2H-1,2,6-thiadiazine, 2H-1,3,4-thiadiazine, 1,2,3-triazine, 1,2,4-triazine, 2H-1,2-oxazine, 2H-1,3-oxazine, 2H-1,4-oxazine, 2H-1,2-thiazine, 2H-1,3-thiazine, 2H-1,4-thiazine, pyrazine, pyridazine, pyrimidine, 4H-1,3-oxathiin, 1,4-oxathiin, 4H-1,3-dioxin, 1,4-dioxin, 4H-1,3-dithiin, 1,4-dithiin, pyridine, 2H-pyran or 2H-thiin.

Further, the compounds of general formula (A) may exist in unsolvated as well as in solvated forms with pharmaceutically acceptable solvents such as water, ethanol and the like, Some of the compounds of general formula (A) contain chiral centers and such compounds exist in the form of isomers (i.e. enantiomers). Such isomers and any mixtures thereof including racemic mixtures are also within the scope of the invention.

Particularly preferred antidepressant agents according to the invention are selected from the group consisting of bisarylsulfanyl amines as described above such as vortioxetine, and fluoxetine, citalopram, escitalopram, sertraline, paroxetine, fluvoxamine, femoxetine, indalpine, alaproclate, zimelidine, duloxetine, venlafaxine, desvenlafaxine, milnacipran, levomilnacipran, sibutramine, bicifadine, clomipramine, amoxapine, maprotiline, imipramine, desipramine, moclobemide, selegiline, mirtazapine, mianserin, tianeptine, agomelatine, trazodone, buspirone, tandospirone, and ketamine. More preferably, antidepressant agents according to the invention are selected from the group consisting of bisarylsulfanyl amines as described above such as vortioxetine, and fluoxetine.

Other suitable 5-HT1 BR-stimulating agents according to the invention can be: anpirtoline hydrochloride, CGS-12066A, CGS 12066B dimaleate, oxymetazoline, 5-carboxamidotryptamine, CP-93129 and salts thereof such as CP-93129 dihydrochloride, CP-94253 and salts thereof such as CP-94253 hydrochloride, CP-122,288, CP-135,807, RU-24969 and salts thereof such as RU-24969 hemisuccinate, ziprasidone, asenapine, 5-nonyloxytryptamine oxalate, pindolol and (S)-(−)-pindolol.

According to a preferred embodiment, the 5-HT1 BR-stimulating agent used in the present invention is an antidepressant selected from the group consisting of atypical antidepressants and SRIs, in particular SSRIs.

More preferably, the 5-HT1 BR-stimulating agent of the present invention is the atypical antidepressant vortioxetine or the SSRI fluoxetine. Most preferably, the 5-HT1 BR-stimulating agent of the present invention is vortioxetine.

Nevertheless, in the event that the 5-hydroxytryptamine 1B receptor (5-HT1 BR)-stimulating agent of the present invention exerts undesired CNS-related adverse effects, it is particularly advantageous to limit the effects of said agent onto the peripheral serotonin system. Antidepressant agents are notably well-known for exerting such side effects. Side effects can be prevented by chemically modifying the structure of said agent, and by notably grafting a charged chemical moiety to prevent crossing of the blood-brain barrier.

Accordingly, in a preferred embodiment, the 5-HT1 BR-stimulating agent used in the present invention is modified to comprise at least one charged chemical moiety, preferably positively charged. Notably, the positive charge can be retained at a wide range of pH, in particular at a physiological pH.

In other terms, such modified 5-HT1 BR-stimulating agents according to the invention are not capable of crossing the blood-brain barrier. Antidepressant agents and anti-migraine drugs modified in this manner are thus, respectively, anti-depressant disabled and antimigraine disabled.

Such chemical modifications have been extensively described in patent application WO 2007/148341, incorporated herein by reference, and can be performed so as to retain the 5-HT1 BR-stimulating activity of the compounds, while preventing them from crossing the blood-brain barrier.

The term "charged chemical moiety", "charged moiety", "charged chemical group" or "charged group", as used herein, refers to an atom or a group of atoms which forms a part of an organic molecule, and which is characterized by a positive or negative electrostatic charge.

By "positively charged chemical moiety", "positively charged moiety", "positively charged chemical group" or "positively charged group", it is thus meant herein a charged chemical moiety as defined above, which is characterized by a positive electrostatic charge. Compounds which include one or more positively charged moieties are molecular ions often referred to as molecular cations. A positively charged group of atoms has at least one electron less than the number of protons in these atoms. Positively charged chemical moieties include, without limitation, ammonium and sulfonium groups.

A positively charged group which retains its charge at physiological pH is a group that is not capable of participating in proton-exchange interactions at a pH range which is typical to the physiological environment in the body where the 5-HT1-BR stimulating agent is active. Typically, the physiological pH is about 7.4; therefore a positively charged group which retains its charge at physiological pH refers to a positively charged chemical group that stays ionized in a pH range of about 5-8. It is noted that even in the GI, where the pH level is extremely low in terms of physiological pH, the positively charged chemical moiety according to the invention remains positively charged, and hence modified 5-HT1-BR stimulating agents according to the present invention, are not adversely affected by the GI pH levels.

Still, yet, according to a further preferred embodiment, said positively charged chemical moiety is a quaternary ammonium group or a tertiary sulfonium group.

By "quaternary ammonium", it is meant herein a nitrogen atom which forms a part of a molecule (an amine) that is attached to four non-hydrogen substituents and thus is positively charged. The term "amine" describes a —NR'R" group where each of R' and R" is independently hydrogen, alkyl, cycloalkyl, heteroalicyclic, aryl or heteroaryl.

By "tertiary sulfonium group", it is meant herein a sulfur atom which forms a part of a molecule (a sulfonium) that is attached to three non-hydrogen substituents and thus is positively charged. The term "sulfonium" refers to a —S$^+$R'R", wherein R' and R" are each independently alkyl, cycloalkyl, heteroalicyclic, aryl or heteroaryl.

According to the invention, the term "alkyl group" refers to a linear or branched saturated aliphatic group. Preferably, the alkyl group has 1 to 20 carbon atoms, more preferably 1-10 carbon atoms, and even more preferably between 1-6 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. Examples of alkyl groups include, without limitation, methyl, ethyl, propyl, butyl, tert-butyl and isopropyl groups. The alkyl group can be further substituted. When substituted, the substituent can be, for example, an alkyl, an alkenyl, an alkynyl, a cycloalkyl, an aryl, a heteroaryl, a halide, a hydroxy, an alkoxy and a hydroxyalkyl. The term "alkyl", as used herein, further encompasses saturated or unsaturated hydrocarbon, hence this term further encompasses alkenyl and alkynyl.

The term "cycloalkyl" refers to an aliphatic monocyclic or bicyclic ring having 3 to 8 carbon atoms, and includes, without limitation cyclopropyl, cyclopentyl, cyclohexyl, etc.

The term "alkenyl" describes an unsaturated alkyl, as defined herein, having at least two carbon atoms and at least one carbon-carbon double bond, and which can be substituted by one or more substituents, as described above. The term "alkynyl" is an unsaturated alkyl having at least two carbon atoms and at least one carbon-carbon triple bond, and which can be substituted by one or more substituents, as described above.

The term "aryl" describes an all-carbon monocyclic or fused-ring polycyclic (i.e., rings which share adjacent pairs of carbon atoms) groups having a completely conjugated pi-electron system.

By "aryl or heteroaryl group", it is meant herein a mono- or polycyclic aromatic group comprising preferably between 4 and 15 carbon atoms, preferably between 5 and 10 carbon atoms. Examples of aryl groups include, without limitation, phenyl, naphtyl, etc. The aryl group according to the invention may be further substituted by one or more substituents, as described above. Heteroaryl groups typically comprise at least one heteroatom, such as nitrogen, oxygen, and sulfur—a heteroatom being any atom that is not carbon or hydrogen. Examples of heteroaryl groups include, without limitation, pyrrole, furane, thiophene, imidazole, oxazole, thiazole, pyrazole, pyridine, pyrimidine, quinoline, isoquinoline and purine. The heteroaryl group may be further substituted by one or more substituents, as described above; representative examples are thiadiazole, pyridine, pyrrole, oxazole, indole, purine and the like.

In a more preferred embodiment, said quaternary ammonium group has the formula (I)

—(NR$_1$R$_2$R$_3$)$^+$Z$^-$          (I)

wherein

Z is an organic or inorganic anion, such as NO$_3^-$, H$_2$PO$_4^{2-}$, Br—, HSO$_4^-$, CH$_3$SO$_3^-$, or tartaric acid anion; and R$_1$, R$_2$ and R$_3$ are each independently selected from the group consisting of alkyl, aryl and cycloalkyl.

Preferably, R$_1$, R$_2$ and R$_3$ are each an alkyl having from 1 to 4 carbon atoms, and more preferably, R$_1$, R$_2$ and R$_3$ are each methyl, resulting in the positively charged group, or the quaternary ammonium group —(NMe$_3$)$^+$.

In another preferred embodiment, said tertiary sulfonium group has the formula (II)

—(SR$_4$R$_5$)$^+$Z$^-$          (II)

wherein

Z is an organic or inorganic anion, such as NO$_3^-$, H$_2$PO$_4^2$, Br—, HSO$_4^-$, CH$_3$SO$_3^-$, or tartaric acid anion; and R$_4$ and R$_5$ are each independently selected from the group consisting of alkyl, aryl and cycloalkyl.

Preferably, R$_4$ and R$_5$ are each an alkyl having from 1 to 4 carbon atoms, and more preferably, R$_4$ and R$_5$ are each methyl, resulting in the positively charged group, or the sulfonium —(SMe$_2$)$^+$.

The positively charged group can be formed on the 5-HT1 BR-stimulating agent from an existing group which forms a part of the 5-HT1 BR-stimulating agent, namely, by turning a partially charged or uncharged group into a positively charged group, or by turning an existing positively charged group which can participate in proton-exchange interaction into one that cannot participate in such interaction, making it into an irreversible positive charge, or a permanent positive charge, thereby modifying the 5-HT1 BR-stimulating agent.

Alternatively, the positively charged group can be added to the 5-HT1 BR-stimulating agent by substituting one or more carbon atom with a positively charged group, e.g., by replacing a hydrogen atom or any other substituent with a quaternary ammonium or a tertiary sulfonium group.

Examples of preferred 5-HT1 BR-stimulating agents from which the compounds described herein can be derived include, without limitation, bisarylsulfanyl amines as described above such as vortioxetine, as well as fluoxetine, citalopram, alaproclate, dapoxetine, fluvoxamine, paroxetine, sertraline, venlafaxine, zimelidine, etoperidone, densvalafaxine, duloxetine, minalcipran, nefazodone, venlafaxine, brasofensine, tesofensine and nomifensine, preferably vortioxetine, fluoxetine, citalopram, alaproclate, dapoxetine, fluvoxamine, paroxetine, sertraline, venlafaxine and zimelidine. Indeed, all these agents already comprise at least one amine group, which can be readily converted into a quaternary ammonium, i.e. a positively charged group as defined above. In particular, said agents can be modified to comprise at least one quaternary ammonium group of formula (I) as described above.

An example of derivative of citalopram that comprises such a quaternary ammonium group is n-methyl-citalopram (NMC), of which the synthesis is fully detailed in patent application WO2007/128341.

Bisarylsulfanyl amines of formula (A) are also herein particularly advantageous as they comprise not only an amine group, but also a sulfur group, which can be readily converted into a quaternary ammonium group and/or into a tertiary sulfonium group, respectively. Positively charged moieties can also be attached to the carbon atom(s) of the piperazine group of said compounds.

Particularly preferred derivatives of said bisarylsulfanyl amines are compounds of formula (B) as follows:

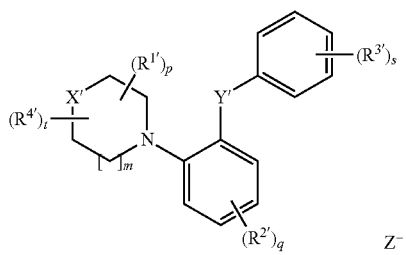

wherein
- Z is an organic or inorganic anion as defined above, such as $NO_3^-$, $H_2PO_4^{2-}$, Br—, $HSO_4^-$, $CH_3SO_3^-$, or tartaric acid anion, or a mixture of organic or inorganic anions, whose global charge is such that the compound of formula (B) is neutral;
- $R^{1'}$, $R^{2'}$, $R^{3'}$, m, p, q and s are as defined above, wherein $R^{3'}$ can optionally be a $C_{1-6}$-alk(en/yn)yloxy group substituted by an ammonium or sulfonium group as defined above, preferably $R^{3'}$ is choline;
- t is 0, 1, 2, 3, 4, 5, 6, 7 or 8, preferably 0 or 1, more preferably 0, with the proviso that t+p≤8;
- each $R^{4'}$ is at least one charged chemical moiety, identical or different, preferably positively charged, as defined above, such as a sulfonium or an ammonium group;
- X' is selected from the group consisting of:
  - —$(NR^{5'}R^{6'})^+$— wherein
    - $R^{5'}$ and $R^{6'}$ are each independently selected from the group represented by hydrogen, alkyl, aryl and cycloalkyl as defined herein, preferably by an hydrogen, a $C_{1-6}$-alkyl, and a $C_{3-8}$-cycloalkyl; or
    - $R^{5'}R^{6'}$ form together with the nitrogen to which they are attached a cycloheteroalkyl, preferably a 3-8-membered cycloheteroalkyl, more preferably a 3-6-membered cycloheteroalkyl;
  - —NH—;
  - —$NR^{7'}$— wherein $R^{7'}$ is a $C_{1-6}$-alkyl;
  - —$N^+(O^-)R^{8'}$— wherein $R^{8'}$ is a $C_{1-6}$-alkyl;
  - —$NC(O)R^{9'}$— wherein $R^{9'}$ is an amino acid, said amino-acid being preferably positively charged such as histidine, arginine or lysine, or an amino acid derivative, said derivative being preferably positively charged such as choline or carnitine, or a $C_{1-6}$-alkyl phosphonium;
- Y' is selected from the group consisting of:
  - —S—;
  - —$(SR^{10'})^+$— wherein $R^{10'}$ is selected from the group represented by hydrogen, alkyl, aryl and cycloalkyl as defined herein, preferably is a $C_{1-6}$-alkyl; and
  - —$S^+(O)^-$—.

The skilled person in the art would readily understand that the anions Z are present to counterbalance the positive charges on the molecule. Accordingly, compounds of formula (B) comprise as many anions Z as necessary to neutralize the positive charges of the molecule. One skilled practitioner would further understand that when p>0 and t>0, $R^{1'}$ and $R^{4'}$ are attached to any of the carbon atoms of the heterocyclic ring, albeit to different carbons.

In a preferred embodiment, only one of X', Y', $R^{4'}$ (when t>0) and $R^{3'}$ (when substituted by an ammonium or sulfonium group) is a positively charged chemical moiety.

Preferred embodiments regarding $R^{1'}$, $R^{2'}$, $R^{3'}$, m, p, q and s are as defined above.

In a preferred embodiment of the invention, the 5-HT1 BR-stimulating agent from which the compounds described herein are derived, to notably preferably comprise a charged chemical moiety, is selected from the group consisting of atypical antidepressants, such as bisarylsulfanyl amines as defined above, and SRIs, in particular SSRIs.

More preferably, the 5-HT1 BR-stimulating agent to be modified is the atypical antidepressant vortioxetine or the SSRI fluoxetine. Most preferably, the 5-HT1 BR-stimulating agent to be modified is vortioxetine.

For example, vortioxetine can be chemically modified, as follows:

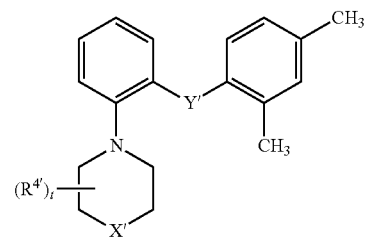

wherein Z, t, $R^{4'}$, X' and Y' are as defined above. More preferably, t=0.

Particularly preferred salts, derivatives and/or analogs of vortioxetine, which comprise at least one charged chemical moiety, preferably positively charged, are selected from the group consisting of:

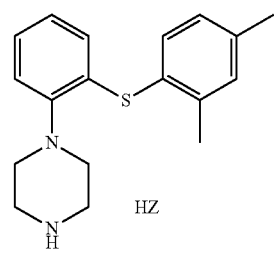 [SMILES: Cc1ccc(Sc2ccccc2N2CCNCC2)c(C)c1]

wherein HZ is preferably $HNO_3$, $H_3PO_4$, HBr, $H_2SO_4$, $CH_3SO_3H$, or tartaric acid (salts of vortioxetine);

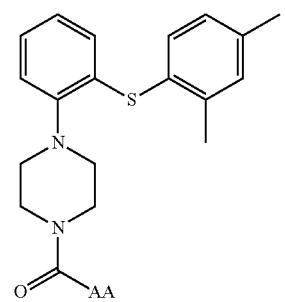

wherein AA is an amino acid, preferably

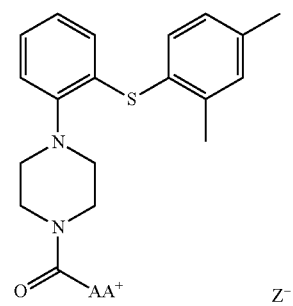

wherein AA+ is a positively charged amino acid such as histidine, arginine or lysine;

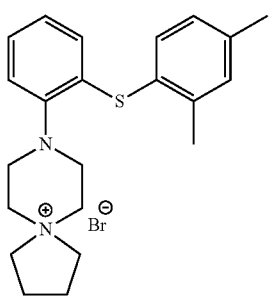
(pyrrolidinium-vortioxetine)
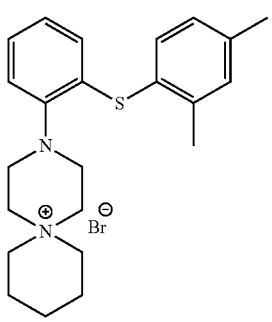
(pyperazinium-vortioxetine)
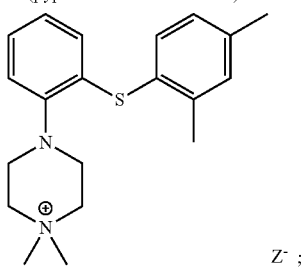
(dimethylammonium-vortioxetine)
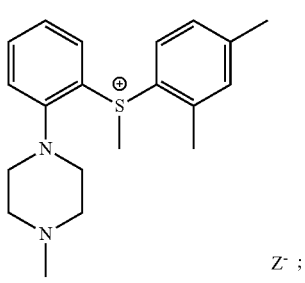
(sulfonium-vortioxetine)
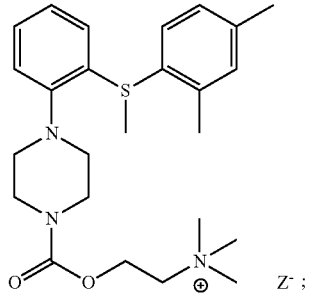
(choline-vortioxetine)
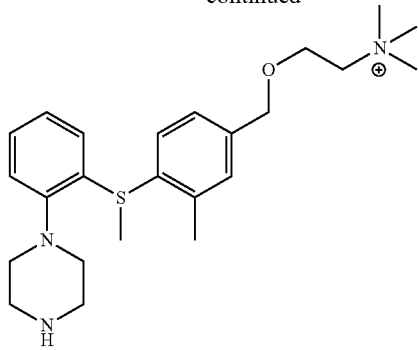
(benzyle-choline-vortioxetine)
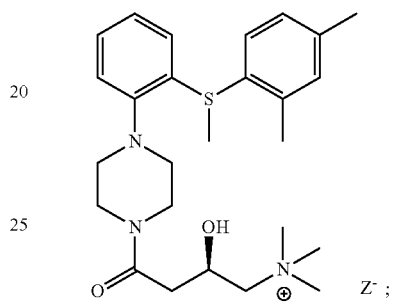
(L-carnitine-vortioxetine)
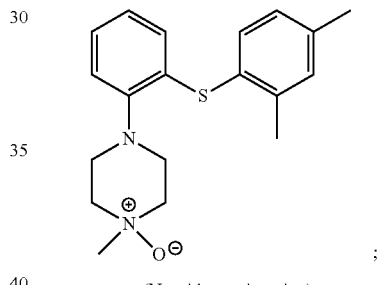
(N-oxide-vortioxetine)
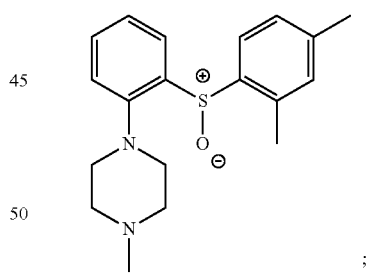
(sulfoxide-vortioxetine)
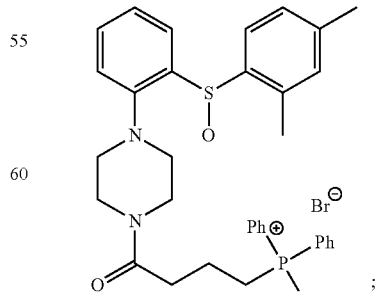
(phosphonium-vortioxetine)
; and

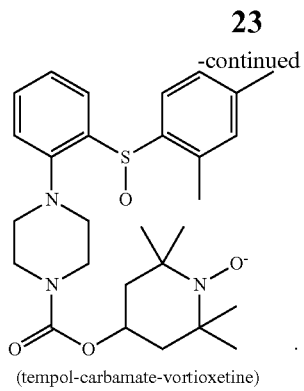

(tempol-carbamate-vortioxetine)

Preferably, said salts, derivatives and/or analogs of vortioxetine, which comprise at least one charged chemical moiety, preferably positively charged, are selected from the group consisting of:
- salts of vortioxetine as described above;
- vortioxetine coupled to a positively charged amino acid (preferably at least one) such as histidine, arginine or lysine, as described above;
- pyrrolidinium-vortioxetine;
- pyperazinium-vortioxetine;
- dimethylammonium-vortioxetine;
- sulfonium-vortioxetine;
- N-oxide-vortioxetine;
- sulfoxide-vortioxetine;
- phosphonium-vortioxetine; and
- tempol-carbamate-vortioxetine.

More preferably, said salts, derivatives and/or analogs of vortioxetine, which comprise at least one positively charged chemical moiety, are selected from the group consisting of:
- salts of vortioxetine as described above;
- vortioxetine coupled to a positively charged amino acid (preferably at least one) such as histidine, arginine or lysine, as described above;
- pyrrolidinium-vortioxetine;
- pyperazinium-vortioxetine;
- dimethylammonium-vortioxetine;
- sulfonium-vortioxetine;
- N-oxide-vortioxetine;
- sulfoxide-vortioxetine; and
- phosphonium-vortioxetine.

Yet, even more preferably, said salts, derivatives and/or analogs of vortioxetine, which comprise at least one positively charged chemical moiety, are selected from the group consisting of:
- salts of vortioxetine as described above;
- vortioxetine coupled to a positively charged amino acid (preferably at least one) such as histidine, arginine or lysine, as described above;
- pyrrolidinium-vortioxetine;
- pyperazinium-vortioxetine;
- dimethylammonium-vortioxetine;
- sulfonium-vortioxetine; and
- phosphonium-vortioxetine.

Still, even more preferably, said positively charged vortioxetine is selected from the group consisting of histidine-vortioxetine and pyrrolidinium-vortioxetine.

The above compounds can be prepared according to conventional methods in the art. Such methods are described in further details below.

For example, in order to synthetize pyrrolidinium-vortioxetine or pyperazinium-vortioxetine, one skilled person in the art can proceed as follows:

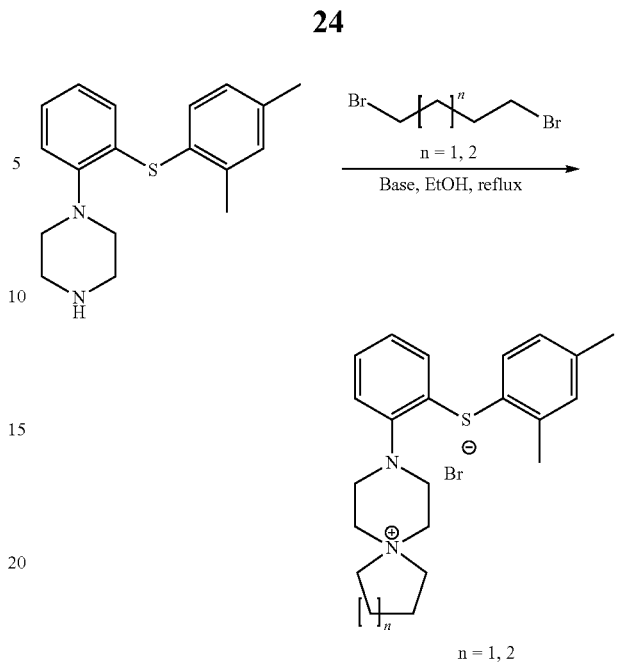

More particularly, for pyrrolidinium (n=1) formation on 4-arylpiperazine, the reaction can be performed using either $K_2CO_3$, ethanol (EtOH) and reflux for 10 h (Mokrosz et al., 1992, incorporated herein by reference), or $K_2CO_3$, acetone and reflux for 15 h (see WO 2004/9914A1, incorporated herein by reference).

Still, for example, in order to synthetize dimethylammonium-vortioxetine, one skilled person in the art can proceed as follows:

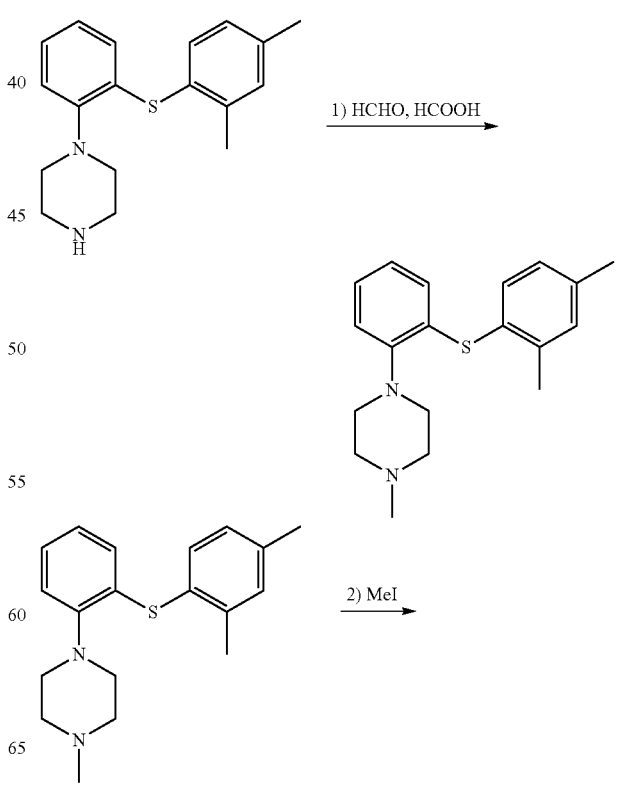

-continued

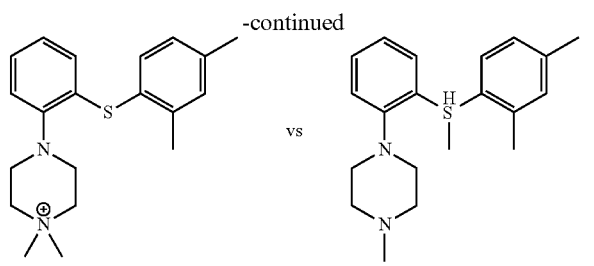

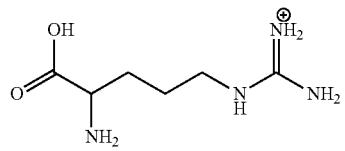

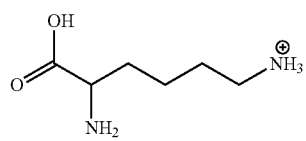

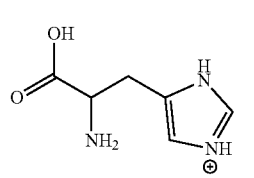

More particularly, for 4-arylpiperazine dimethylation, one can refer to Romanelli et al. (2001) (incorporated herein by reference), the first step being an Eschweiler-clarke reaction, and the second step being a methylation.

As another illustrative example, in order to synthetize amino acid derivatives of vortioxetine, choline-vortioxetine and carnitine-vortioxetine, one skilled person in the art can proceed as follows:

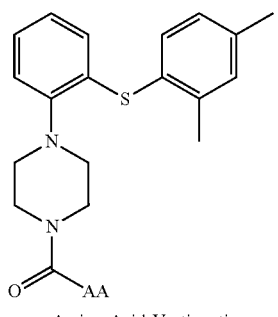
Amino-Acid-Vortioxetine

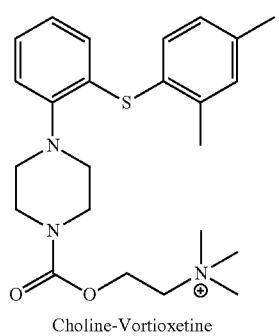
Choline-Vortioxetine

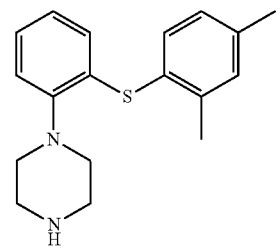

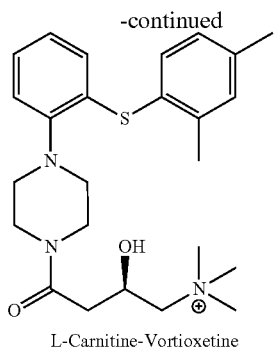
L-Carnitine-Vortioxetine

More particularly, for amide formation on the carnitine, the reaction can be performed on either acylhydrazine using pyridine, ethylene dichloride (EDC), dimethylformamide (DMF), and ethanol (EtOH) (Kuroda et al., 1996, incorporated herein by reference), or on primary amine using pyridine, ethylene dichloride (EDC), methanol (MeOH) and acetonitrile (CH$_3$CN) (Nakaya et al., 2001, incorporated herein by reference).

As another illustrative example, in order to synthetize phosphonium-vortioxetine, one skilled person in the art can proceed as follows:

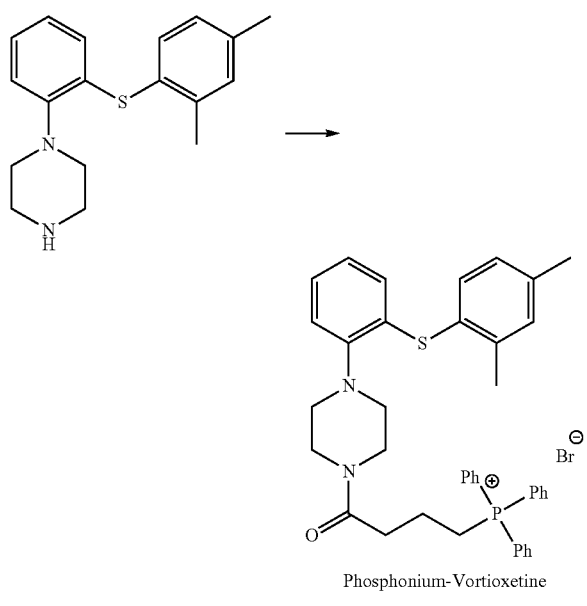

Phosphonium-Vortioxetine

As another illustrative example, in order to synthetize N-oxide-vortioxetine, one skilled person in the art can proceed as follows:

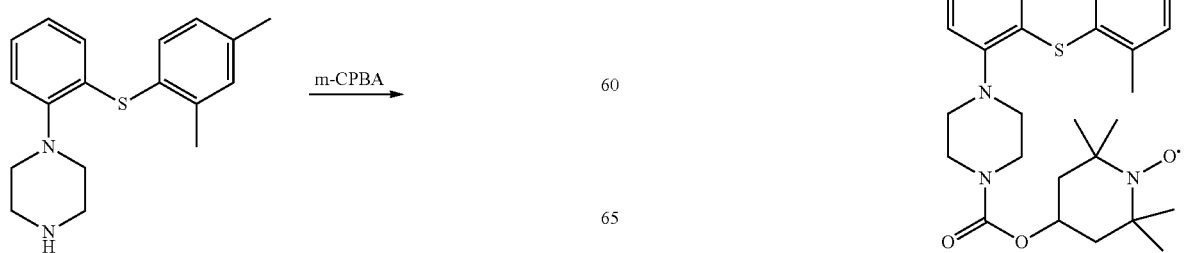

More particularly, for N-oxidation of 4-aryl-piperazines, the reaction can be performed using meta-chloroperoxybenzoic acid (m-CPBA) and CH$_2$Cl$_2$ at 20-45° C. (see US 2008/153812A1, WO 2011/162515A2 or WO 2004/104007A1, incorporated herein by reference).

As another illustrative example, in order to synthetize tempol-carbamate-vortioxetine, one skilled person in the art can proceed as follows:

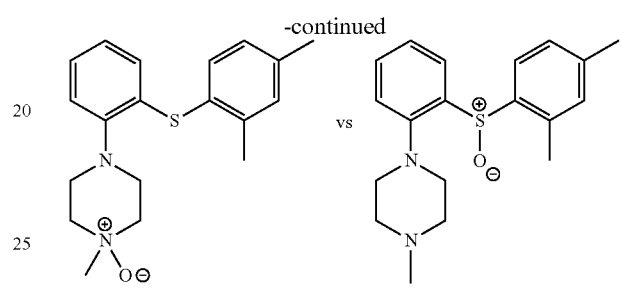

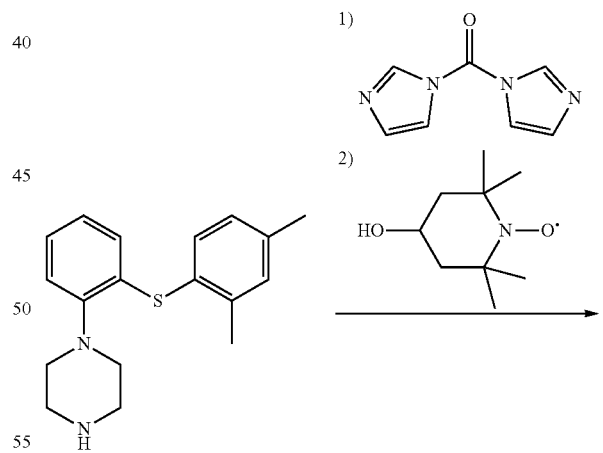

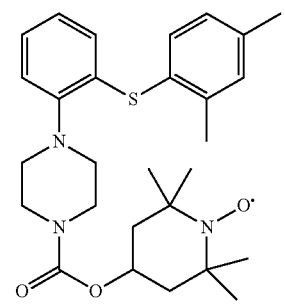

As another illustrative example, in order to synthetize benzyl-choline-vortioxetine, one skilled person in the art can proceed as follows:

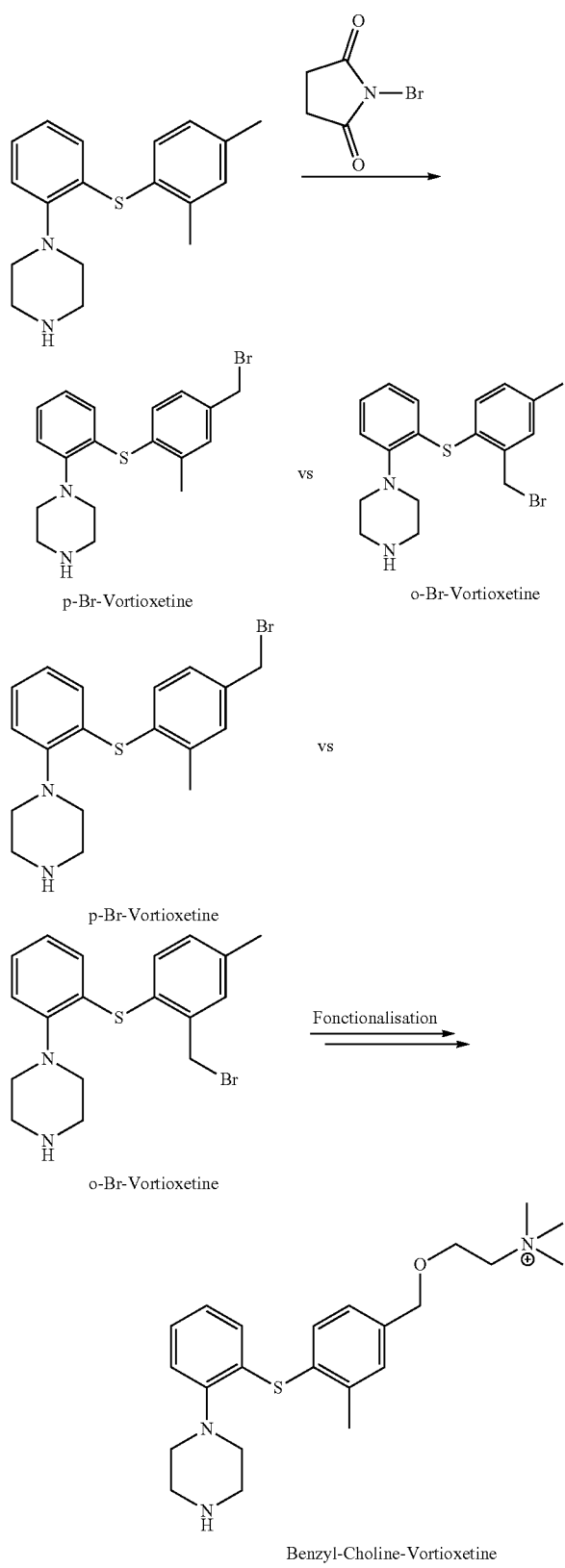

More particularly, for benzylic position bromation, the reaction can be performed using either N-bromosuccinimide, azobisisobutyronitrile (AlBN) and tetrachloromethane (CCl$_4$) (see US 2010/4159A1, incorporated herein by reference), or N-bromosuccinimide, meta-chloroperoxybenzoic acid (m-CPBA) and tetrachloromethane (CCl$_4$) (see Farmaco, 1989, 44, from p. 683, incorporated herein by reference).

The 5-hydroxytryptamine 1B receptor (5-HT1 BR)-stimulating agent as defined above can be used for therapeutic purposes, either in a pharmaceutical composition which may comprise additional active agent(s), or in a combined preparation which may be administered simultaneously, separately or sequentially to a subject in need thereof.

It is thus a further aspect of the invention to provide the 5-hydroxytryptamine 1B receptor (5-HT1 BR)-stimulating agent as defined above, for use, preferably as an adjuvant, in a therapeutic method for delaying the progression of natural or pathological loss and/or damage and/or impairment of skeletal muscle tissue(s).

More precisely, the invention relates to the use of a 5-hydroxytryptamine 16 receptor (5-HT1 BR)-stimulating agent as described herein, for manufacturing a medicament intended to delay the progression of natural or pathological loss and/or damage and/or impairment of skeletal muscle tissue(s) in a subject in need thereof.

In other words, the invention relates to a therapeutic method for delaying the progression of natural or pathological loss and/or damage and/or impairment of skeletal muscle tissue(s) in a subject in need thereof, comprising the step of administering an effective amount of a 5-hydroxytryptamine 1B receptor (5-HT1 BR)-stimulating agent as described herein, to said subject.

Yet, in another aspect, the invention relates to a pharmaceutical composition for use as:
  i) a promoter of satellite cells self-renewal and/or differentiation; and/or
  ii) an agent preventing and/or inhibiting the satellite cells pool exhaustion, wherein said composition comprises at least one 5-hydroxytryptamine 1B receptor (5-HT1 BR)-stimulating agent as defined above and at least one pharmaceutically acceptable excipient.

More precisely, the invention relates to the use of said pharmaceutical composition, for manufacturing a medicament to i) promote satellite cells self-renewal and/or differentiation and/or ii) prevent and/or inhibit the satellite cells pool exhaustion.

In other words, the invention relates to a method for i) promoting satellite cells self-renewal and/or differentiation and/or ii) preventing and/or inhibiting the satellite cells pool exhaustion, comprising the step of administering an effective amount of said composition, to a subject in need thereof.

By "pharmaceutically acceptable excipient", it is meant herein a compound of pharmaceutical grade which improves the delivery, stability or bioavailability of an active agent, and can be metabolized by, and is non-toxic to, a subject to whom it is administered. Preferred excipients according to the invention include any of the excipients commonly used in pharmaceutical products, such as, for example, microcrystalline cellulose, lactose, starch, and soybean powder.

According to a preferred embodiment, said pharmaceutical composition further comprises at least one active agent delaying, preventing or treating a natural or pathological loss and/or damage and/or impairment of skeletal muscle tissue(s) (albeit with a possible different efficacy than the 5-HT1 BR-stimulating agent according to the invention) and/or increasing or potentiating the action of 5-HT1 BR-stimulating agent(s) (i.e. increasing or potentiating the stimulation of the activity of the 5-hydroxytryptamine 1B receptor that is exerted by the 5-HT1 BR-stimulating agent). Said agent can be a therapeutic agent known for example for delaying, preventing or treating a natural or pathological loss and/or damage and/or impairment of skeletal muscle tissue(s).

Such active agents are well-known to the skilled person in the art, and include, without limitation, satellite cells, mesenchymal stem cells, hematopoietic stem cells, pericytes, mesangioblasts, the above-mentioned cells being natural or genetically modified, anti-inflammatory agents such as corticosteroids and NSAIDs (nonsteroidal anti-inflammatory drugs), myotrophic agents such as myostatins, immunotherapeutic agents, antibodies, genetic elements such as CRISPR/Cas9, and combinations thereof, preferably satellite cells, genetically modified satellite cells, mesenchymal stem cells, hematopoietic stem cells, pericytes, mesangioblasts and combinations thereof. Pindolol and (S)-(−)-pindolol are also suitable active agents as these are known for potentiating the action of antidepressants. Indeed, the combined preparation of the 5-HT1 BR-stimulating agent according to the invention and of the above-mentioned active agents can significantly improve the promotion of satellite cells self-renewal and/or differentiation; and/or the prevention and/or inhibition of the satellite cells pool exhaustion, thereby improving muscle regeneration.

It is within the skill of ordinary person in the art to select the appropriate combination of 5-HT1 BR-stimulating agent and active agent delaying, preventing or treating a natural or pathological loss and/or damage and/or impairment of skeletal muscle tissue(s), and/or increasing or potentiating the action of 5-HT1 BR-stimulating agent(s), among the above active agents, for the purposes of the invention.

The pharmaceutical composition of the invention may preferably be in a form suitable for the purposes of the invention. For example, said composition may be in a form suitable for parenteral, oral or topical administration, such as a liquid suspension, a solid dosage form (granules, pills, capsules or tablets), or a paste or gel. The term parenteral as used herein includes subcutaneous injection, intravenous, or intramuscular injection. For example, the pharmaceutical composition can be in a form suitable for intramuscular administration.

The above composition can more particularly be used to delay the progression of natural or pathological loss and/or damage and/or impairment of skeletal muscle tissue(s).

Thus, in a particular embodiment, the invention provides the pharmaceutical composition as defined above, for use in a therapeutic method for delaying the progression of natural or pathological loss and/or damage and/or impairment of skeletal muscle tissue(s).

More precisely, the invention relates to the use of said pharmaceutical composition, for manufacturing a medicament intended to delay the progression of natural or pathological loss and/or damage and/or impairment of skeletal muscle tissue(s) in a subject in need thereof.

In other words, the invention relates to a therapeutic method for delaying the progression of natural or pathological loss and/or damage and/or impairment of skeletal muscle tissue(s) in a subject in need thereof, comprising the step of administering an effective amount of said pharmaceutical composition to said subject.

As indicated above, it is particularly advantageous to combine a 5-hydroxytryptamine 1B receptor (5-HT1 BR)-stimulating agent according to the invention with an active agent delaying, preventing or treating a natural or pathological loss and/or damage and/or impairment of skeletal muscle tissue(s) and/or increasing or potentiating the action of 5-HT1 BR-stimulating agents conventionally used in the art.

It is thus another aspect of the invention to provide a 5-hydroxytryptamine 1B receptor (5-HT1 BR)-stimulating agent and an active agent delaying, preventing or treating a natural or pathological loss and/or damage and/or impairment of skeletal muscle tissue(s), and/or increasing or potentiating the action of 5-HT1 BR-stimulating agents, as a combined preparation for simultaneous, separate or sequential administration in a subject in need thereof.

Preferred active agents according to the invention that delay, prevent or treat a natural or pathological loss and/or damage and/or impairment of skeletal muscle tissue(s) and/or increasing or potentiating the action of 5-HT1 BR-stimulating agents are as described above.

The dose and scheme of administration of the 5-hydroxytryptamine 1B receptor (5-HT1 BR)-stimulating agent or of the pharmaceutical composition according to the invention can be adapted by the skilled person in the art depending on the age, weight and severity of the symptoms of the subject to be treated.

Accordingly, in another aspect, the 5-hydroxytryptamine 1B receptor (5-HT1 BR) or the composition according to the invention can be administered once a day, preferably for a period of about 6 weeks (in particular for slow-acting 5-HT1 BR-stimulating agents such as fluoxetine) or for a period of about 12 days (in particular for fast-acting 5-HT1 BR-stimulating agents such as vortioxetine).

Yet, in a preferred embodiment, the 5-hydroxytryptamine 1B receptor (5-HT1 BR)-stimulating agent or the composition according the invention is administered at a dosage comprised between about 5 mg/kg and about 30 mg/kg, preferably between about 10 mg/kg and about 25 mg/kg, more preferably between about 15 mg/kg and about 20 mg/kg and preferably at 18 mg/kg.

In another aspect, the 5-hydroxytryptamine 1B receptor-stimulating agent according to the invention may be used for drug screening purposes. In particular, novel drug assays may be provided, which identify therapeutics efficiently interfering with satellite cells self-renewal and/or differentiation, and/or with the replenishment of the in vivo satellite cells pool.

In this aspect, the invention more particularly relates to an in vitro screening method for identifying an agent or combination of agents promoting satellite cells self-renewal and/or differentiation; and/or preventing and/or inhibiting satellite cells pool exhaustion, comprising the steps of:
 a) contacting isolated satellite cells with a candidate agent or combination of candidate agents;
 b) assessing the cell phenotype of said cells;
 c) comparing the cell phenotype in step b) to the phenotype of satellite cells in the absence of said agent or combination of agents, and/or to the phenotype of satellite cells contacted with a 5-hydroxytryptamine 1B receptor (5-HT1 BR)-stimulating agent, as described above.

Preferably, the isolated satellite cells of step a) are quiescent satellite cells.

The above method may optionally further comprise the step d) of determining whether the candidate agent or combination of agents is promoting satellite cells self-renewal and/or differentiation; and/or preventing and/or inhibiting satellite cells pool exhaustion, based upon the comparison in step c).

The cell phenotype can be assessed by analyzing the expression of cell markers that are characteristic of quiescent, self-renewing and/or differentiating satellite cells, as described above.

The present invention will be better understood in the light of the following detailed description of experiments, including examples. Nevertheless, the skilled artisan will appreciate that this detailed description is not limitative and that various modifications, substitutions, omissions, and changes may be made without departing from the scope of the invention.

Using immunostainings and FACS cell sorting in Figures (p) to (v):

(p) Number of Pax7GFP expressing cells per digested TA (expressed as an absolute number) counted by FACS. (q) Representative FACS profile of digested TA of TgPax7nGFP mouse. (r) Cumulative number of BrdU+ SC.Tg:Pax7nGFP mice (n=3 per time point) received BrdU in drinking water together with fluoxetine or placebo from the beginning of the treatment to the end. TA muscle was digested and cells were isolated by FACS, spined on a slide and immuno-stained against BrdU. (s) Percentage of BrdU+ cells in Tg:Pax7nGFP mice (n=3 per time point). Tg:Pax7nGFP mice received the fluoxetine treatment per os and were injected with BrdU twice (12 h and 4 h before death) TA muscle was digested and cells were isolated by FACS, spined on a slide and immuno-stained against BrdU. (t) Number of vessels per $mm^2$ counted on histological section using CD31 immuno-labeling in placebo and fluoxetine treated animals. (u-v) Representative histological sections of laminin and CD31+ immunostaining in placebo (u) and fluoxetine (v) treated mice For Figures (a) to (o): n=8 mice used per condition, except for the in vivo experiments cells where n=6. Data are represented as mean±s.d. *P<0.05; P<0.01; *P<0.001. Scale bar represents 100 μm.

For Figures (p) to (v): n=7 mice used per condition, except for BrdU experiments n=3 per time point. Data are represented as mean±s.d. **P<0.01. Scale bar represents 100 μm.

Figure 3:
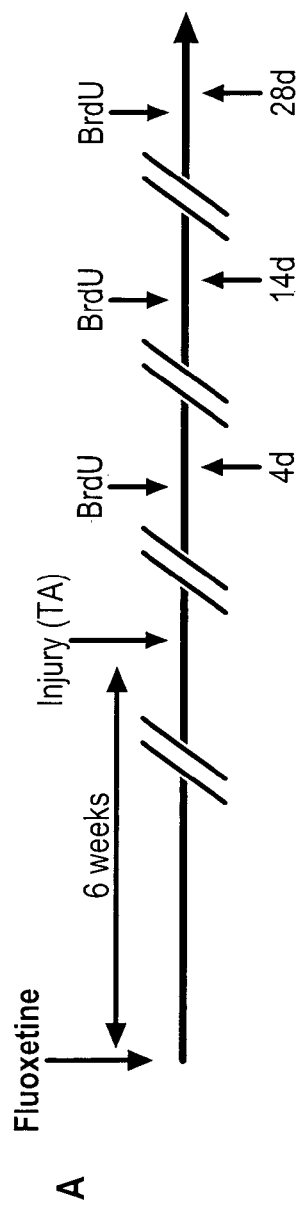
Figure 3:
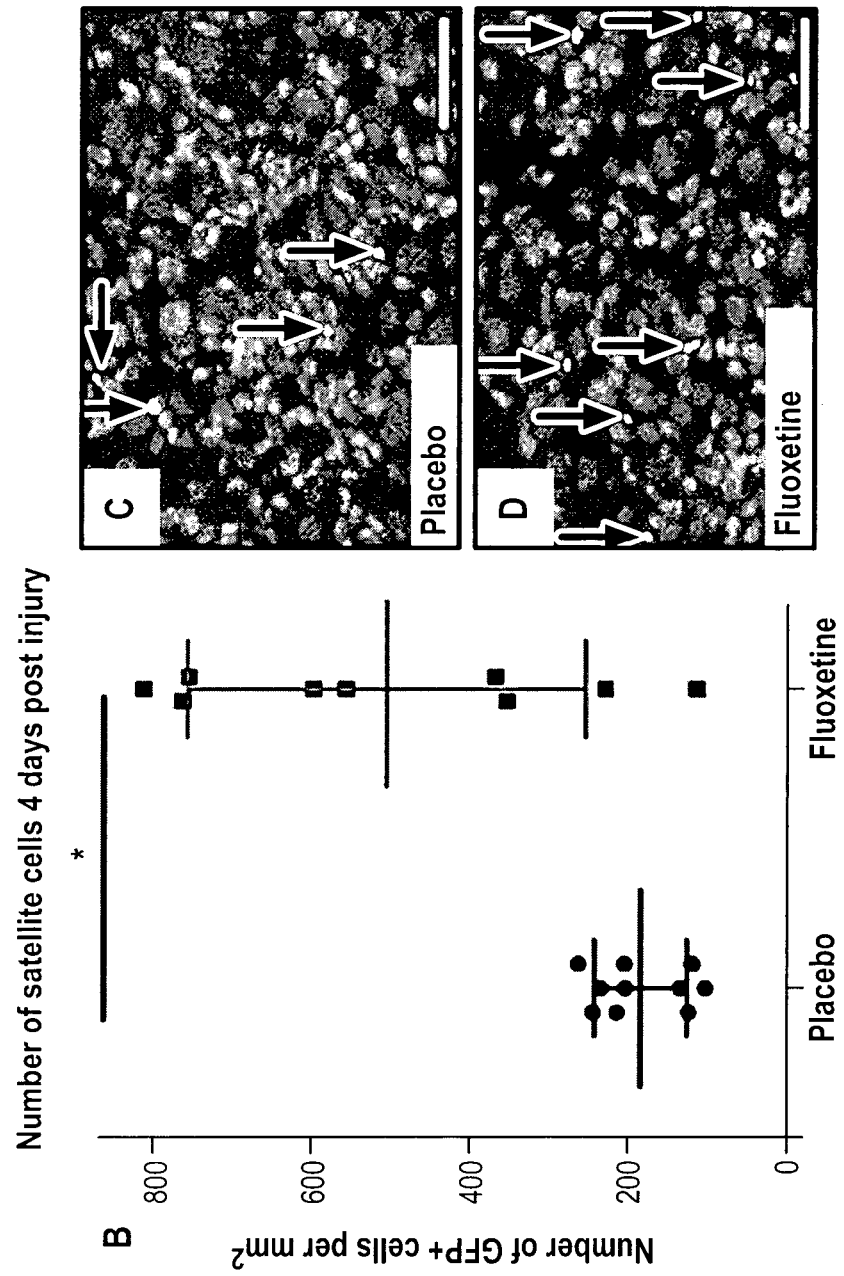
Figure 3:
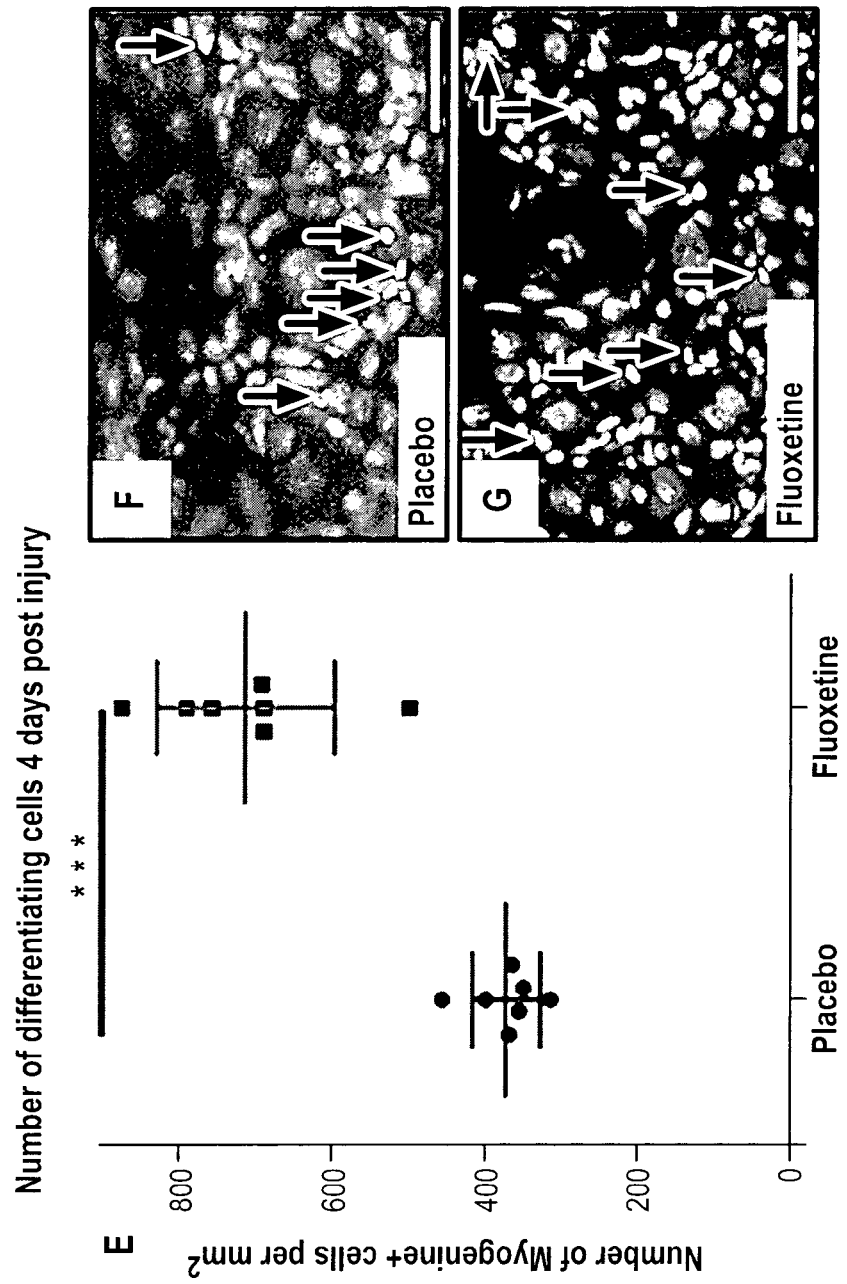
Figure 3:
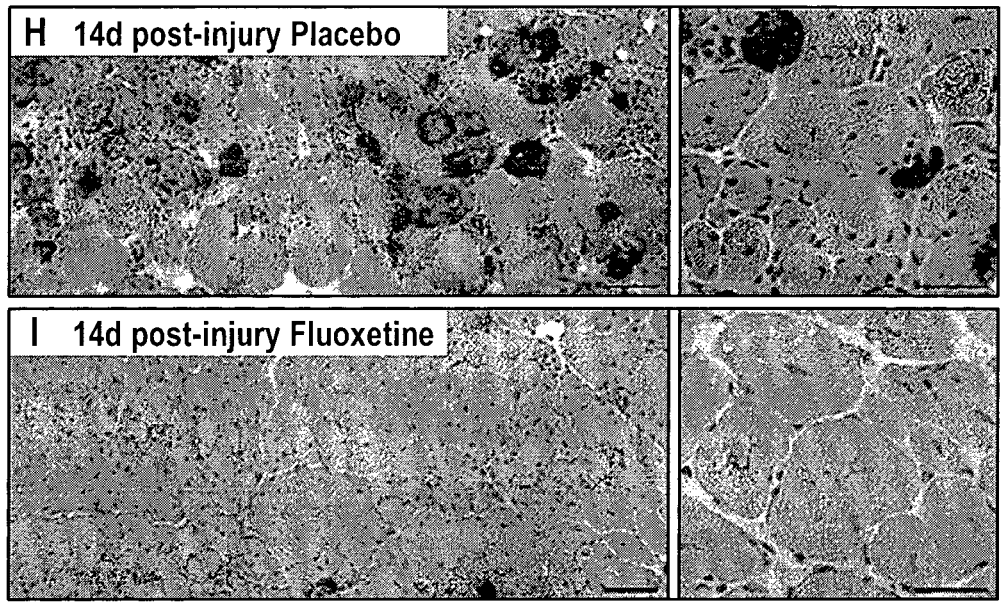
Figure 3:
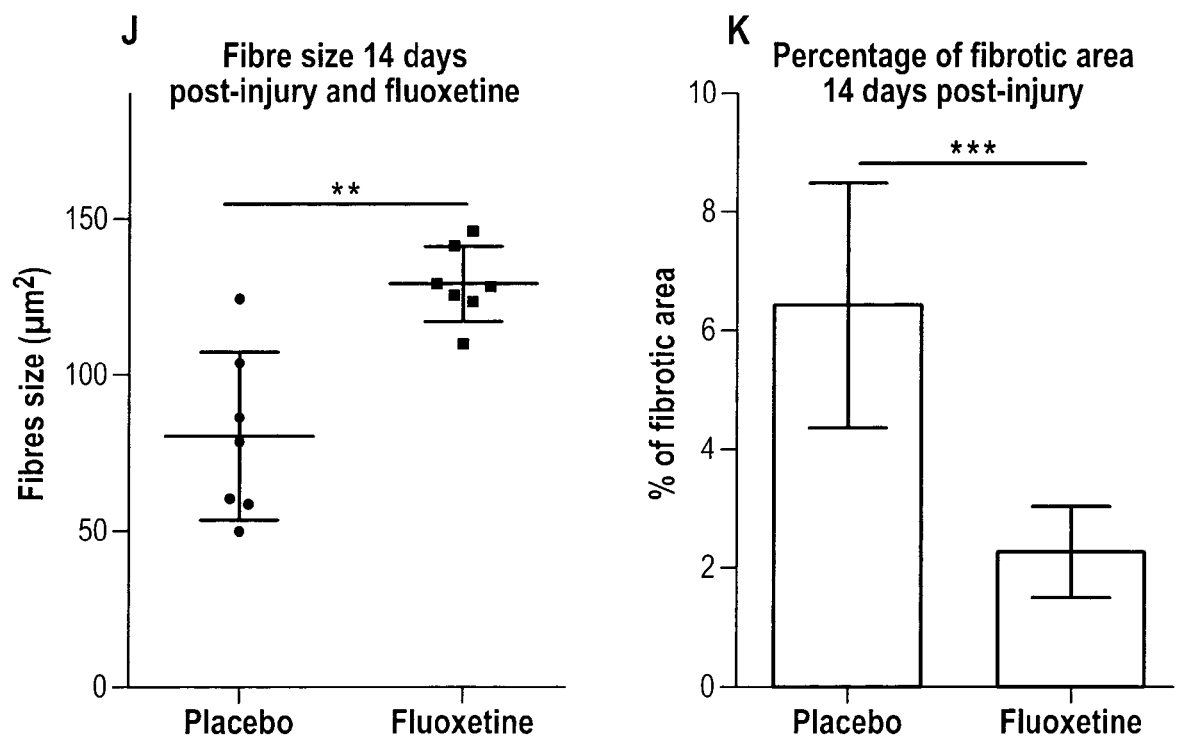
Figure 3:
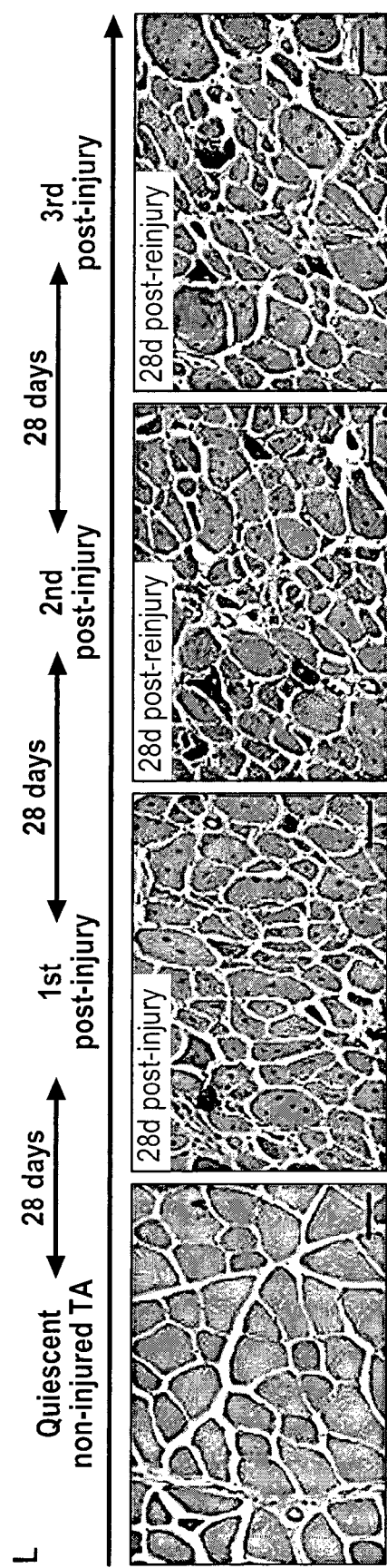

FIG. 3. Fluoxetine improves muscle regeneration by increasing the number of satellite cells (a) Schematic representation of fluoxetine delivery, muscle injuries, BrdU injections and sacrifice time points. (b) Number of Pax7GFP+ cells per $mm^2$ 4 days post-injury. (c-d) Immunostaining of Pax7GFP+ cells on section after placebo (c) and fluoxetine (d) treatment. (e) Number of differentiating (Myogenin+) cells 4 days post-injury. (f-g) Representative pictures of Myogenin and GFP cells in placebo (f) and fluoxetine (g) treated animals. (h-i) Haematoxylin and eosin staining of cryo-sectioned TA 14 days post-injury in the placebo (h) and fluoxetine (i) treated animals. (j) Fibre size in $μm^2$ in placebo and fluoxetine 14 days post-injury. (k) Percentage of fibrotic area 14 days post injury in placebo and fluoxetine treated mice. (l) Haematoxylin and eosin staining of cryo-sectioned TA after serial injuries. n=7 mice used per condition, except for the count of GFP+ cells where n=9. Data are represented as mean±s.d. *P<0.05; P<0.01; *P<0.001. Scale bar represents 100 μm.

Figure 4:
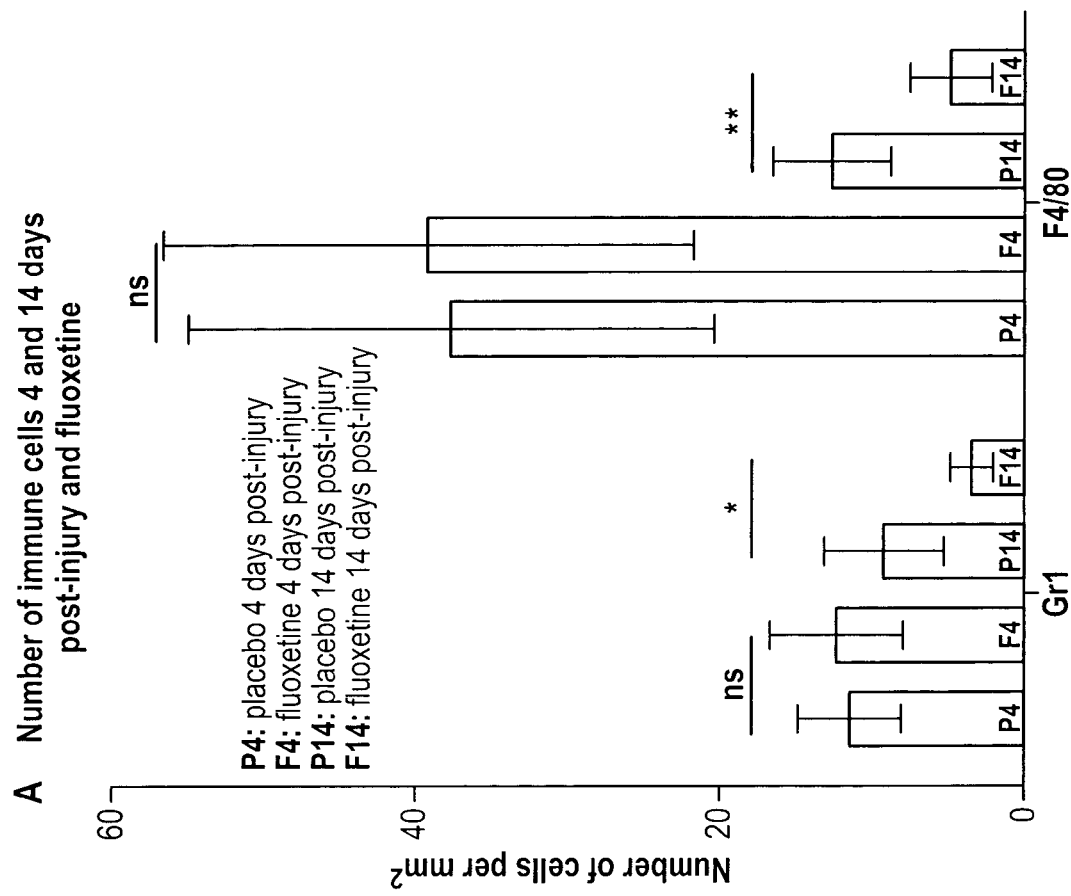
Figure 4:
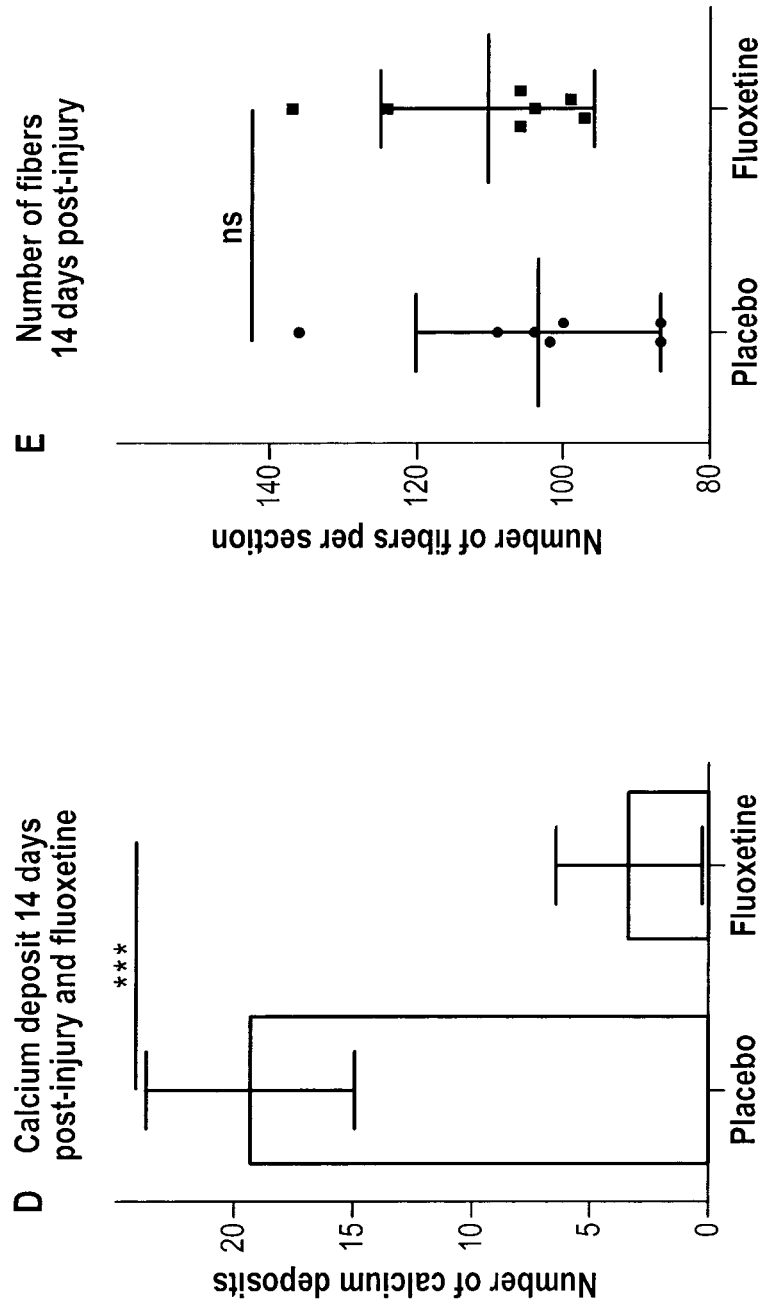
Figure 4:
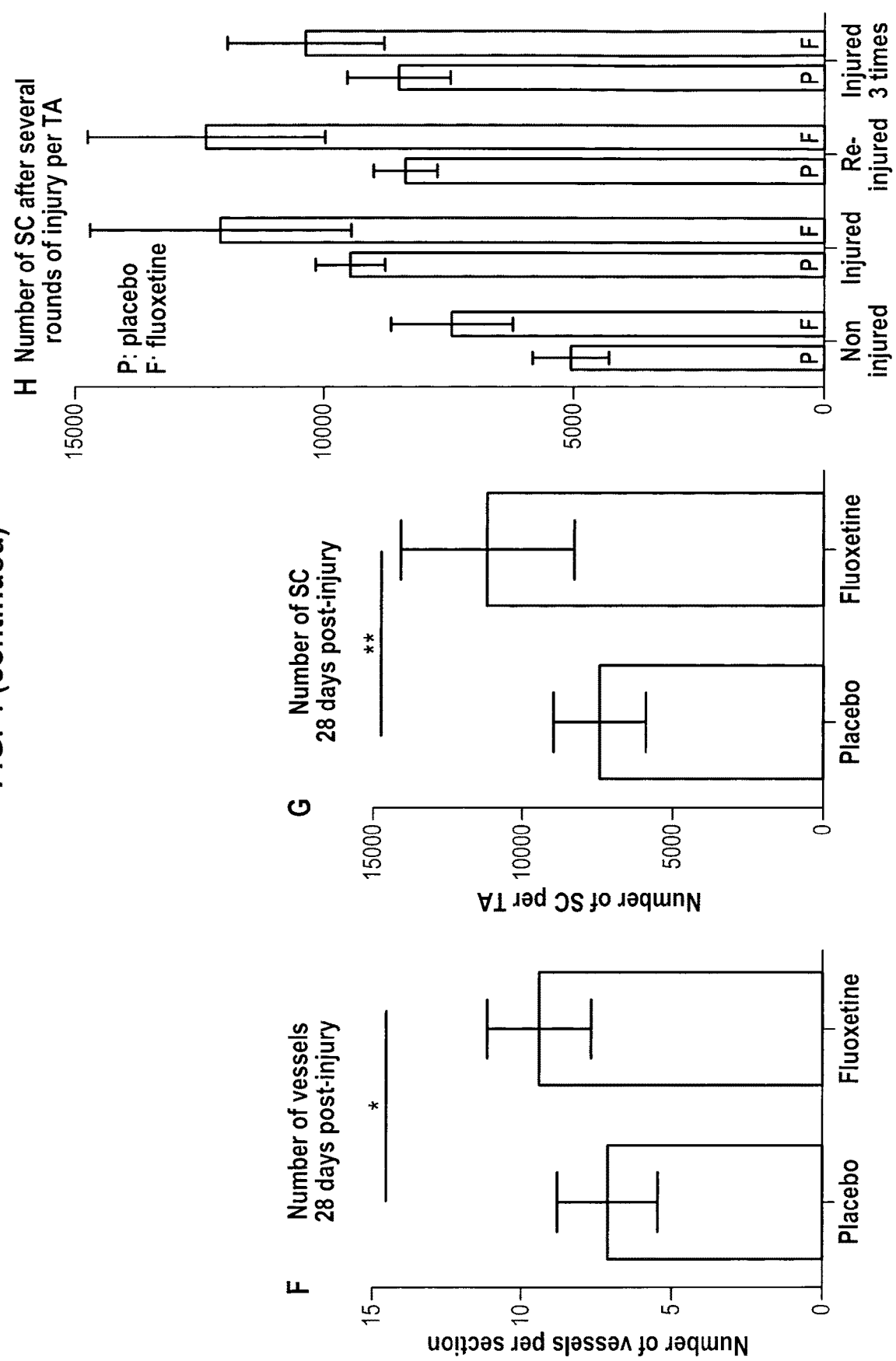
Figure 4:
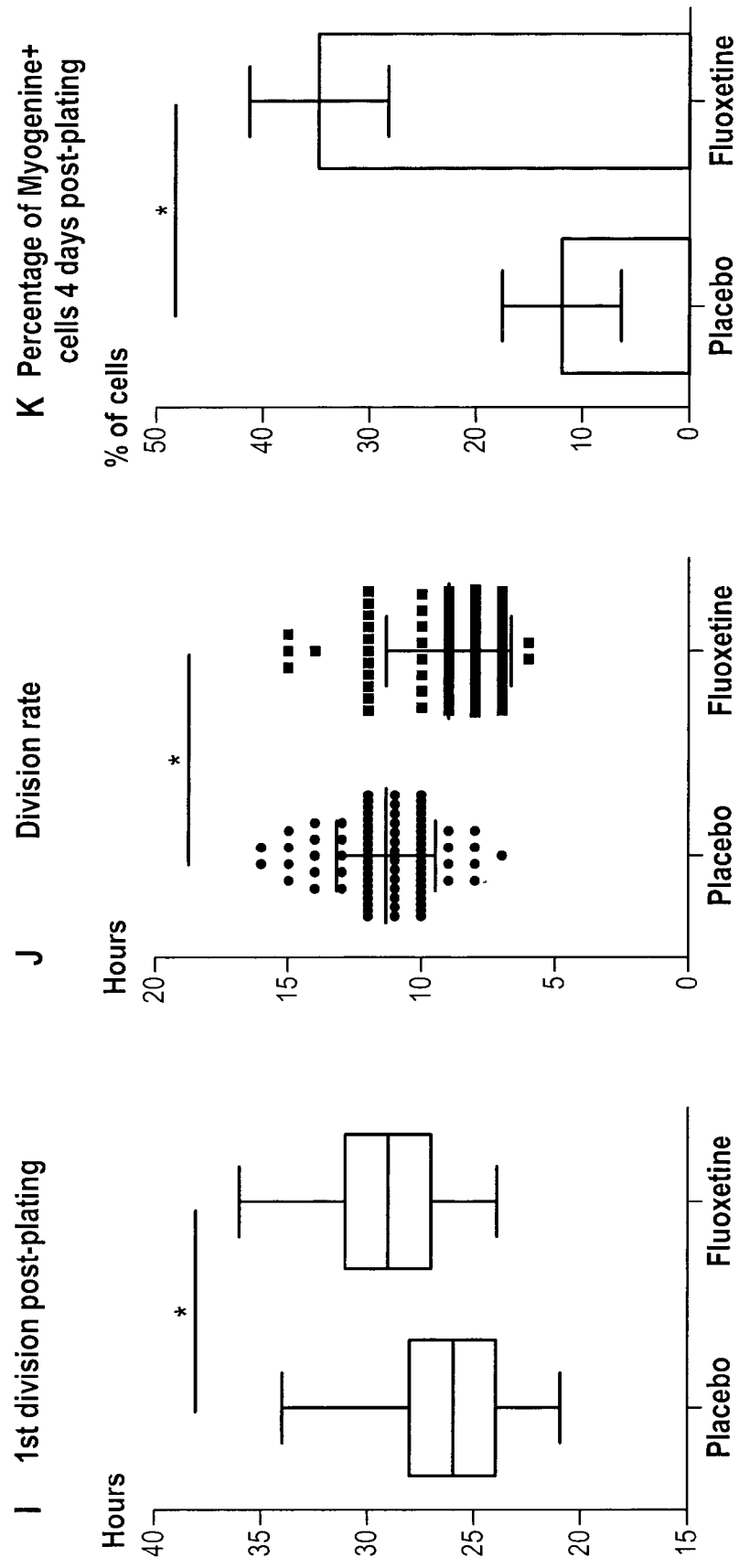

FIG. 4. Muscle regeneration is faster and the number of self-renewing satellite cells is higher after fluoxetine treatment.

(a) Number of immune Gr1 (granulocytes) and F4/80 (macrophages) in the placebo and fluoxetine treated mice, 4 and 14 days post-injury. (b-c) Histological section of staining with sirius red (fibrosis) 14 days post injury in placebo (b) and fluoxetine (c) treated animals. (d) Calcium deposit 14 days post-injury in the placebo vs. fluoxetine treated animals. (e) Number of fibres in the placebo vs. fluoxetine treated animals 14 days post-injury. (f) Number of vessels in a Flk1$^{GFP/+}$ mouse 28 days post-injury in the placebo vs. fluoxetine treated animals. (g) Number of SC in a TgPax7nGFP mouse 28 days post-injury in the placebo vs. fluoxetine treated animals. (h) Number of SC after several rounds of injury in the placebo vs. fluoxetine treated animals. (i) First division assessed by live videomicroscopy in vitro. Cells were plated either with plasma coming from placebo treated C57Bl/6 or fluoxetine treated C57Bl/6 animals. (j) Division rate assessed by live videomicroscopy in vitro. Cells were plated either with plasma coming from placebo treated C57Bl/6 or fluoxetine treated C57Bl/6 animals. (k) Percentage of differentiating (myogenin+) cells 4 days post-plating. Cells were plated either with plasma coming from placebo treated C57Bl/6 or fluoxetine treated C57Bl/6 animals.

n=7 mice used per condition. Data are represented as mean±s.d. *P<0.05; P<0.01; *P<0.001. Scale bar represents 100 μm.

Figure 5:
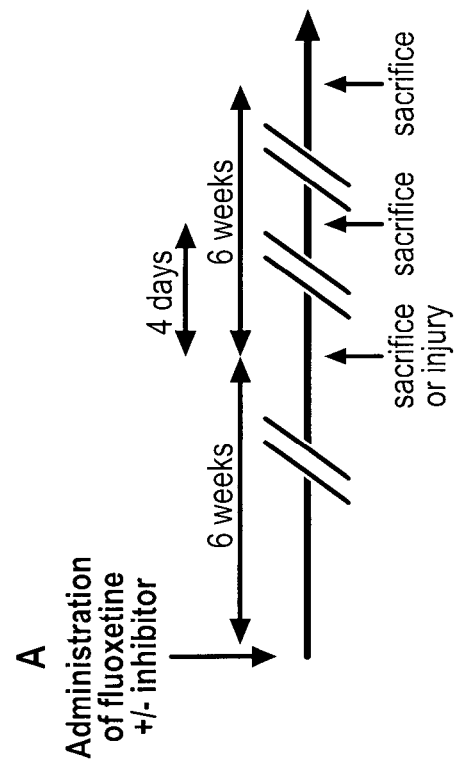
Figure 5:
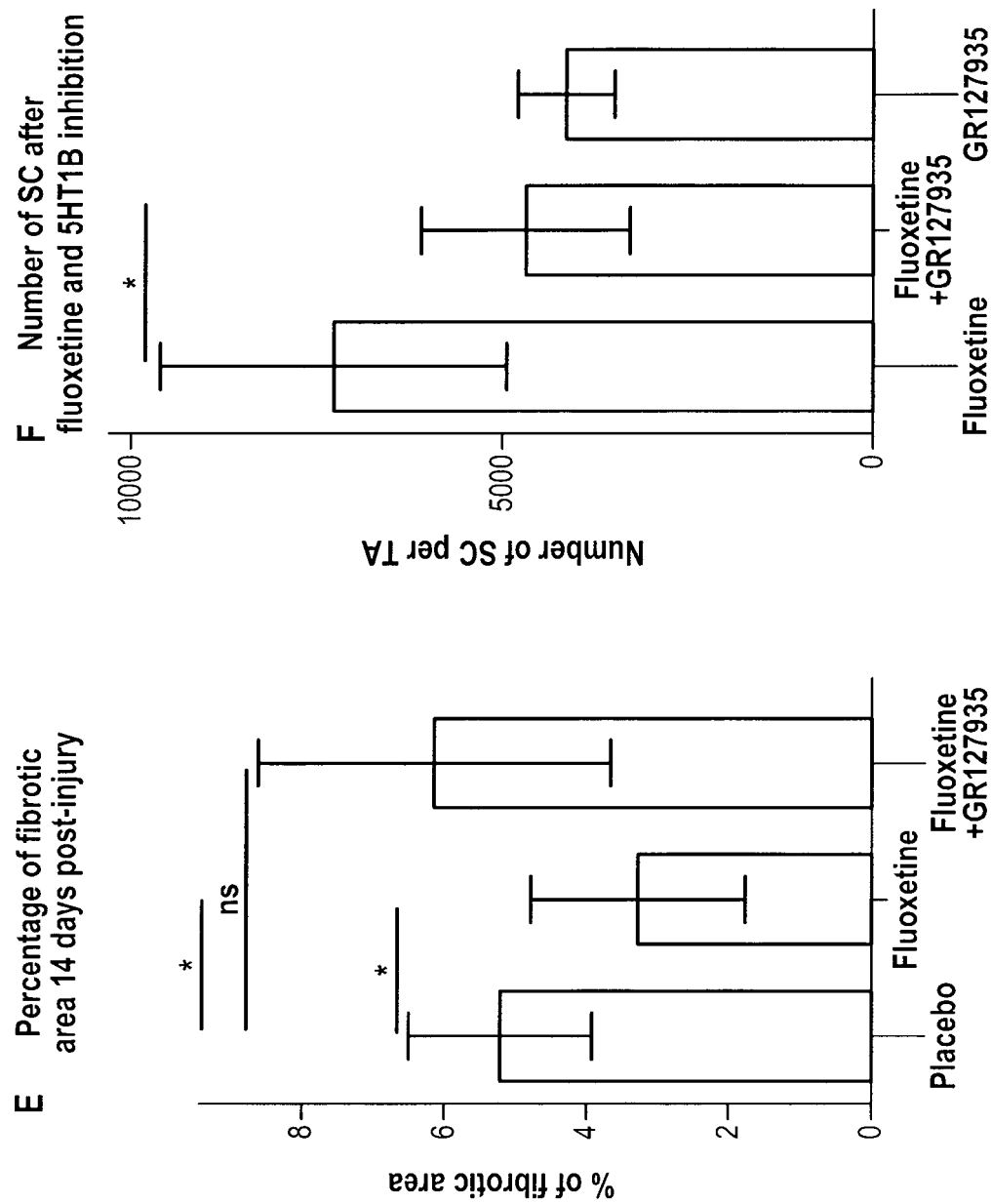
Figure 5:
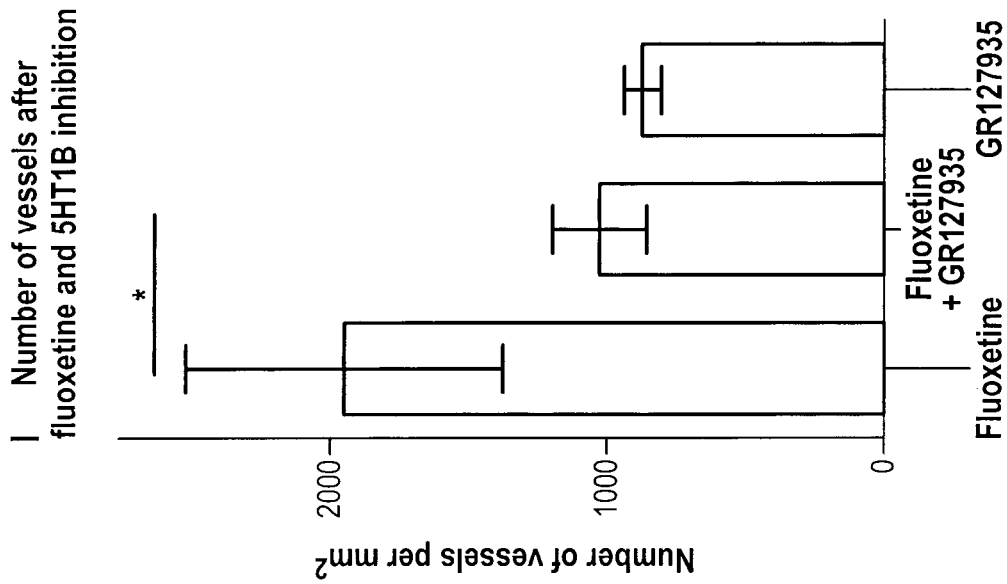
Figure 5:
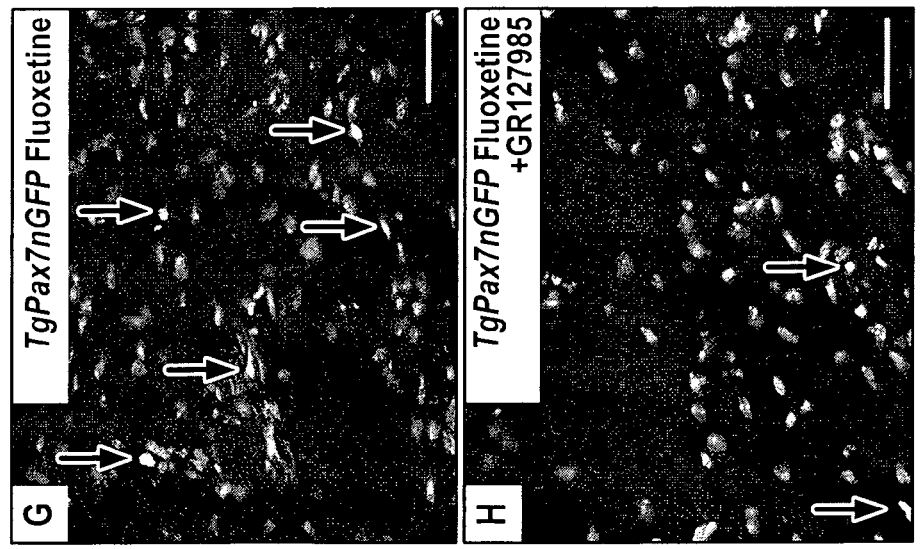

FIG. 5. The effect of fluoxetine on endothelial and satellite cells is achieved via 5-HT1 B receptors (a) Scheme of fluoxetine and inhibitor delivery. (b) Quantification by RT-qPCR of the different serotoninergic receptors displayed as a fold increased/placebo in endothelial and satellite cells. (c) Number of differentiating cells per $mm^2$ (myogenin+) in the placebo, fluoxetine and fluoxetine plus GR127935 5-HT1 B antagonist 4 days post injury. (d) Fibre size 14 days post-injury in $μm^2$ in the placebo, fluoxetine and fluoxetine plus GR127935 5-HT1 B antagonist. (e) Percentage of fibrotic area 14 days post injury. (f) Number of SC per TA of a Tg:Pax7nGFP mouse in fluoxetine, fluoxetine and inhibitor GR127935, inhibitor GR127935 alone. (g-h) representative pictures of the number of GFP+ cells on section in the fluoxetine (g) and fluoxetine with GR127935 5-HT1 B inhibitor (h). The picture displays endogenous GFP. (i) Number of vessels in Flk1$^{GFP/+}$ mice after fluoxetine treatment and GR127935 5-HT1 B antagonist. (j-k) Representative histological section of the number of vessels (counted with endogenous GFP from Flk1$^{GFP/+}$ mouse) in fluoxetine (j), fluoxetine and inhibitor (k) per mm$^2$. n=7 mice used per condition (n=5 for the controls). Data are represented as mean±s.d. *P<0.05; P<0.01; *P<0.001. Scale bar represents 100 μm.

Figure 6:
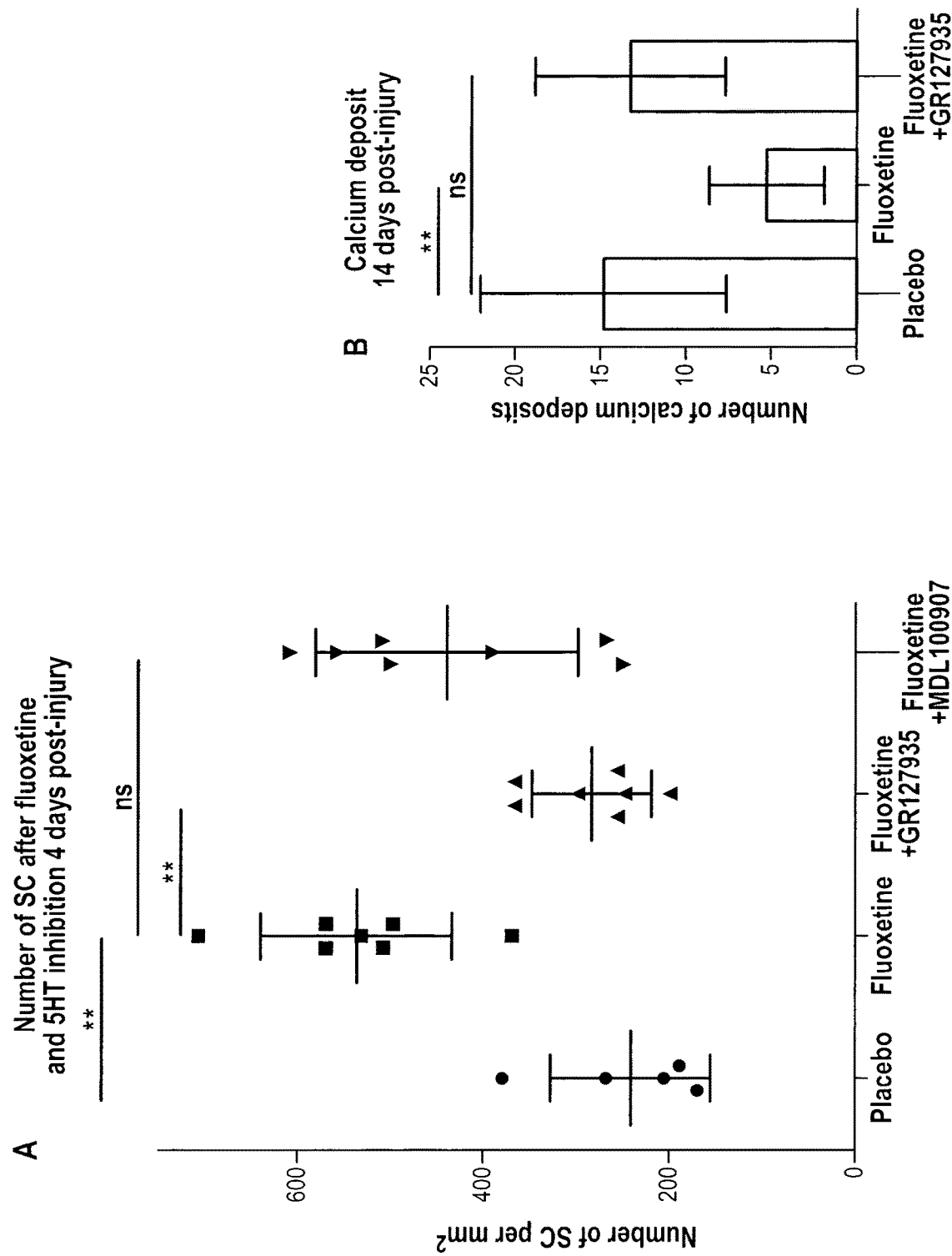
Figure 6:
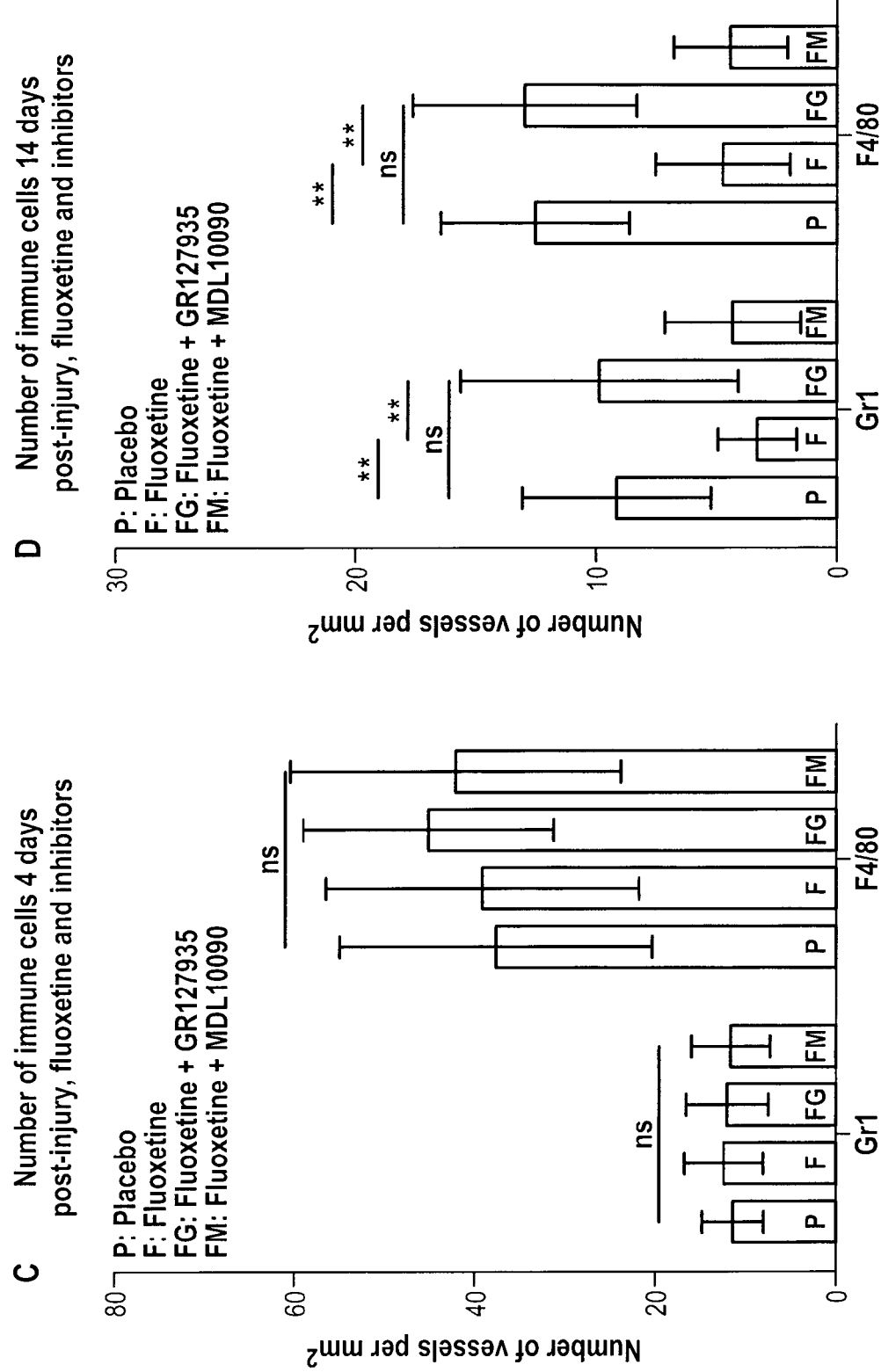
Figure 6:
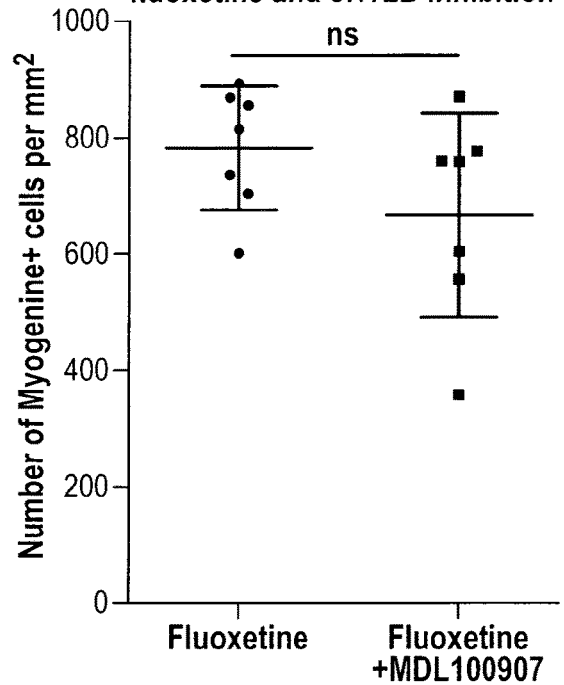
Figure 6:
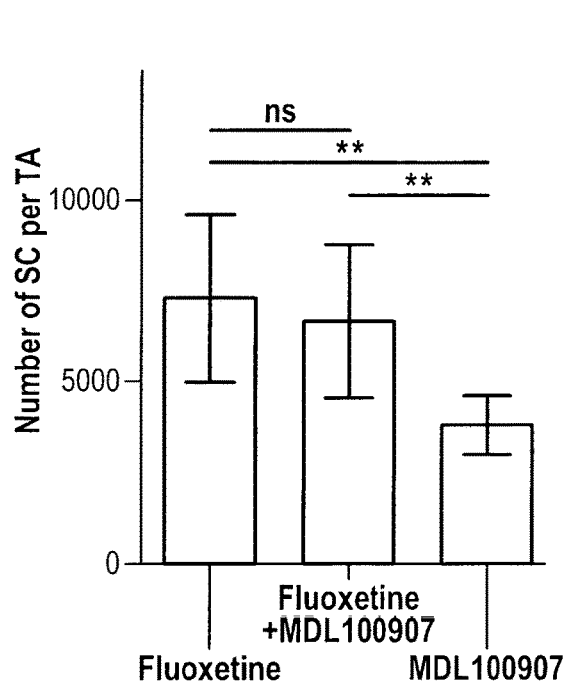
Figure 6:
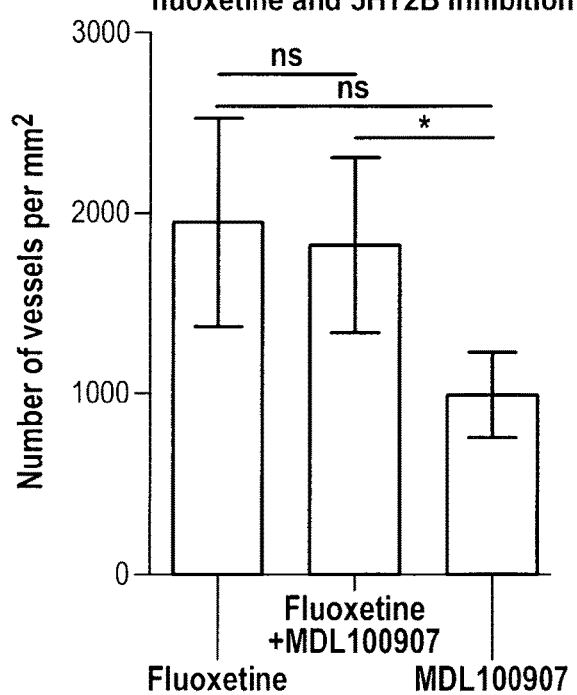

FIG. 6. 5-HT1 BR, and not 5-HT2 BR, is involved in fluoxetine effect.

(a) Number of SC 4 days post-injury in the placebo, fluoxetine, fluoxetine and GR127935 5-HT1 BR antagonist and MDL100907 5-HT2 BR antagonist. (b) Calcium deposit 14 days post-injury in the placebo, fluoxetine, fluoxetine and GR127935 5-HT1 BR antagonist. (c) Number of immune Gr1 (granulocytes) and F4/80 (macrophages) 4 days post-injury in the placebo, fluoxetine, fluoxetine and GR127935 5-HT1 B antagonist and MDL100907 5-HT2 BR antagonist. (d) Number of immune Gr1 (granulocytes) and F4/80 (macrophages) 14 days post-injury in the placebo, fluoxetine, fluoxetine and GR127935 5-HT1 BR antagonist and MDL100907 5-HT2 BR antagonist. (e) Number of differentiating cells (myogenin+) 4 days post-injury with fluoxetine and fluoxetine and 5-HT2 BR antagonist. (f) Number of SC from TgPax7nGFP after 5-HT2 BR inhibition by MDL100907 antagonist. (g) Number of vessels from Flk1$^{GFP/+}$ after 5-HT2 BR inhibition by MDL100907 antagonist.

n=6 mice used per condition (n=5 for the controls). Data are represented as mean±s.d. *P<0.05; P<0.01; *P<0.001. Scale bar represents 100 μm.

Figure 7:
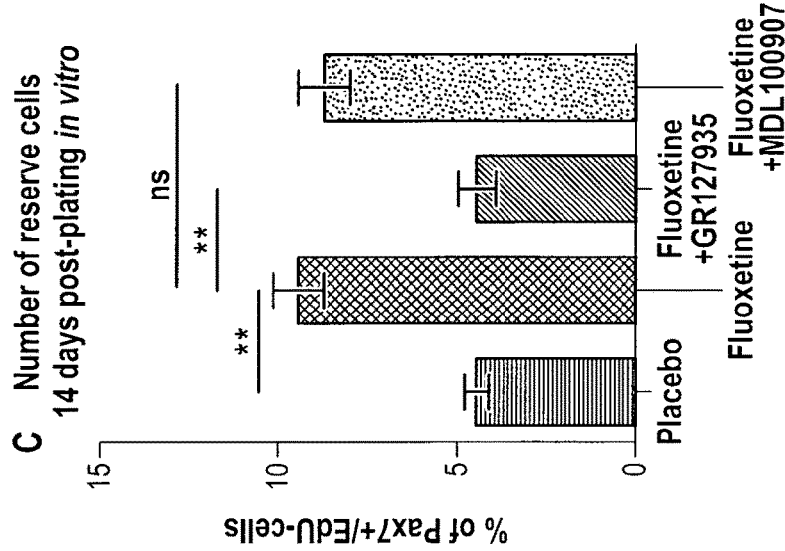
Figure 7:
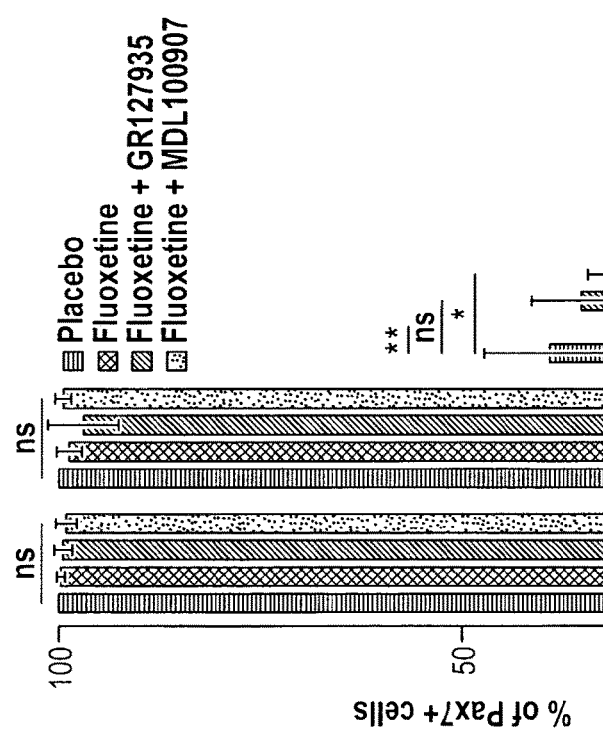
Figure 7:
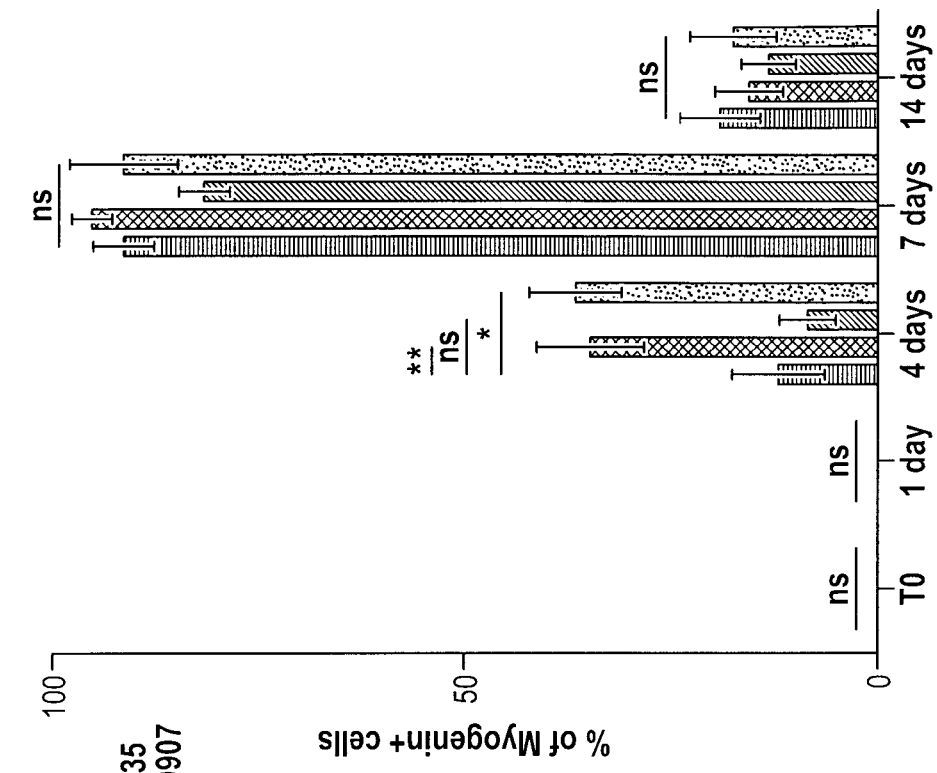
Figure 7:
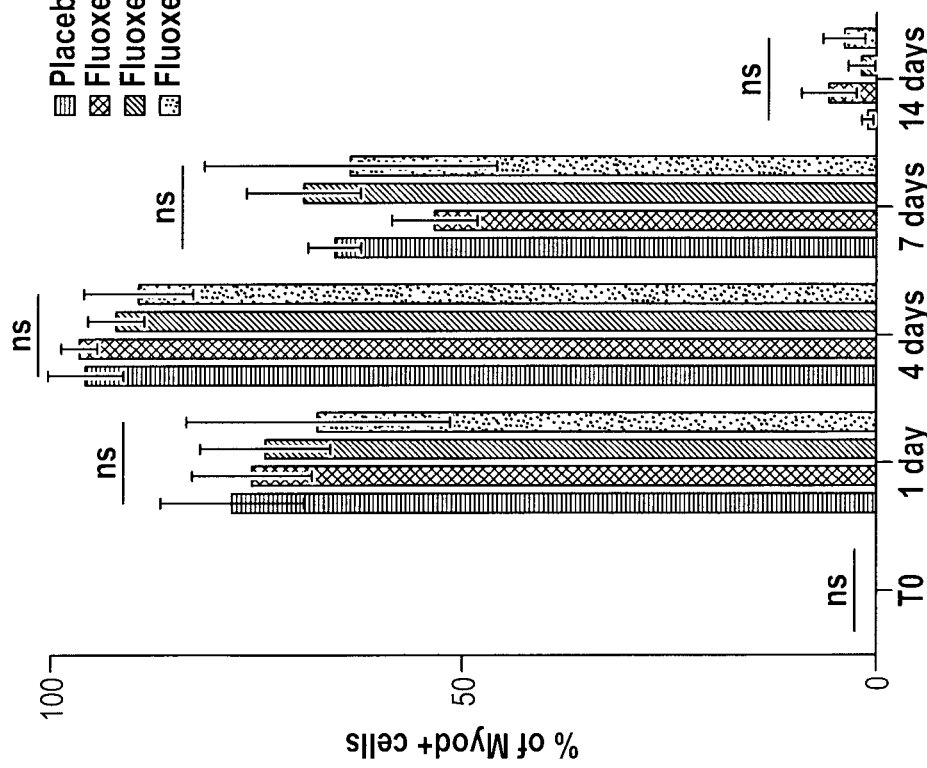
Figure 7:
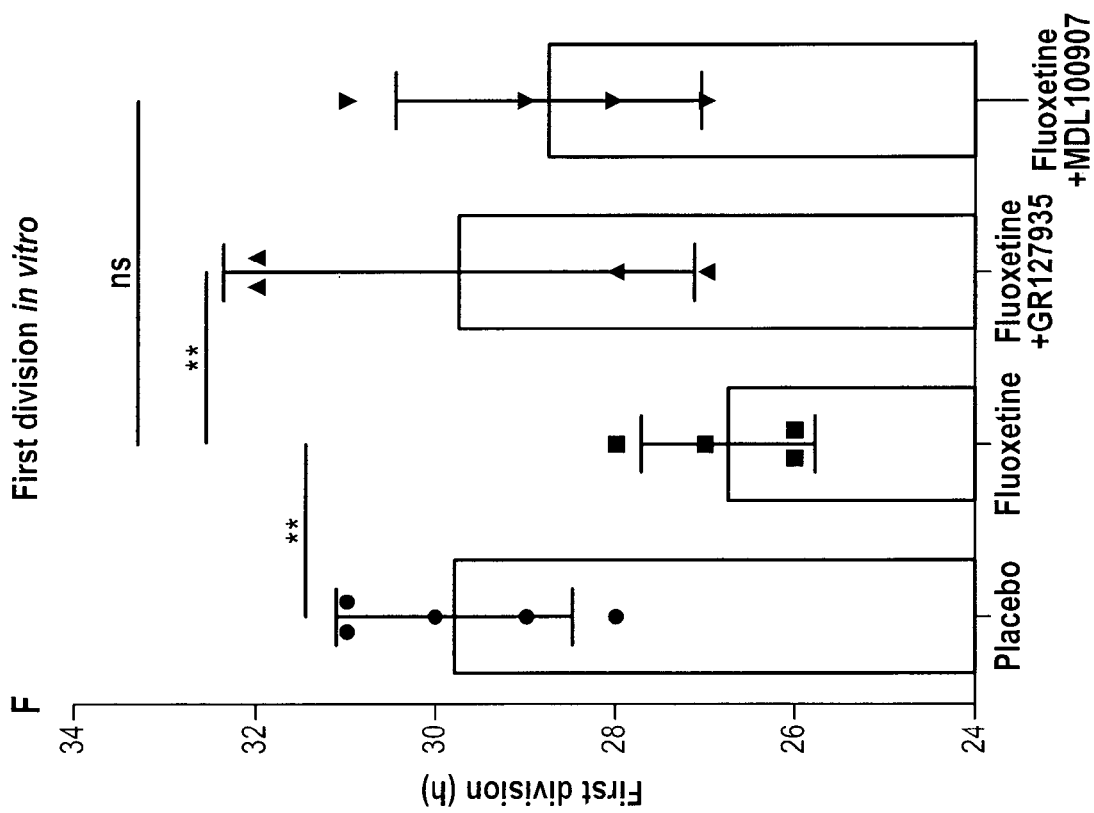
Figure 7:
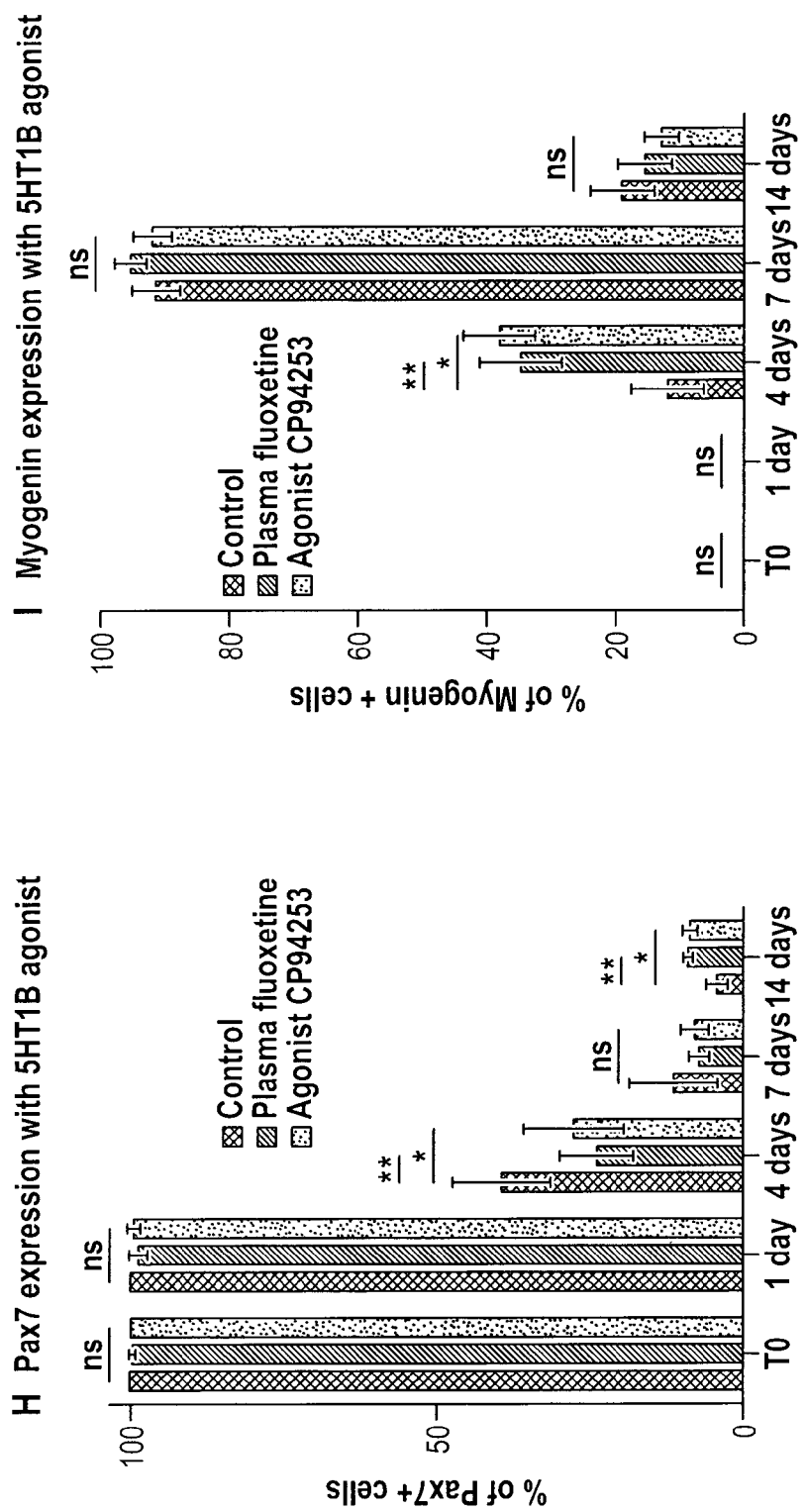
Figure 7:
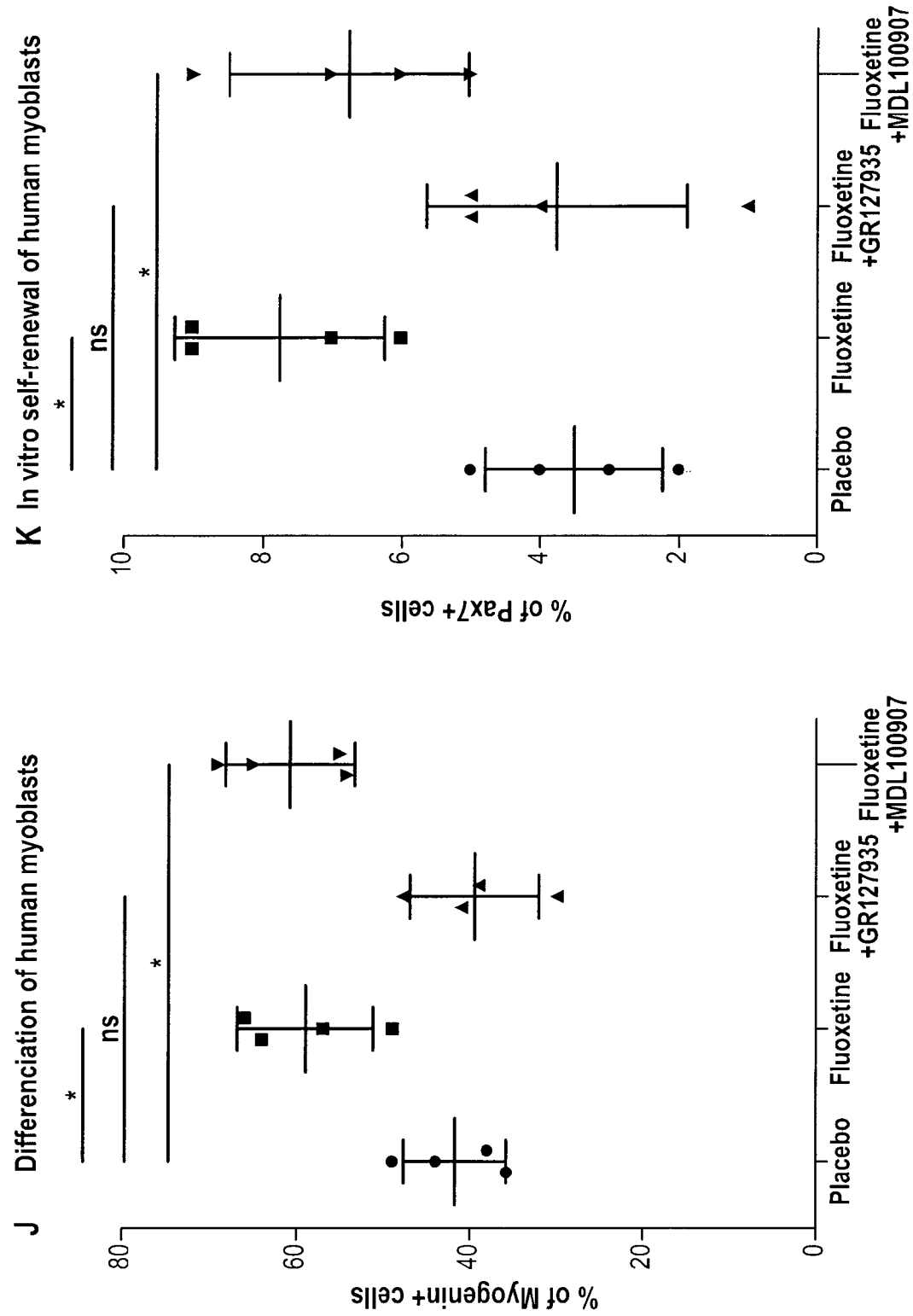

FIG. 7. In vitro plasma from fluoxetine treated mice accelerates differentiation at early stages and increases self-renewal at later stages of both murine and human satellite cells.

(a) Scheme of fluoxetine and inhibitor delivery in vitro. (b) Percentage of Pax7+ cells among the total number of FACS sorted SC through time in placebo plasma, fluoxetine plasma, fluoxetine plasma with GR127935 inhibitor in vitro, fluoxetine plasma with MDL100907 inhibitor. (c) Number of self-renewed (also called reserve cells)SC (Pax7+/EdU−) 14 days post plating of FACS sorted SC in placebo plasma, fluoxetine plasma, fluoxetine plasma with GR127935 inhibitor in vitro, fluoxetine plasma with MDL100907 inhibitor. (d) Percentage of MyoD+ cells among the total number of FACS sorted SC through time in placebo plasma, fluoxetine plasma, fluoxetine plasma with GR127935 inhibitor in vitro, fluoxetine plasma with MDL100907 inhibitor. (e) Percentage of Myogenin+ cells among the total number of FACS sorted SC through time in placebo plasma, fluoxetine plasma, fluoxetine plasma with GR127935 inhibitor in vitro, fluoxetine plasma with MDL100907 inhibitor. (f) First cell division assessed by live videomicroscopy in placebo plasma, fluoxetine plasma, fluoxetine plasma with GR127935 inhibitor in vitro, fluoxetine plasma with MDL100907 inhibitor. (g) Division rate assessed by live videomicroscopy in placebo plasma, fluoxetine plasma, fluoxetine plasma with GR127935 inhibitor in vitro, fluoxetine plasma with MDL100907 inhibitor. (h) Percentage of Pax7+ cells investigated by immunofluorescence in vitro co-cultured with CP94253 5HT1B specific agonist. (i) Percentage of Myogenin+ cells investigated by immunofluorescence in vitro co cultured with CP94253 5HT1BR specific agonist. (j) Differentiation (Myogenin+) cells coming from primary human SC obtained through pre-plating technique 4 days post-plating in placebo plasma, fluoxetine plasma, fluoxetine plasma with GR127935 inhibitor in vitro, fluoxetine plasma with MDL100907 inhibitor. (k) Self-renewal (Pax7+/EdU−) cells coming from primary human SC obtained through pre-plating technique 14 days post-plating in placebo plasma, fluoxetine plasma, fluoxetine plasma with GR127935 inhibitor in vitro, fluoxetine plasma with MDL100907 inhibitor.

n=6 mice used per condition, except for human myoblasts where n=4 per condition. Data are represented as mean±s.d. *P<0.05; P<0.01; *P<0.001. Scale bar represents 100 μm.

Figure 8:
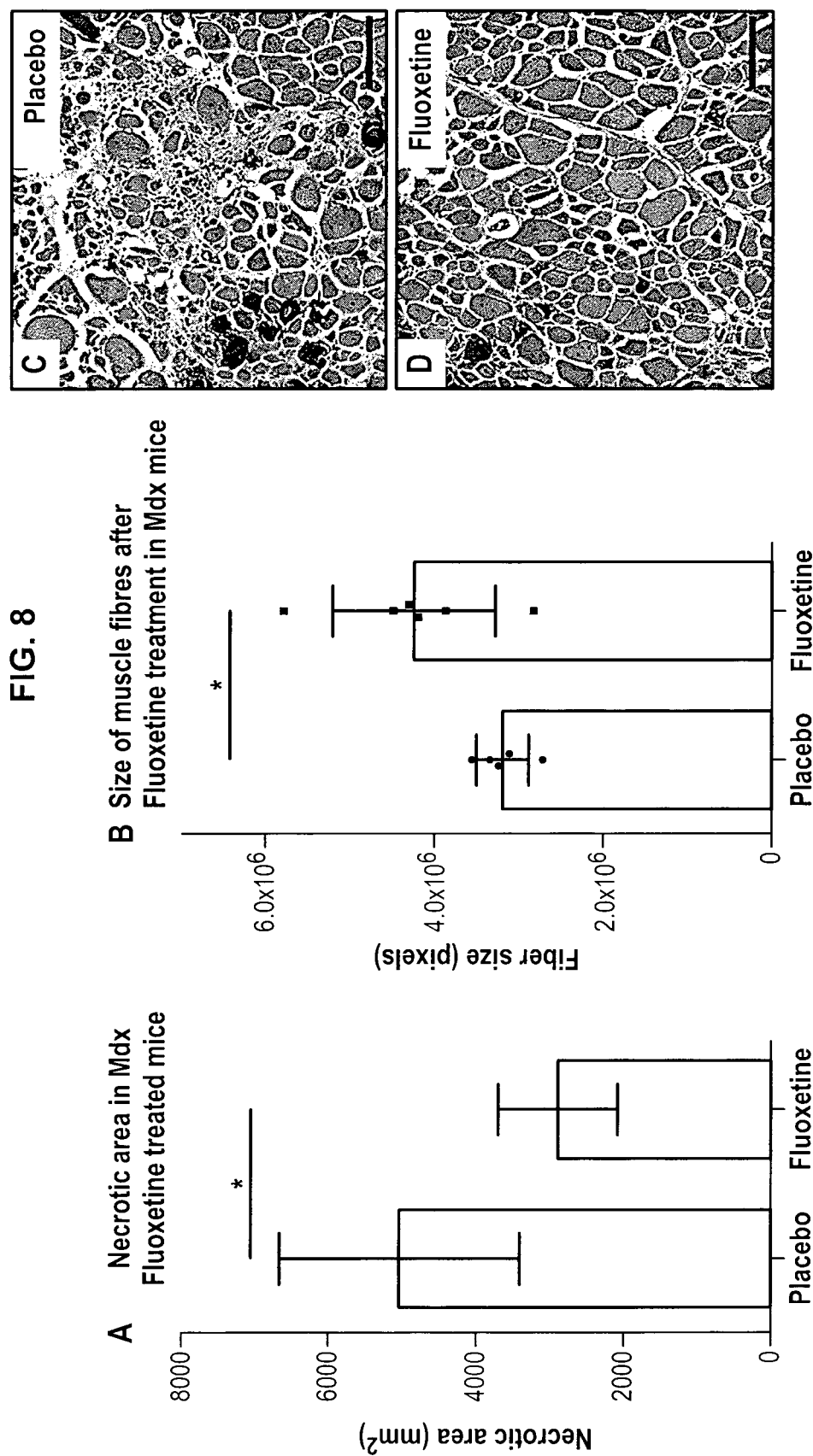
Figure 8:
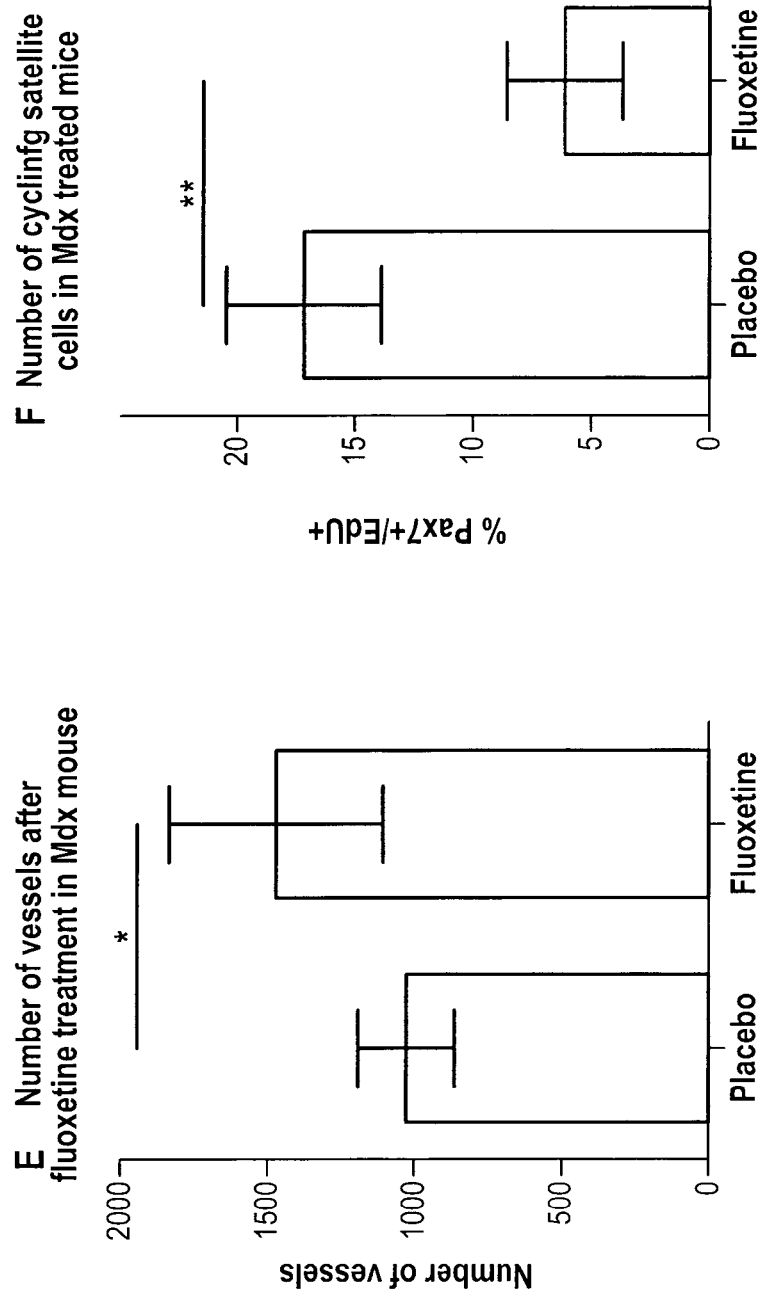
Figure 8:
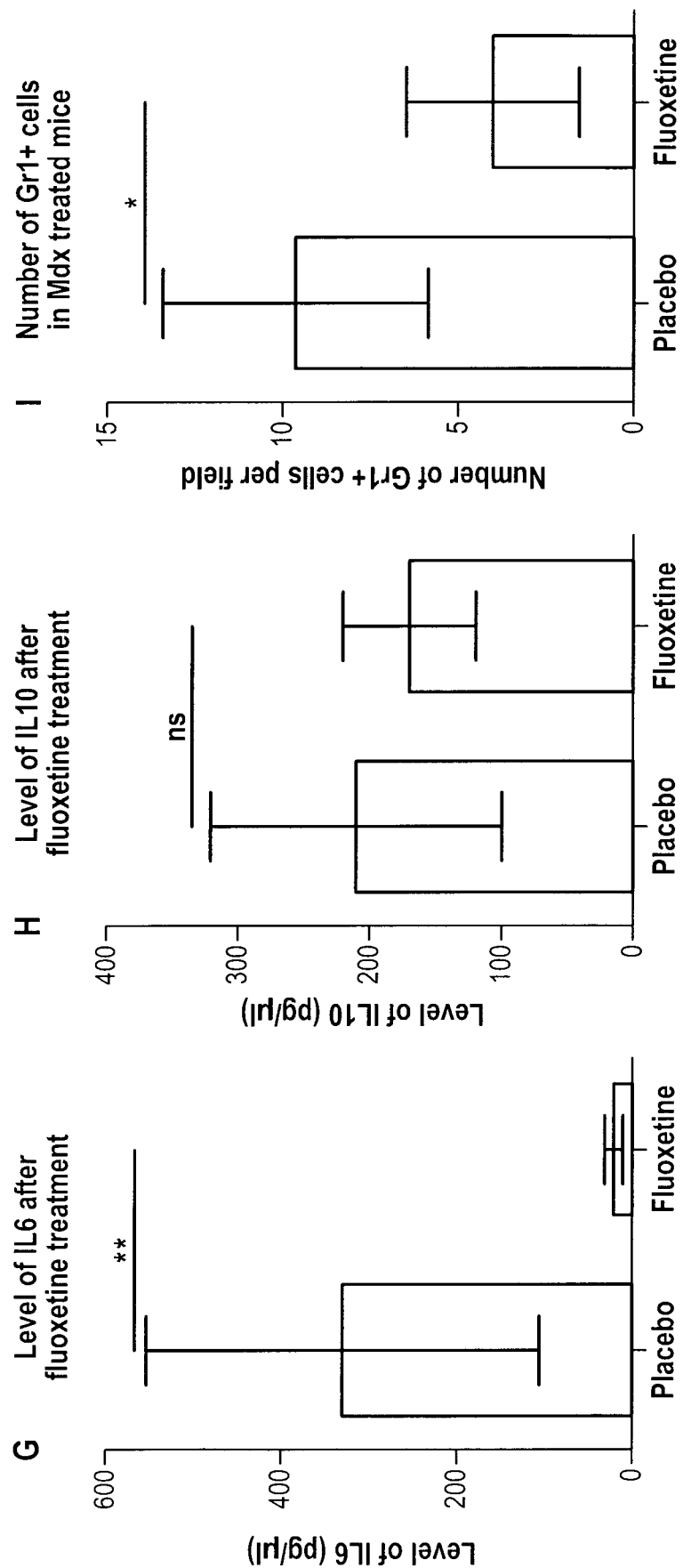

FIG. 8. Fluoxetine improves the phenotype of dystrophic mice (a) Quantification of the necrotic area (in mm$^2$) in placebo and fluoxetine treated animals. (b) Fibre size (area) of placebo and fluoxetine-treated Mdx mice. (c-d) Haematoxylin and eosin staining of cryo-sectioned TA of Mdx mice treated with either placebo (c) or fluoxetine (d). (e) Number of vessels in Mdx mouse either treated with placebo or with fluoxetine counted by immunostaining with CD31 and expressed in number of cells per mm$^2$. (f) Number of cycling cells (Pax7+ and BrdU+ cells) in Mdx mouse either treated with placebo or with fluoxetine. (g) Example of Luminex® on Interleukin 6 (IL6) representing the level of protein expression in picogram/gram of plasma on both placebo and fluoxetine treated mice. (h) Example of Luminex® on Interleukin 10 (IL10) representing the level of protein expression in picogram/gram of plasma on both placebo and fluoxetine treated mice. (i) Number of Gr1+ cells in cryo-sectioned TA of placebo treated and fluoxetine treated Mdx mice. Numbers are displayed in absolute number per cross sections.

Figure 9:
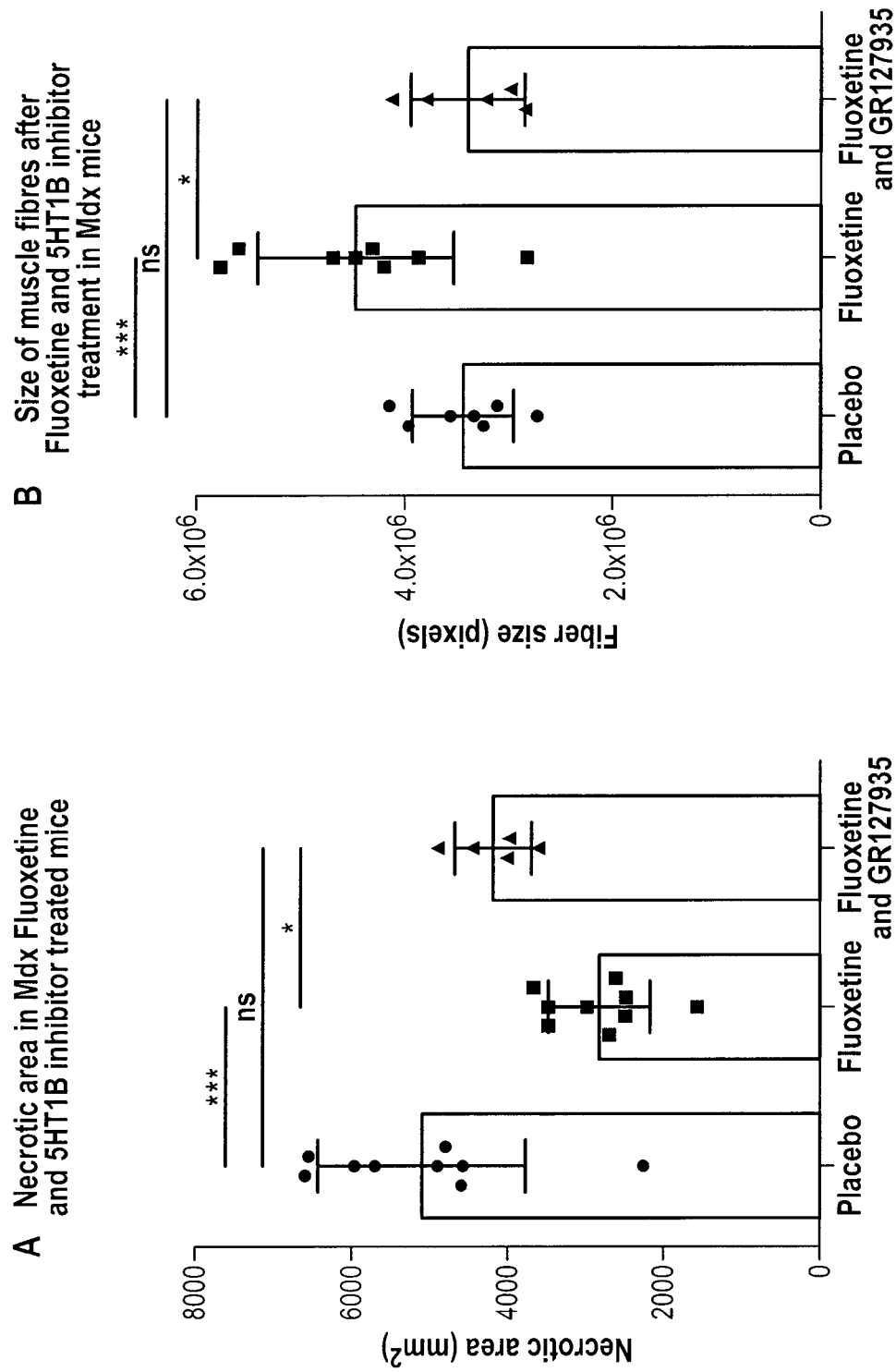
Figure 9:
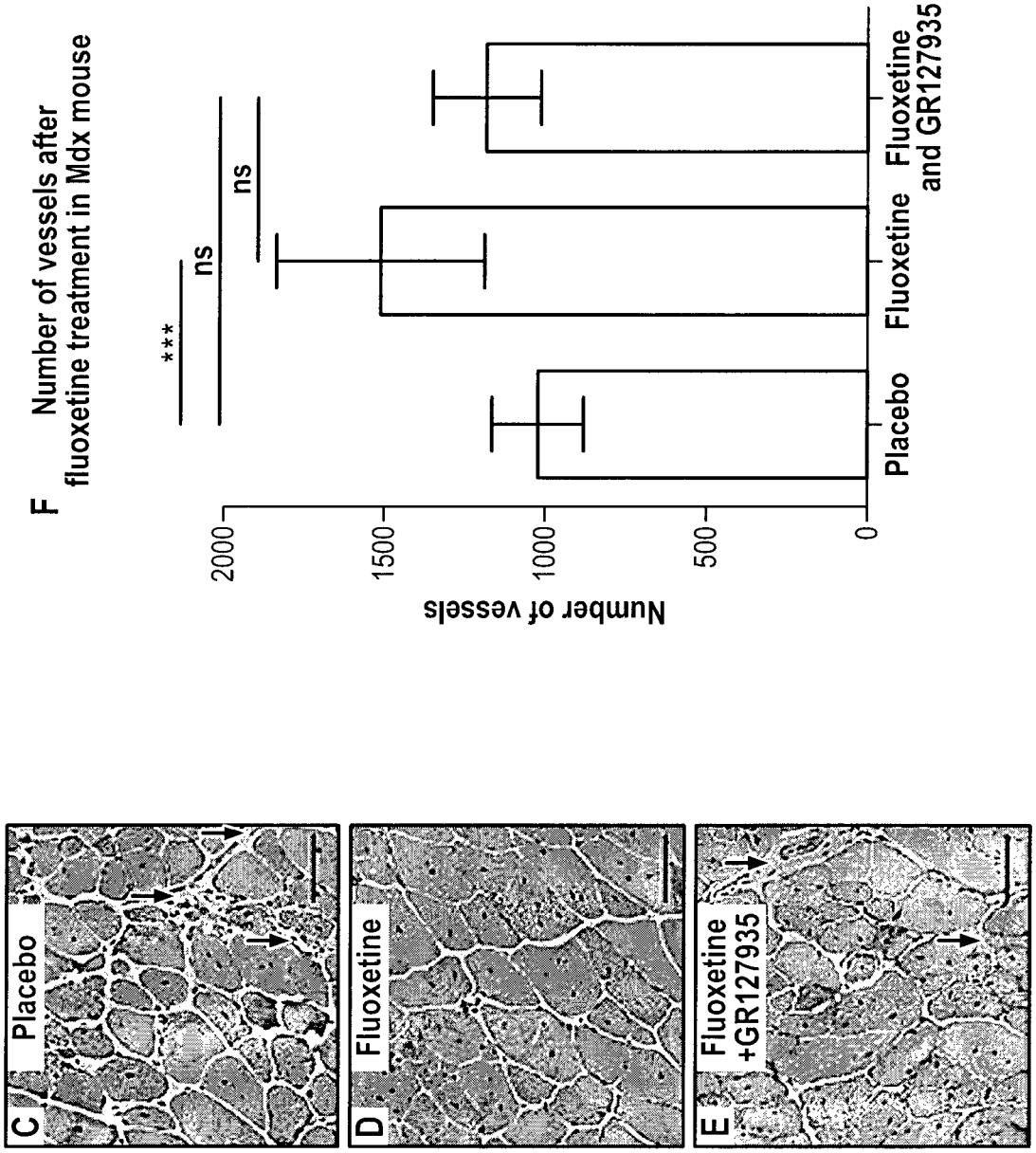
Figure 9:
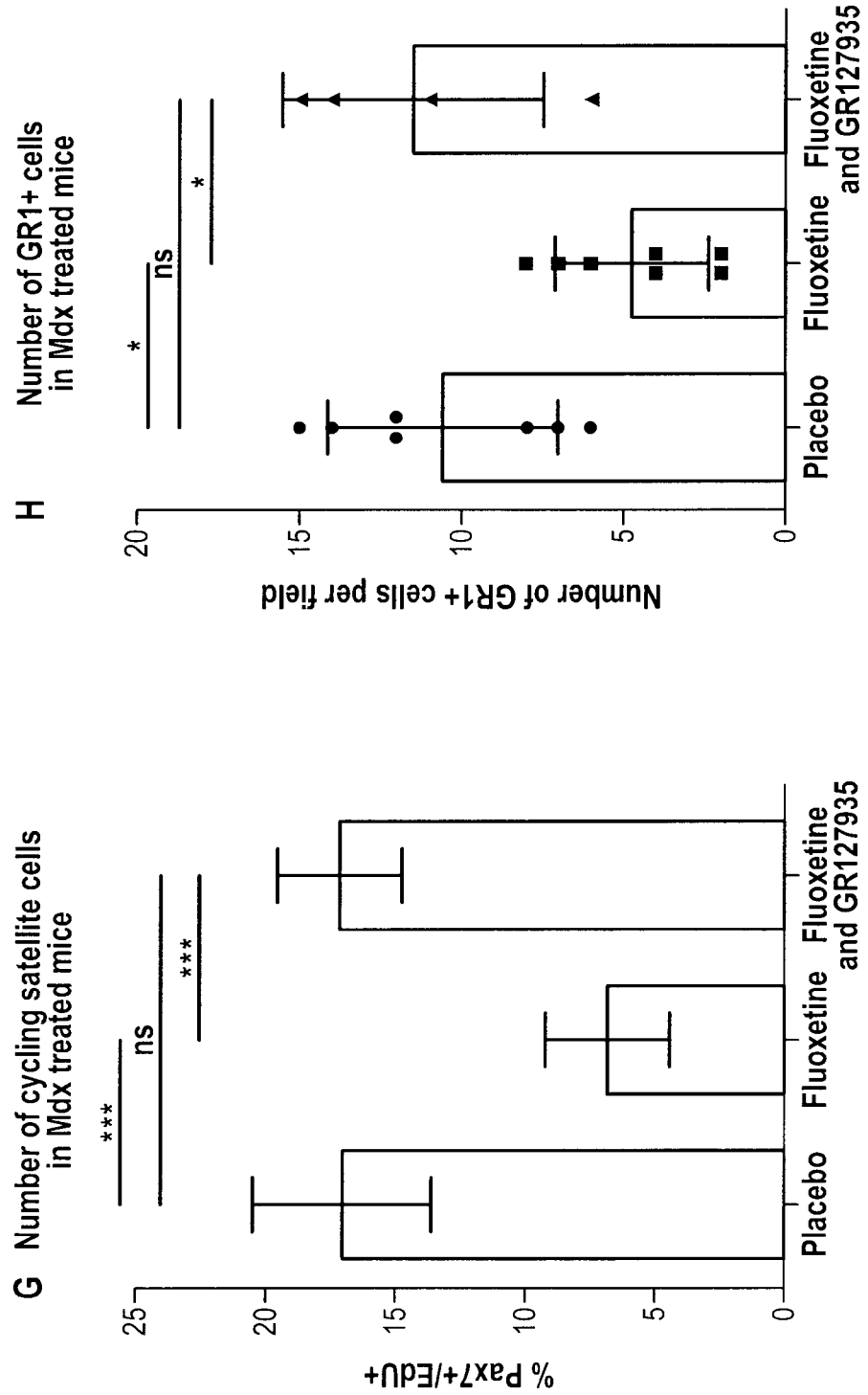
Figure 9:
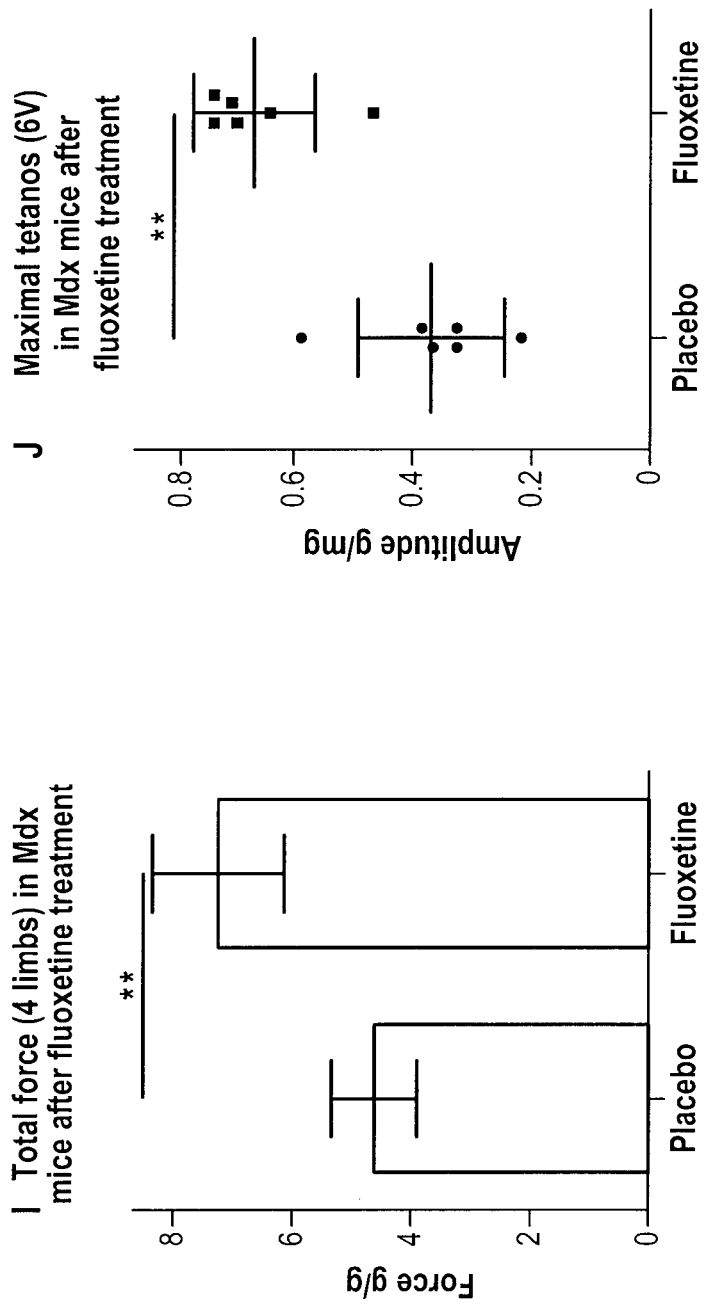
Figure 9:
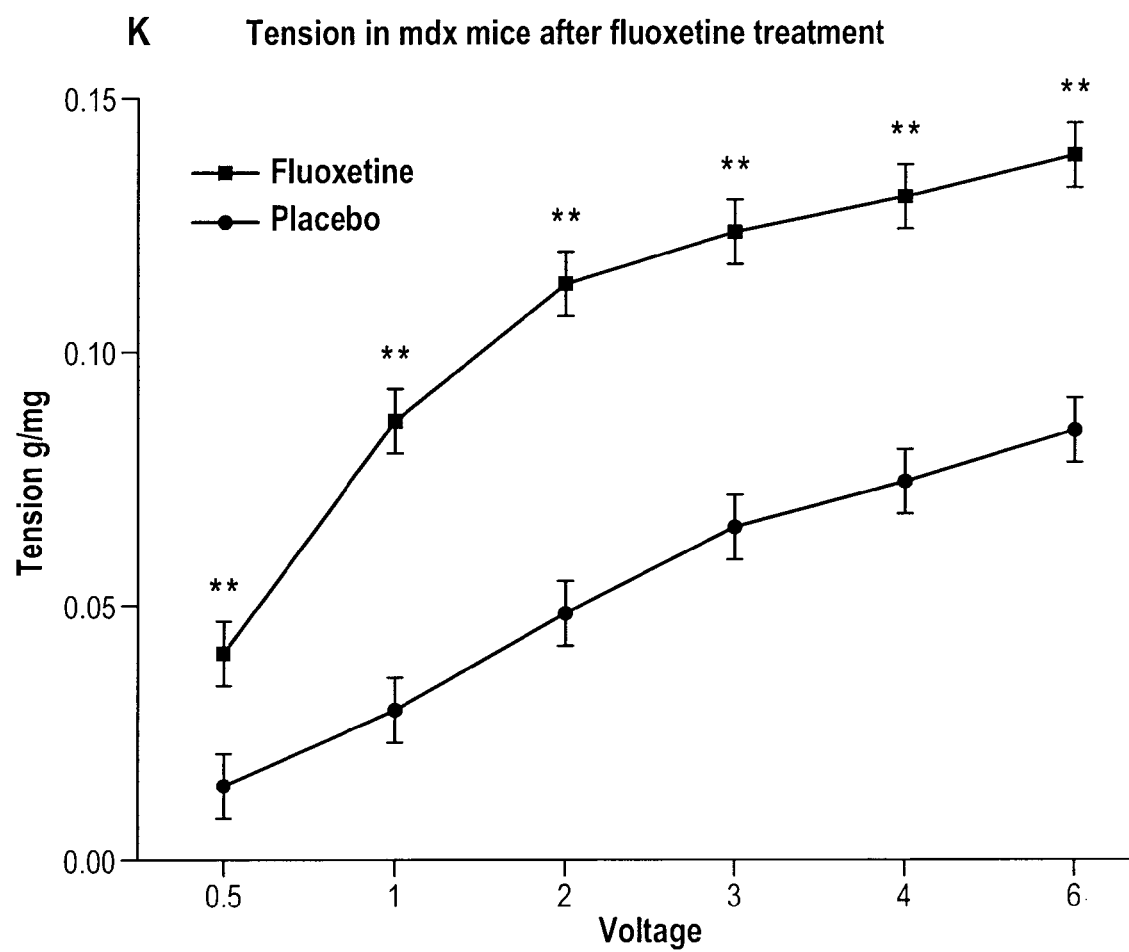

FIG. 9. Antagonising 5HT1B-R eliminates the beneficial effects of fluoxetine on dystrophic phenotype (a) Quantification of the necrotic area (in mm$^2$) in placebo, fluoxetine and fluoxetine with GR127935 5HT1BR inhibitor treated animals. (b) Fibre size (area) of placebo, fluoxetine and fluoxetine with GR127935 5HT1BR inhibitor treated Mdx mice. (c-e) Haematoxylin and eosin staining of cryo-sectioned TA of Mdx mice treated with either placebo (c) or fluoxetine (d) or fluoxetine and GR127935 inhibitor (e). (f) Number of vessels in Mdx mouse either treated with placebo, fluoxetine or fluoxetine and GR127935 5HT1BR inhibitor counted by immunostaining with CD31 and expressed in number of cells per mm$^2$. (g) Number of cycling cells (Pax7+ and EdU+ cells) in Mdx either treated with placebo, with fluoxetine or fluoxetine and GR127935 5HT1BR inhibitor. (h) Number of Gr1+ cells in cryo-sectioned TA of placebo treated and fluoxetine treated Mdx mice. Numbers are displayed in absolute number per cross sections. n=9 mice per condition. Data are represented as mean±s.d. *P<0.05; ***P<0.001; ns: not significant. Scale bar represents 100 μm. (i) Force grip test. The total force of animals was measured (4 limbs) in fluoxetine and placebo treated mice. (j) Maximal tension (6V) of edl muscle fibers of fluoxetine or placebo treated mdx mice. (k) Tension of isolated edl through different voltage in placebo and fluoxetine treated mdx mice.

Figure 10:
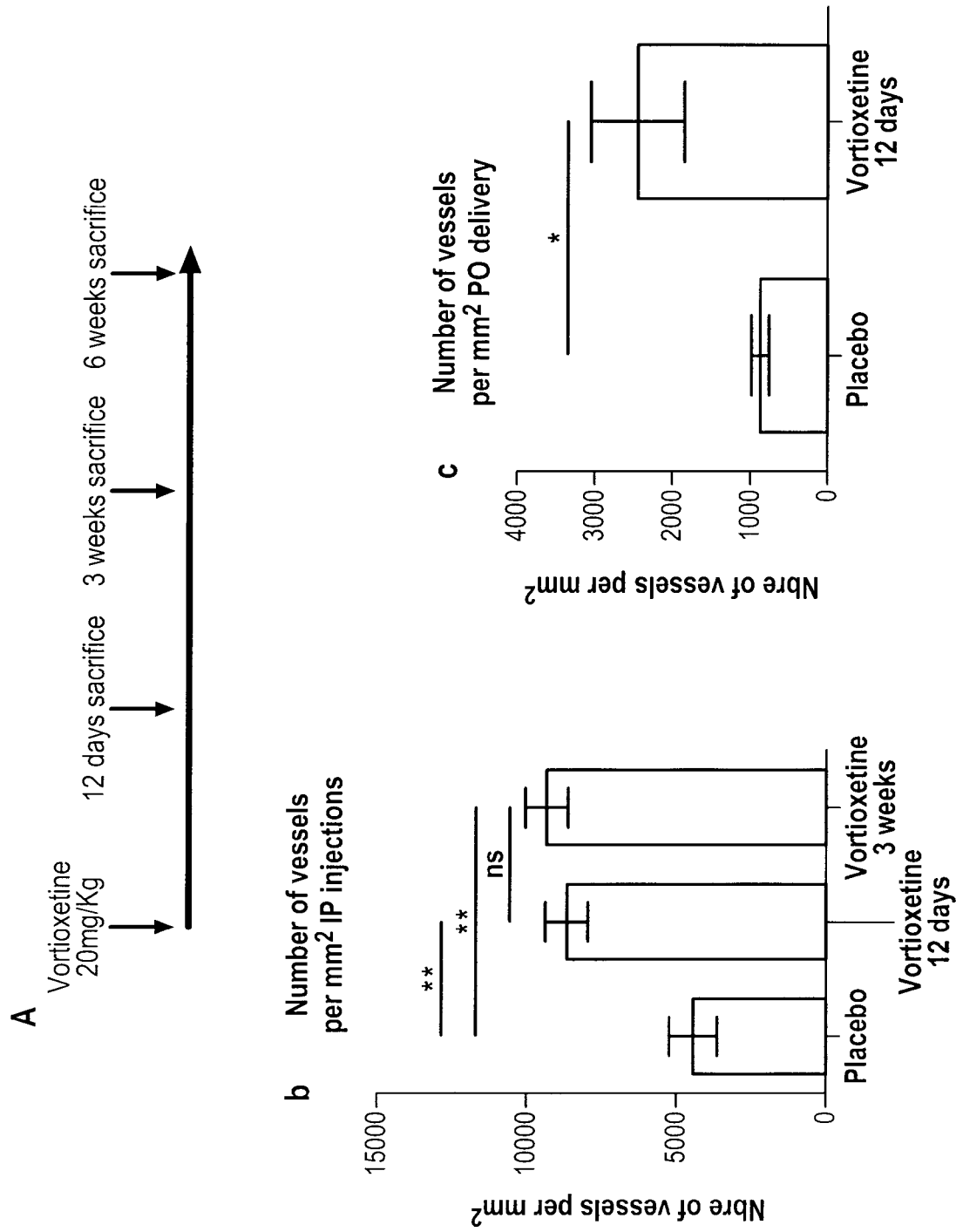
Figure 10:
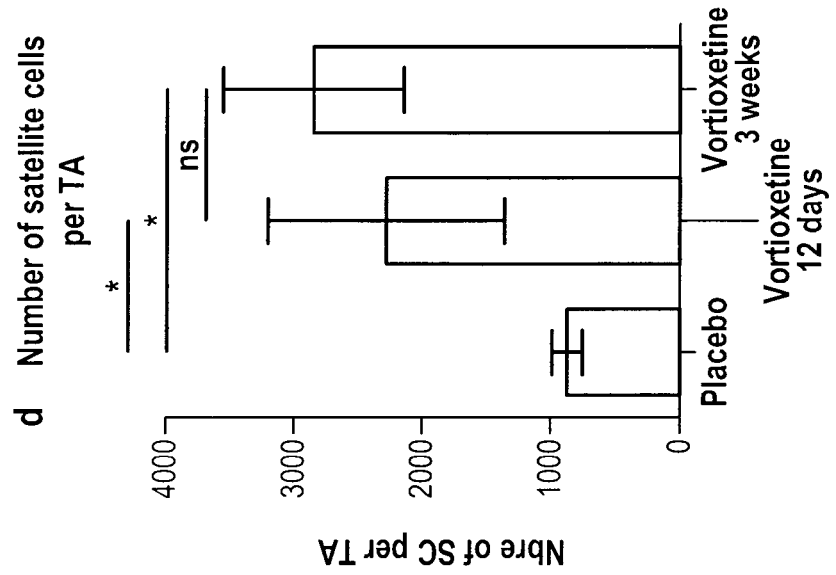

FIG. 10. Vortioxetine increases the number of vessels and the number of satellite cells in vivo. (a) Schematic representation of vortioxetine delivery and timing of sacrifice. (b) Number of vessels counted on section after CD31 immunostaining per mm² after I.P treatment. (c) Number of vessels counted on section after CD31 immunostaining per mm² after P.O treatment. (d) Number of satellite cells counted by FACS in placebo, 12 days and 3 weeks vortioxetine I.P treated Tg:Pax7nGFP mice. (e) Number of satellite cells counted by FACS in placebo, 12 days and 3 weeks vortioxetine P.O treated Tg:Pax7nGFP mice.

Figure 11:
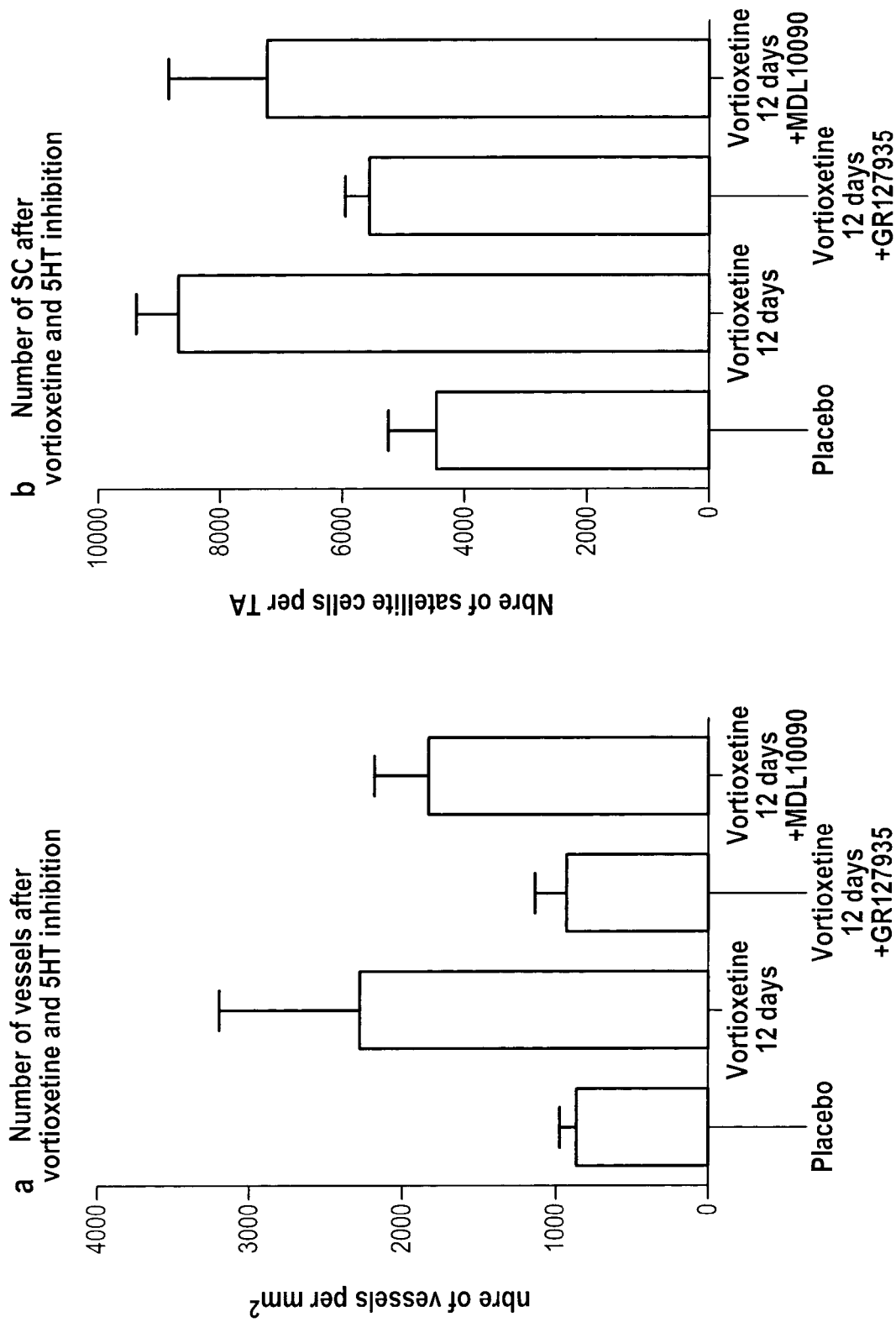
Figure 11:
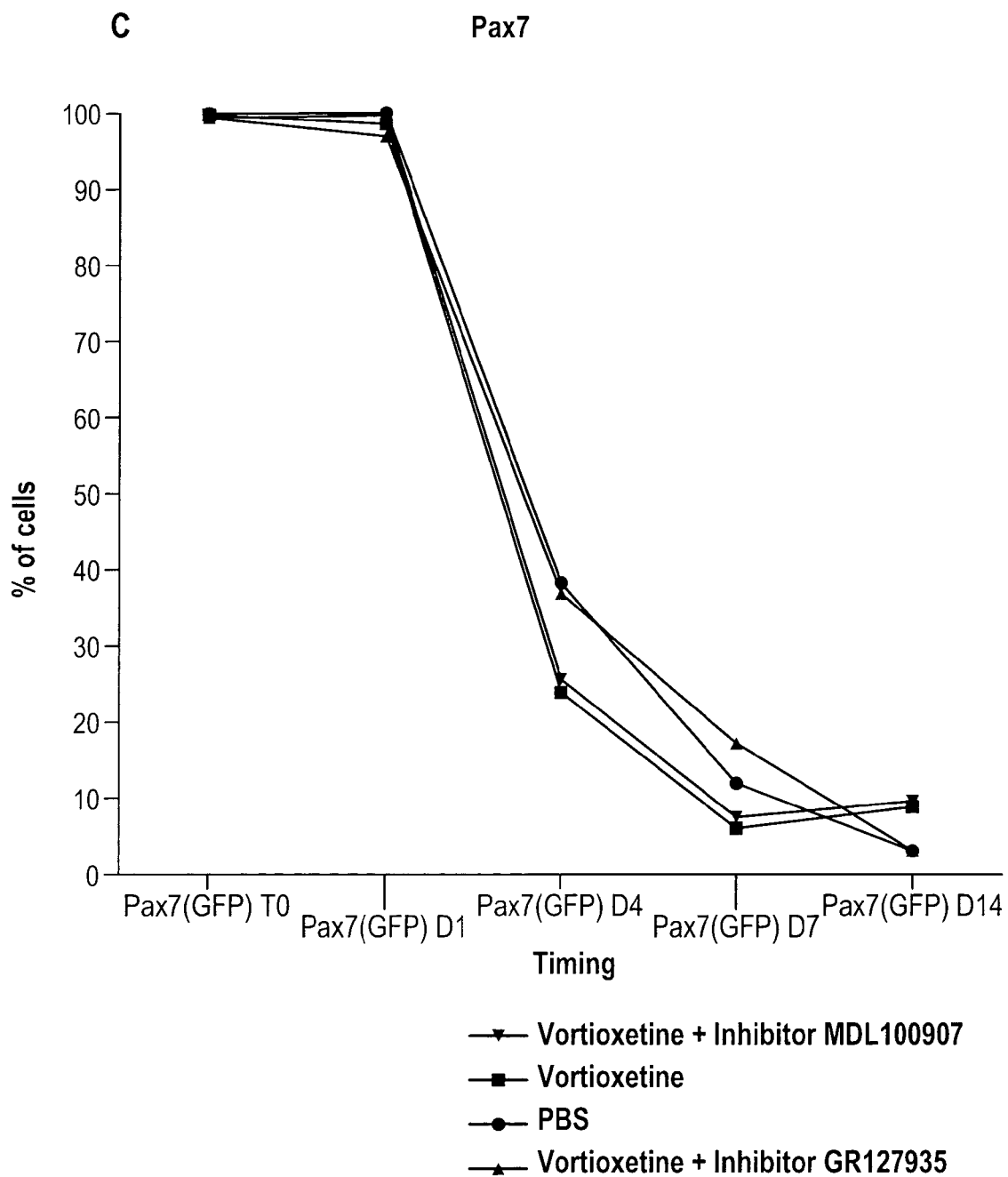
Figure 11:
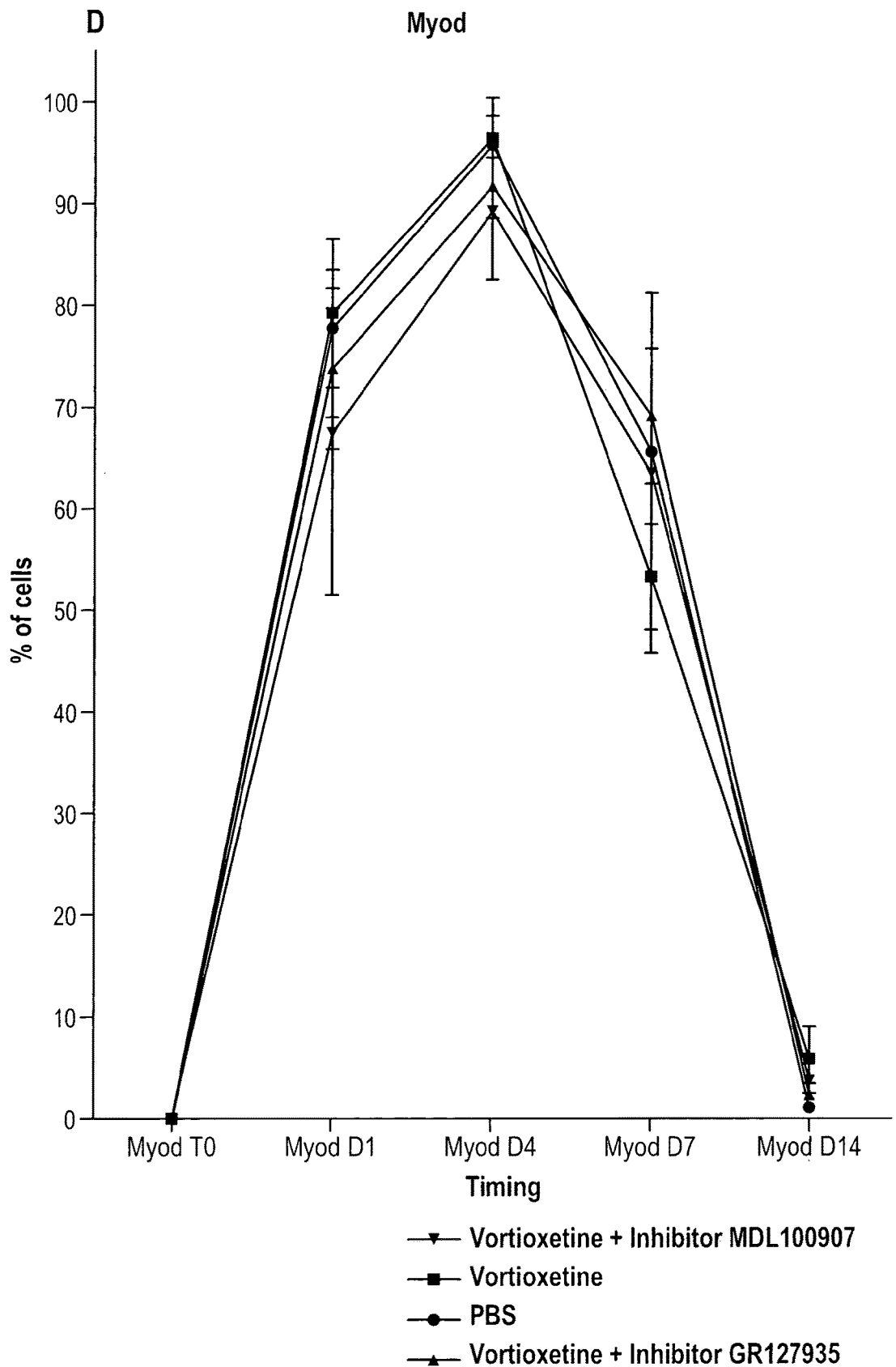
Figure 11:
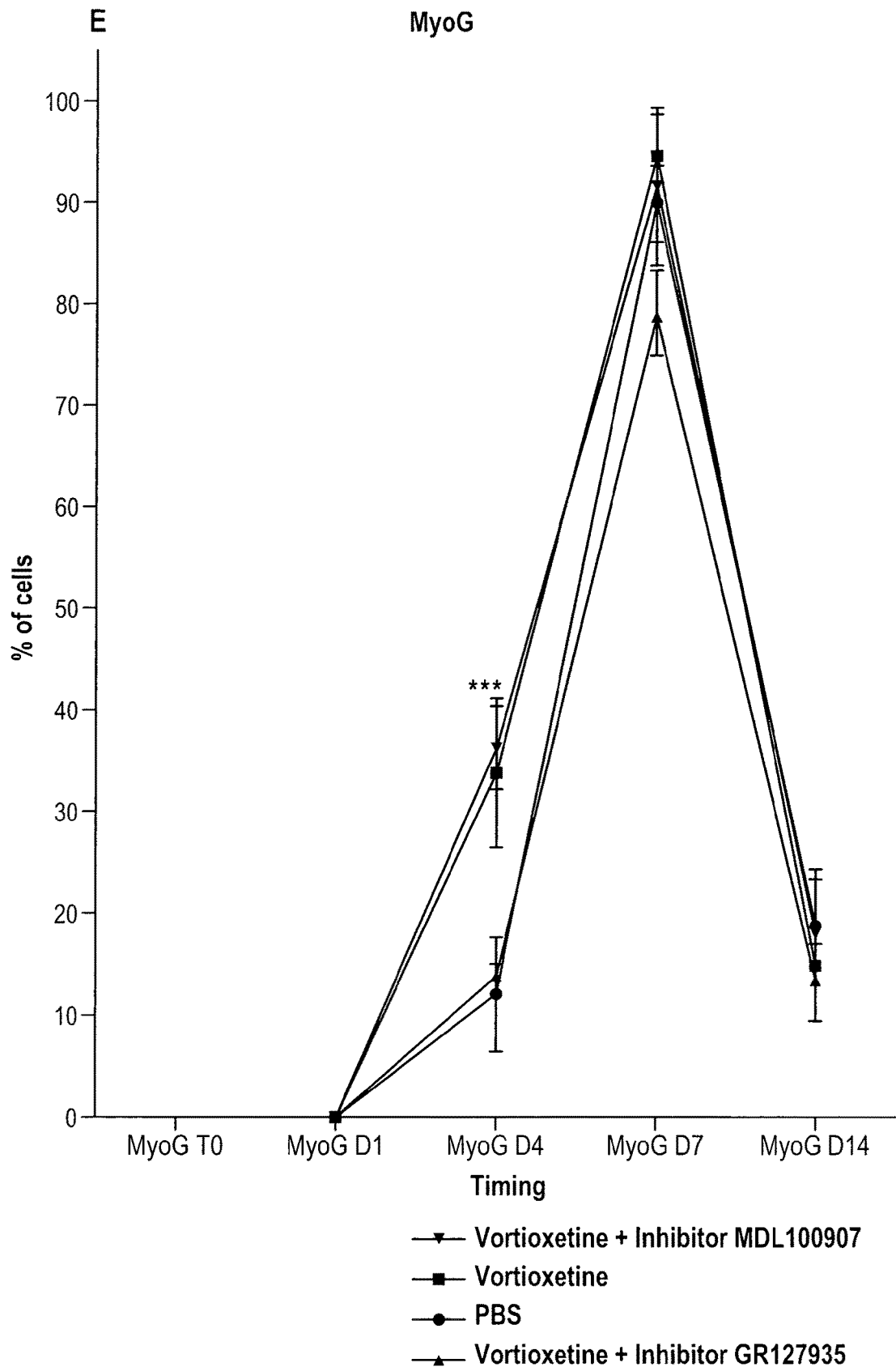

FIG. 11. Vortioxetine increases the number of vessels and the number of satellite cells in vivo and in vitro via the 5-HT1 B receptor. (a) Number of vessels counted on section per mm² with CD31 immunostaining after vortioxetine treatment of TgPax7nGFP mouse I.P treatment for 12 days at 20 mg/Kg. (b) Number of satellite cells counted by FACS per tibialis anterior after vortioxetine treatment of Tg:Pax7nGFP I.P treatment for 12 days at 20 mg/Kg. (c-e) Cells were sorted by FACS from Tg:Pax7nGFP mice and plated at 2000 cells per cm². The following day vortioxetine was added at 10 µM. At the indicated time points cells were fixed and stained for Pax7 (c), Myod (d), MyoG (e).

Figure 12:
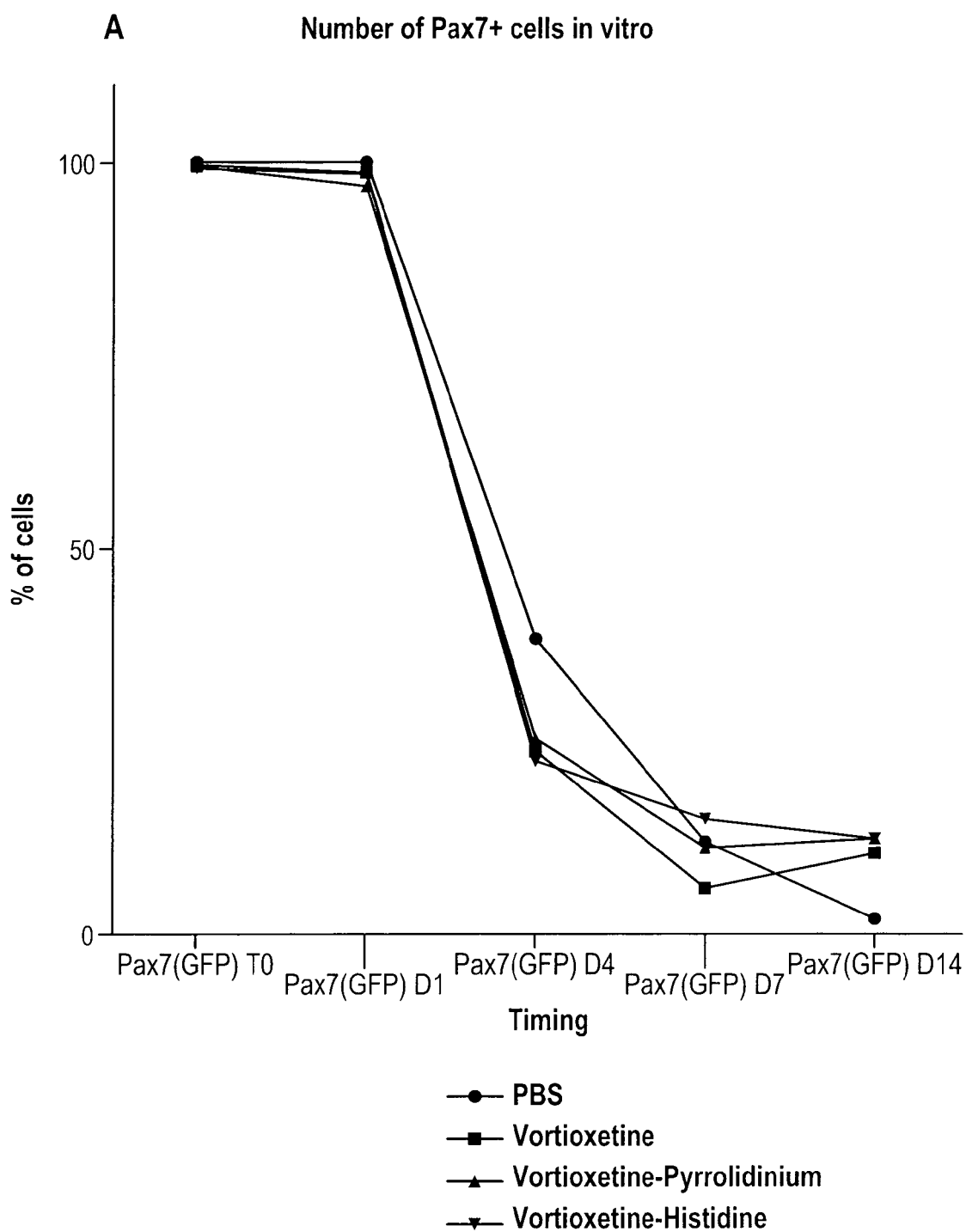
Figure 12:
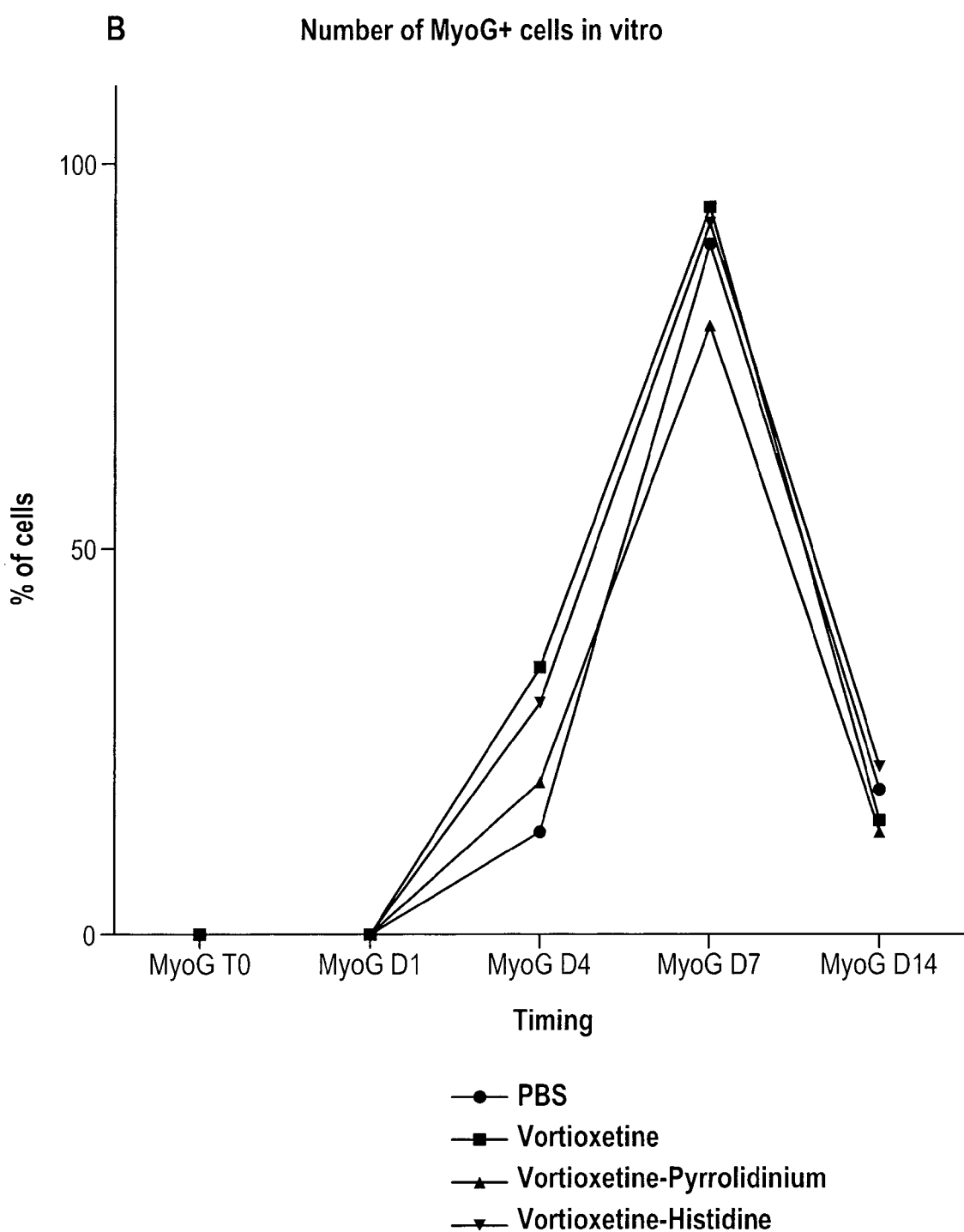
Figure 12:
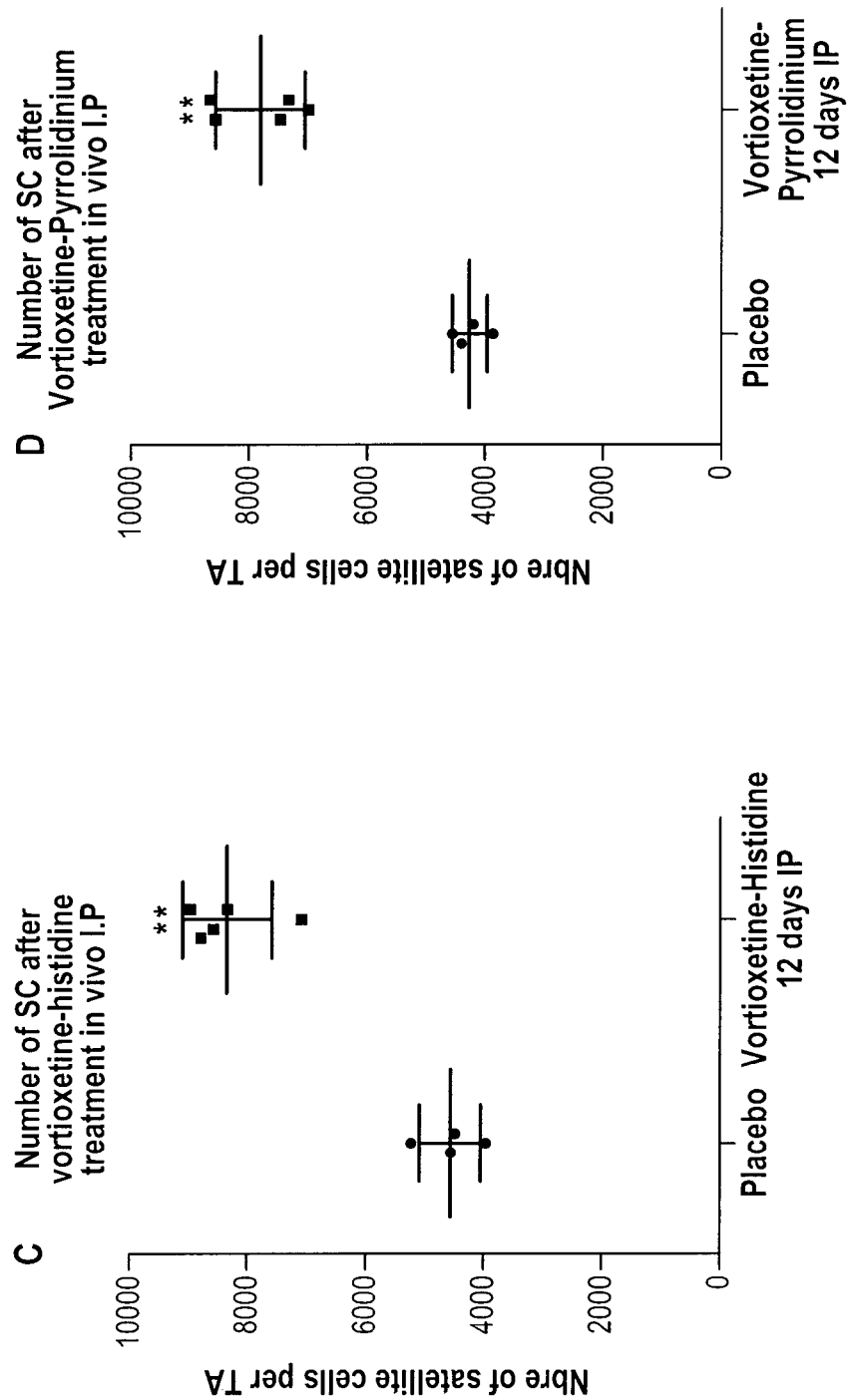

FIG. 12. Vortioxetine derivatives Histidine-vortioxetine and Pyrrolidinium-vortioxetine increases the number of vessels and satellite cells: (a-b) Cells were sorted by FACS from Tg:Pax7nGFP mice and plated at 2000 cells per cm². The following day Histidine-vortioxetine or Pyrrolidinium-vortioxetine were added at 10 µM (a) Percentage of Pax7+ cells at different time points in vitro with PBS or vortioxetine or Histidine-vortioxetine or Pyrrolidinium-vortioxetine. (b) Percentage of MyoG+ cells at different time points in vitro with PBS or vortioxetine or Histidine-vortioxetine or Pyrrolidinium-vortioxetine (c-d) PBS (n=4) or Histidine-vortioxetine (n=5) or Pyrrolidinium-vortioxetine (n=5) was injected IP to Tg:Pax7nGFP mice for 12 days at 20 mg/kg. Muscle (TA) were digested and counted by cytometry. (c) displays histidine-vortioxetine vs PBS injections (d) displays pyrrolidinium-vortioxetine vs PBS. Data are represented as mean±s.d. **$P<0.01$.

EXAMPLES

Fluoxetine, Vortioxetine and Derivatives Thereof Increase Muscle Stem Cell Number and Improve Regenerative Capacity of the Muscle 1. Material and Methods 1.1. Mice Injection and Injury All procedures in this study were approved by the Animal Care and Use committee at the Institut Pasteur (CETEA 2014-004). Unless specified 8 weeks old male mice were used in this study and housed on a 12:12 light/dark cycle in a pathogen free facility with controlled temperature and humidity. Food and drink were given ad libitum.

Animals were anesthetized with ketamine (Imalgene1000 100 mg/Kg Merial) and Xylazine (Rompun2% 20 mg/Kg Bayer) prior to injury. Animals were hydrated and treated with analgesic (Buprenorphin Axience 0.3 mg/kg) twice a day for 4 d following injury. For the injury, mice were anesthetized as previously described and 10µl of 12.5 µg/ml Notexin (Lotaxan) was injected in the Tibialis anterior. All protocols were reviewed by the Institut Pasteur, the competent authority, for compliance with the French and European regulations on Animal Welfare and with Public Health Service recommendations. This project has been reviewed and approved (#2013-0044) by the Institut Pasteur ethic committee (C2EA 89-CETEA).

Among the mice tested, Flk1$^{GFP/+}$ mice, in which green fluorescent protein (GFP) is targeted in VEGF-receptor-2 gene locus, and which exhibits a bright GFP signal in all endothelial cells, were kindly provided by Alexander Medvinsky (Institute for Stem Cell Research, University of Edinburgh, Edinburgh, UK).

1.2. Histological Analysis

Tibialis anterior (TA) was carefully dissected and snap frozen in liquid-nitrogen-cooled isopentane for a few minutes and stored at −80° C. prior to cryosectioning (10 µm sections). Sections were kept at room temperature overnight before staining. Sections were then rehydrated in PBS for 10 minutes and fixed in 10% formalin for 3 minutes. The sections were then routinely stained with haematoxylin and eosin (HE) using an automated stain machine or manually with red sirius.

The slides were assessed by double blinding and automated when possible (fibre diameter, cell count, infarcted area).

1.3. Immunostainings

Immunostaining was performed on cryosections fixed with 4% paraformaldehyde (PFA EMS #15710) in cold PBS, permeabilized with 0.5% Triton X-100 20 min at room temperature, washed, and blocked with 10% BSA for 30 min. Sections were incubated with primary antibodies overnight at 4° C. (see Table 1 below) and with Alexa-conjugated secondary antibodies 1/250 and Hoechst for 45 minutes. Sections were then analysed using an automated axioscan (Zeiss) or inverted Observer.Z1 Apotome (Zeiss). For apoptosis assessment, cells were collected in 2% serum, spun on polyD-lysine (Sigma-Aldrich #P6407), and immediately fixed with PFA 4%.

TABLE 1

List of antibodies used in the study.

| Antigen | Host | Concentration | References |
| --- | --- | --- | --- |
| Ly-6C (Gr1) | Rat | 0.5 µg/ml | Caltag LabRM3030 |
| CD31 | Rat | 15 µg/ml | BD Pharmingen 550274 |
| Pax7 | Mouse | 12 µg/ml | DSHB |
| Laminin | Rabbit | 0.69 µg/ml | Sigma-Aldrich L9393 |
| Secondary Donkey anti Rabbit (IgG Fraction Monoclonal | Variable according to the primary Ab host | 0.5 µg/ml | JacksonImmuno #711486152 (Rabbit) #200162037 (Mouse) |

1.4. Cell Sorting, Count and Culture

Muscle dissection was done as previously described in cold DMEM. Muscles were then chopped with small scissors and put in a 50 ml Falcon tube with collagenase 0.1% and trypsin 0.25% at 37° C. with gentle agitation. After 20 minutes, the supernatant was collected in 20% serum placed on ice, and the collagenase/trypsin solution was added to continue the digestion. Once muscle was completely digested, the solution was filtrated using 40 µm cell strainers. Satellite cells were cultured in 1:1 DMEM-Glutamax (Gibco #41965-039):MCDB201 (Sigma #M6770) containing 20% serum FBS (Biowest S1860). Medium was filtered using 0.22 µm filters. Cells were plated on Matrigel coating (BD Biosciences #354234) and kept in an incubator (37° C., 5% $CO_2$). For some in vitro experiments, plasma was extracted from fluoxetine or vortioxetine treated animals after 6 weeks by heart puncture followed by centrifugation at 1500 g for 15 min. The thus-obtained supernatant replaced FBS in the culture medium; the rest of the medium was unchanged.

For satellite cell counting, only the tibia/is anterior muscle was dissected and digested as described earlier, and the totality of the tube was analysed to assess the number of satellite cells per muscle. FACS analysis was done using a FACSasia (Beckman). All analyses and quantitation were performed using Summit v4.3 software from DakoCytomation and FloJo software. Cells were labelled with propidium Iodide 10 μg/ml (Sigma-Aldrich #P4170) to exclude dead cells and displayed using the PE (Phycoerythrin, Red) channel on the FACS profile.

1.5. Live Video Microscopy

Cells isolated by FACS were plated overnight on a 24-well glass bottom plate (P24G-0-10-F; MatTek) coated with matrigel (BD Biosciences #354234) and placed in an incubator in pre-equilibrated medium (1:1 DMEM Glutamax: MCDB [Sigma-Aldrich], 20% FCS (Biowest S1860). The plate was then incubated at 37° C., 5% $CO_2$ (Zeiss, Pecon). A Zeiss Observer.Z1 connected with a LCI PInN 10x/0.8 W phasell objective and AxioCam camera piloted with AxioVision was used. Cells were filmed for up to 5 days, and images were taken every 30 min with brightfield and phase filters and MozaiX 3×3 (Zeiss). Raw data were transformed and presented as a video.

1.6. Image Analysis

For image analysis (fibrosis quantification), ImageJ 1.46r software was using between 10 different photos randomly taken per section and 3 sections minimum per experimental group. The pictures were converted in a binary image and the pixel values then collected. For fibre size, the sections were immunostained with rabbit anti Laminin (Sigma-Aldrich #L9393) diluted at 1/200, overnight at 4° C. Secondary Donkey ant Rabbit 488 (DL488 JacksonImmuno #711486152) were used at 1/200 45 minutes at room temperature. The fibre perimeter was done automatically by using Pixcavator® software.

1.7. Luminex®(Multiplex Immunoassay)

Snap frozen plasma samples (n=6 per condition) were thawed out, and supernatant was processed for Luminex® multiple cytokine and chemokine analysis (Bio-Plex® Pro™ Mouse Cytokine Standard 23-Plex, Group I and Standard 9-Plex, Group II). Normalization was done by sample weight of frozen muscle.

1.8. RT-qPCR

Total RNA was isolated from cells using the RNAeasy Micro kit (Qiagen). The total RNA was reverse-transcribed using Superscript® III Reverse transcriptase (Invitrogen). Real-time quantitative PCR was performed using Power Sybr Green PCR Master Mix (Applied Biosystems) and the rate of dye incorporation was monitored using the StepOne™ Plus RealTime PCR system (Applied Biosystems). At least three biological replicates were used for each condition. Data were analyzed by StepOne Plus RT PCR software v2.1 and Microsoft excel. GAPDH transcript levels were used for normalisation of each target (=ΔCT). Real-time PCR $C_T$ values were analyzed using the 2-(ΔΔCt) method to calculate the fold expression (ΔΔCTmethod, Livak et al., 2001).

1.9. Force Measurement

The grip strength test is a non-invasive method designed to evaluate mouse muscle force in vivo. A grip meter (Bio-GT3, BIOSEB), attached to a force transducer, measures the peak force generated. Placebo and fluoxetine (6 weeks treatment) mdx mice were placed with the four paws on a grid and gently pulled backward until they released the grip. Five trials were conducted and, before statistical analysis, a mean value was calculated for each mouse using the tree median data. Results are expressed as the result of tree peak forces (in g), normalized to the body weight (in g).

1.10. Skinned Fibres Experiments

TA muscles were dissected from placebo and fluoxetine treated mice (6 weeks of treatment). Small bundles of two to five fibers were manually isolated from the muscles as previously described. Chemical skinning was carried out using Triton X-100. Skinned fibers were mounted in the Displacement Measuring System KD 2300 (model 0.5 SU, Kaman Instrumentation, Colorado Springs, Colo., USA). To perform force measurements, skinned fiber preparations were incubated for 1 h in relaxing solution (pCa 9.0, low calcium content) containing 1% Triton X-100 (v/v) to solubilize the sarcolemma and the sarcoplasmic reticulum membranes, and were subsequently washed several times in relaxing solution without detergent. Fibres were adjusted to slack length and then stretched progressively until the tension developed became maximal. Isometric tension was recorded continuously using a chart recorder (model 1200, Linear, Reno, Nev., USA). The tension obtained was normalized to fibre cross-sectional area.

1.11. Statistical Analysis

Statistical analysis was performed using GraphPad Prism software using appropriate tests (non-parametric Mann-Whitney unless specified) and a minimum of 95% confidence interval for significance; p values indicated on figures are <0.05 (*), <0.01 (), and <0.001 (*). Figures display average values of all animals tested±SD or ±SEM for RT-qPCR, or as indicated.

2. Results

2.1. Fluoxetine

Figure 1:
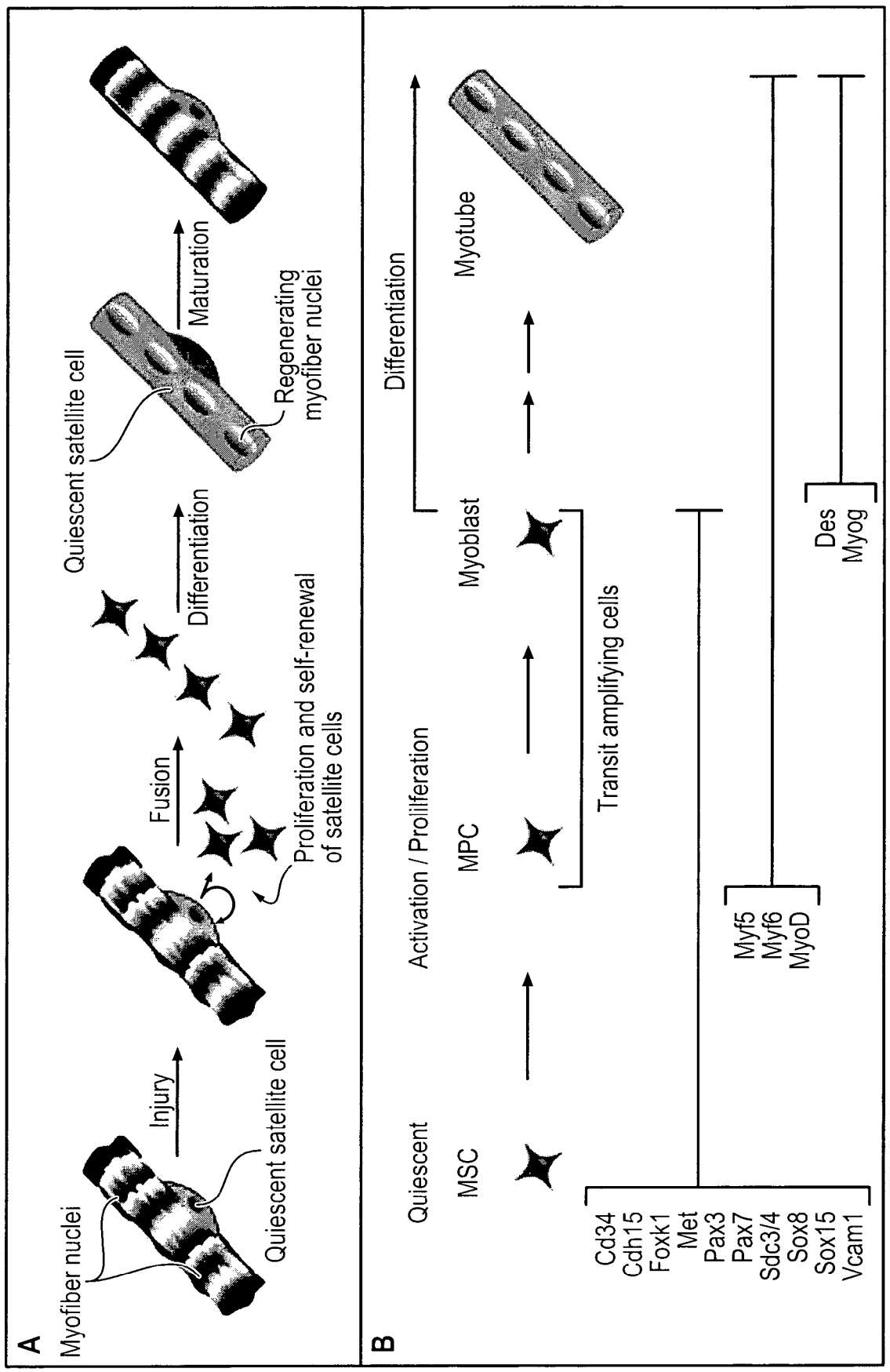
FIG. 1. Key gene markers expressed in satellite cells (MSC) and progenitor cells (MPC) of adult skeletal muscle (extract from Shi et al., 2006).
Figure 2:
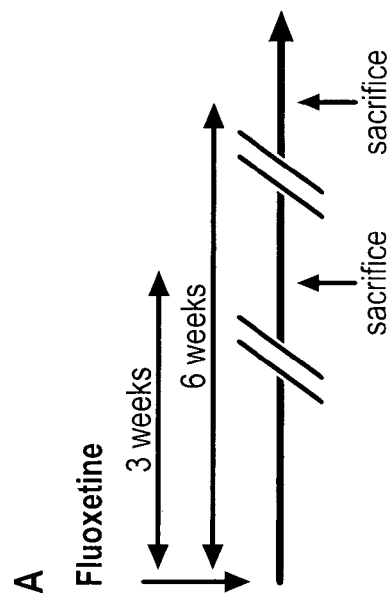
FIG. 2. Fluoxetine increases the vessel number and the satellite cell (SC) number in skeletal muscle (a) Schematic representation of fluoxetine delivery and sacrifice time points. (b) Number of satellite cells per $mm^2$ on section. (c-d) Histological section of tibialis anterior of a placebo treated mouse (c) and fluoxetine treated TgPax7nGFP mouse (d). The arrows point to the satellite cells. (e) Number of vessels per $mm^2$ after intra peritoneal (IP) or per os administration of fluoxetine at different time points. (f-g) Histological section of tibialis anterior of a placebo (f) and fluoxetine treated (g) Flk1$^{GFP/+}$ mouse. The picture displays endogenous GFP. (h) Number of CD31+ cells in Matrigel plugs subcutaneously grafted in placebo and fluoxetine treated mice. (i-j) Representative image of a Matrigel plug after 6 weeks in a C57Bl/6 mouse treated with placebo (i) or fluoxetine (j). (k-l) Representative image of a vessel (arrows) in the Matrigel plug detected by HE staining in placebo (k) or fluoxetine (l) treated mice. (m) Vessel length 4 days post-plating of Cytodex® beads covered with HUVEC. (n) Representative image of a Cytodex® bead 4 days-post plating in presence of placebo plasma. (o) Representative image of a Cytodex® bead 4 days-post plating in presence of fluoxetine treated mouse plasma.
Figure 2:
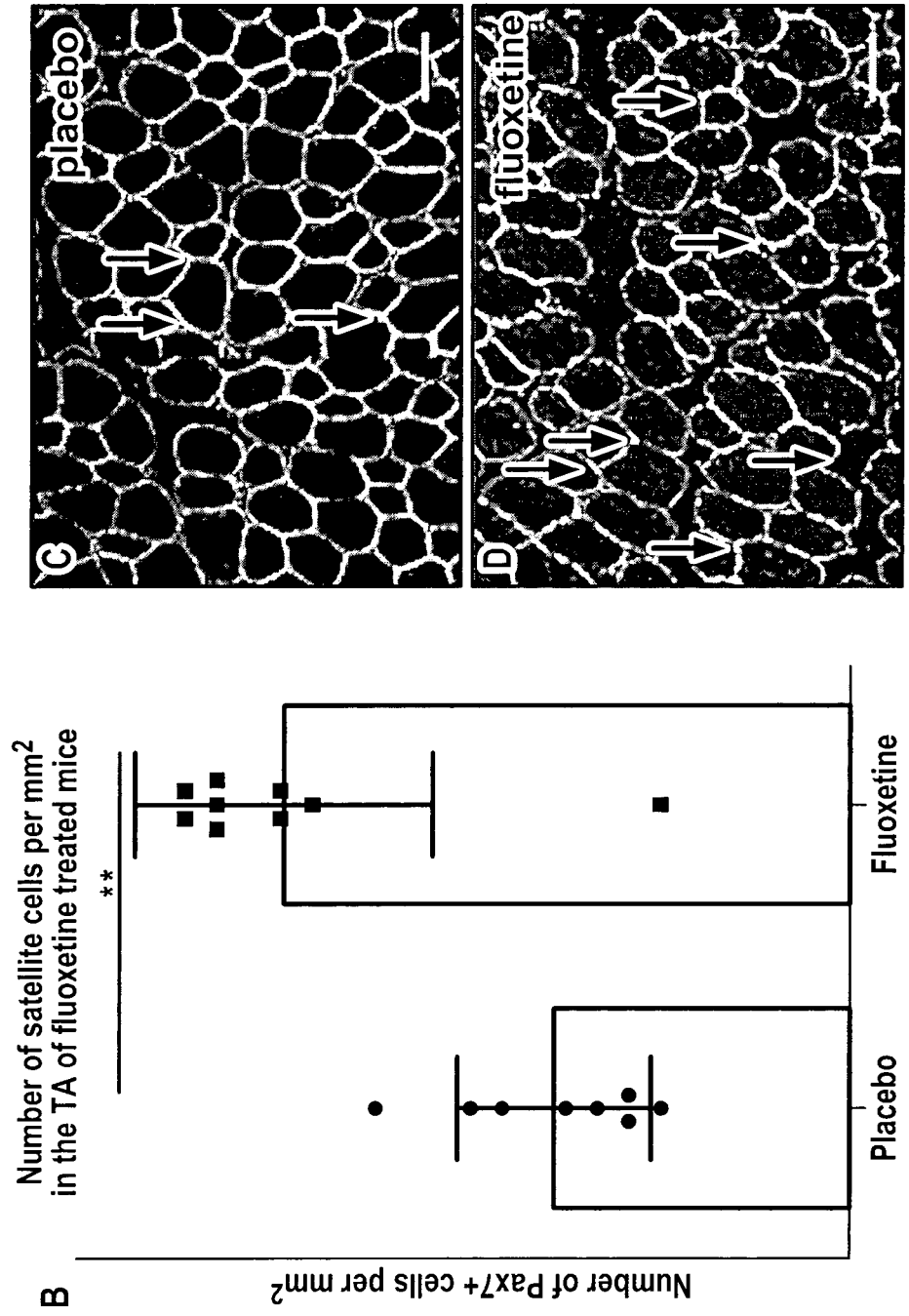
Figure 2:
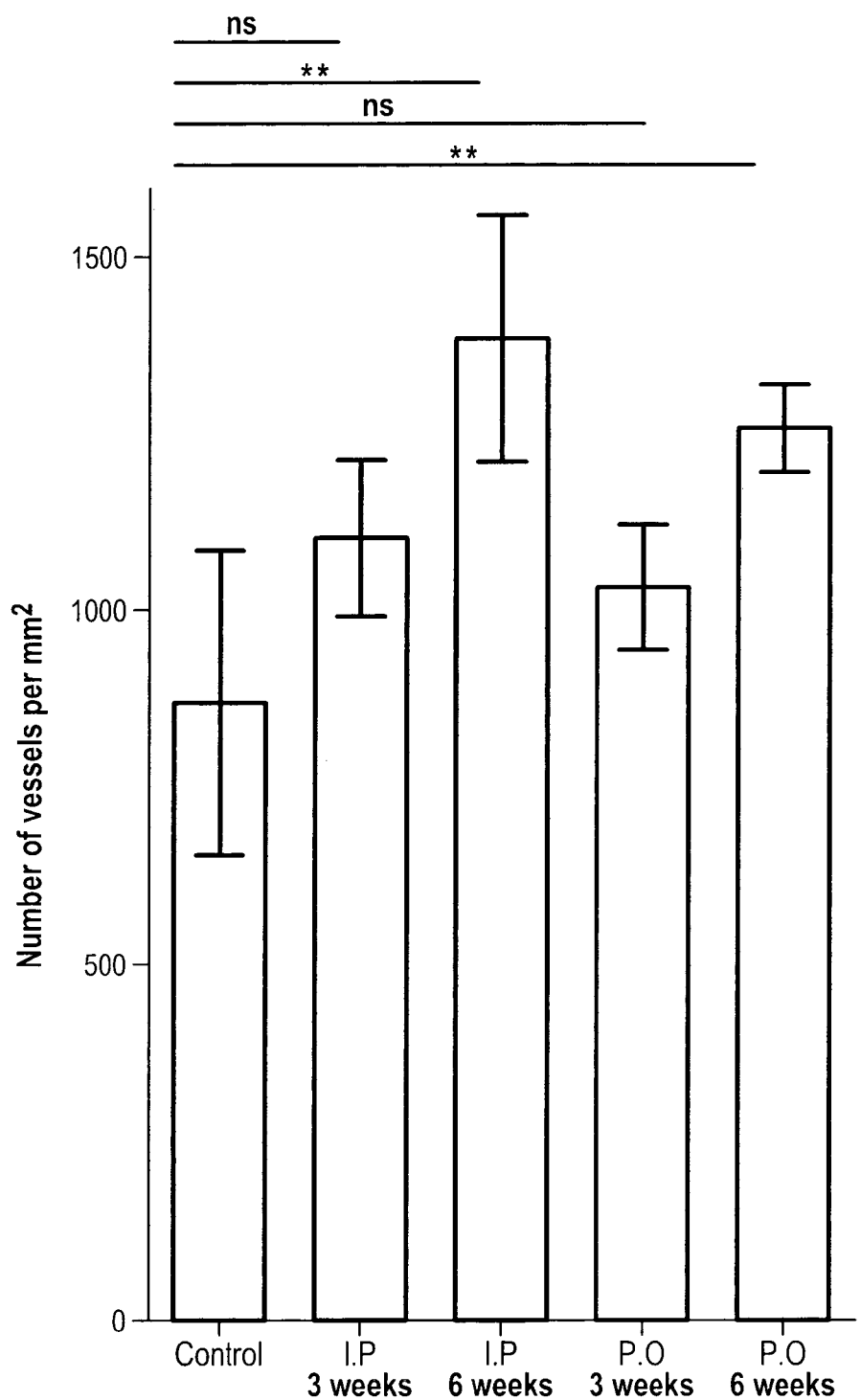
Figure 2:
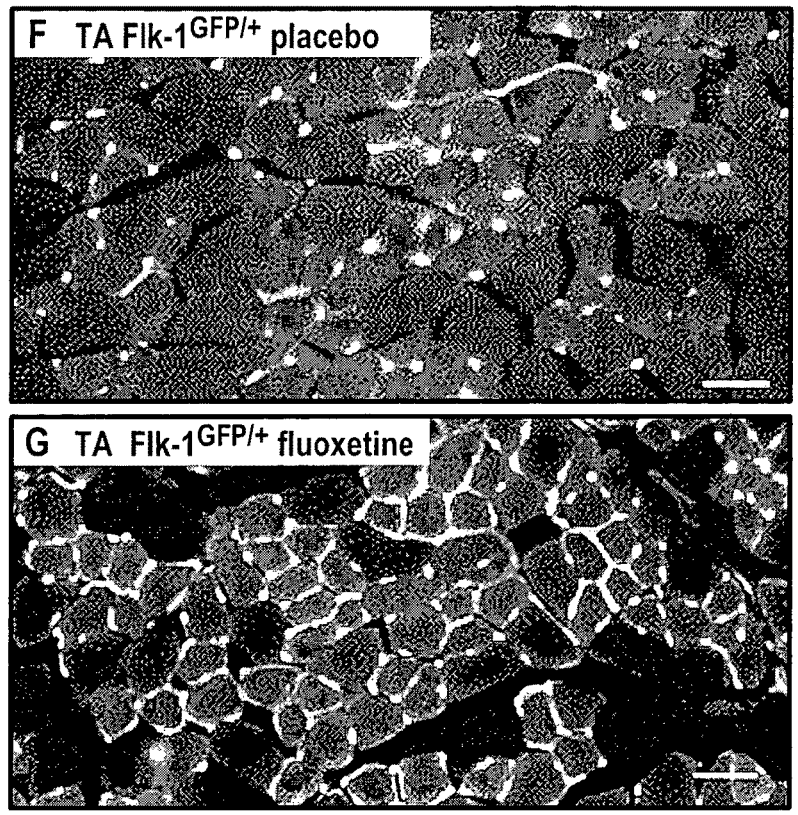
Figure 2:
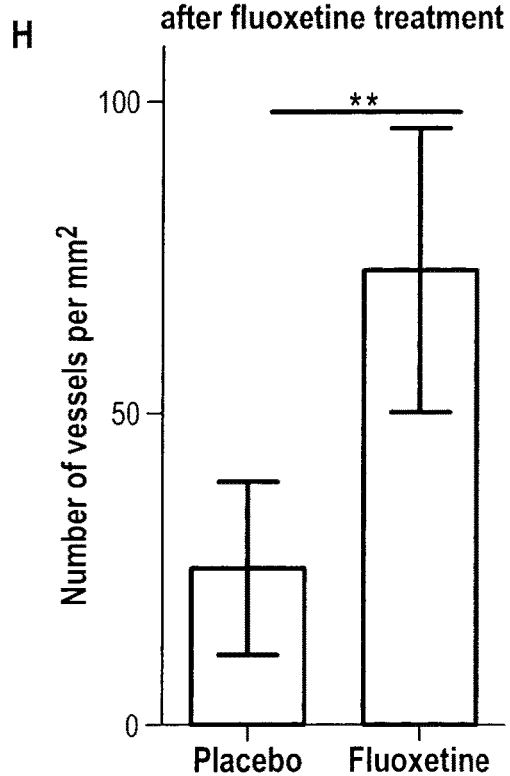
Figure 2:
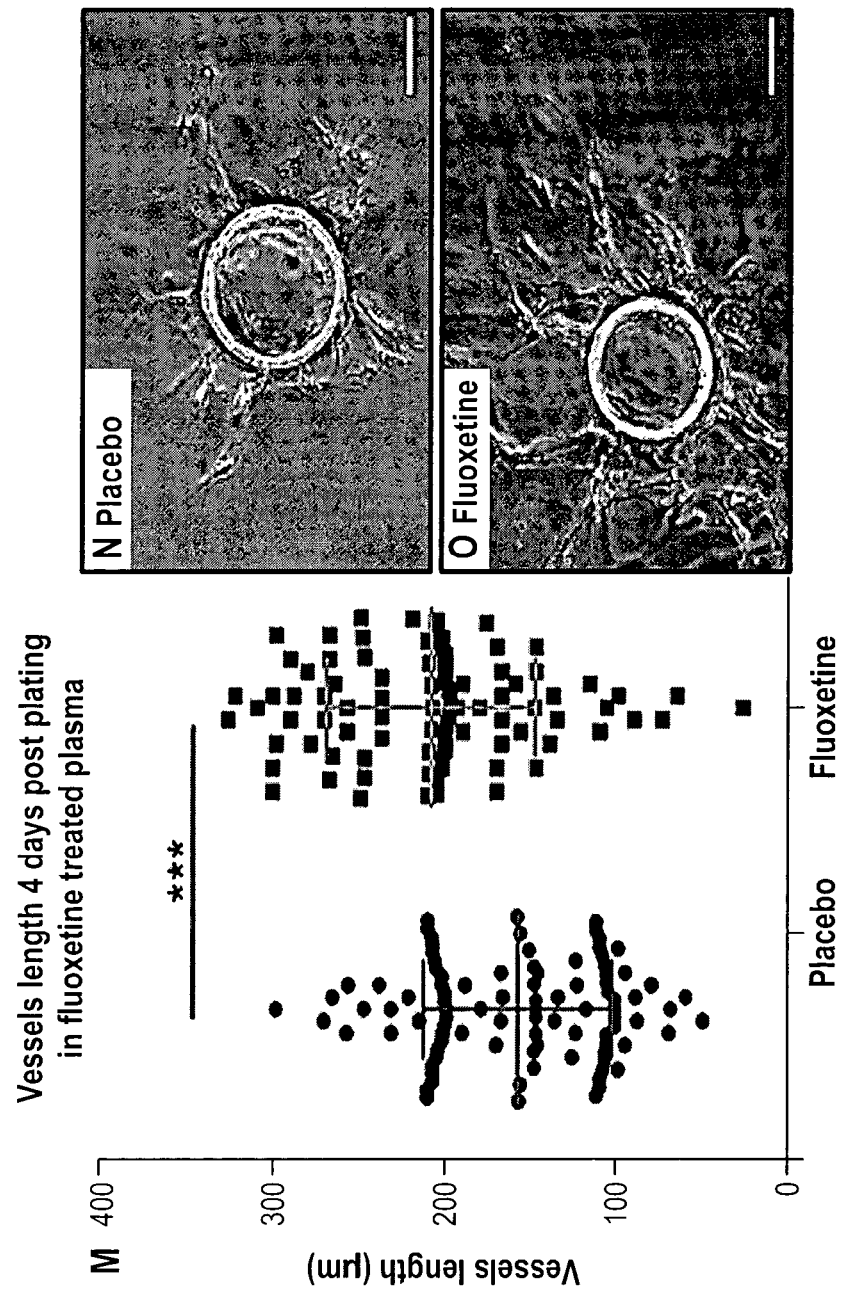
Figure 2:
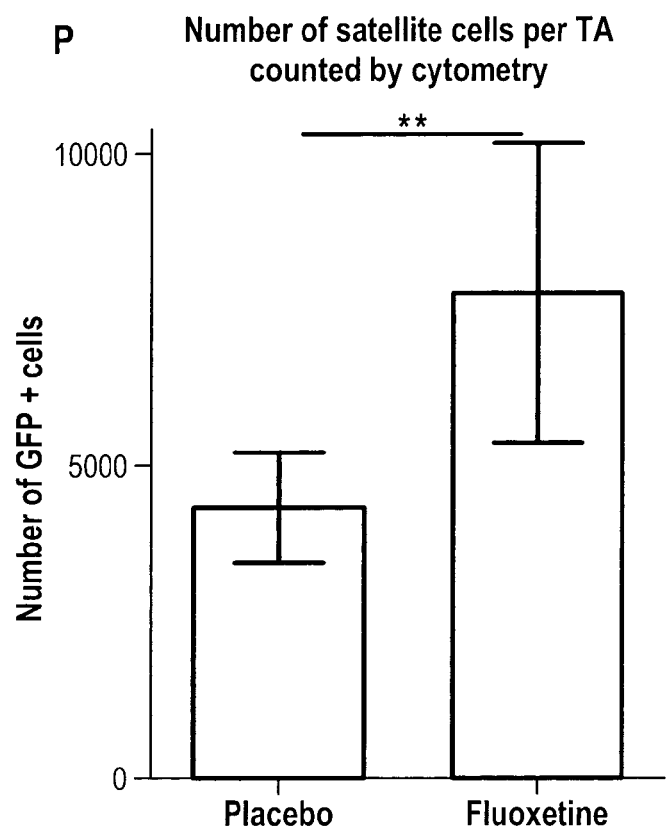
Figure 2:
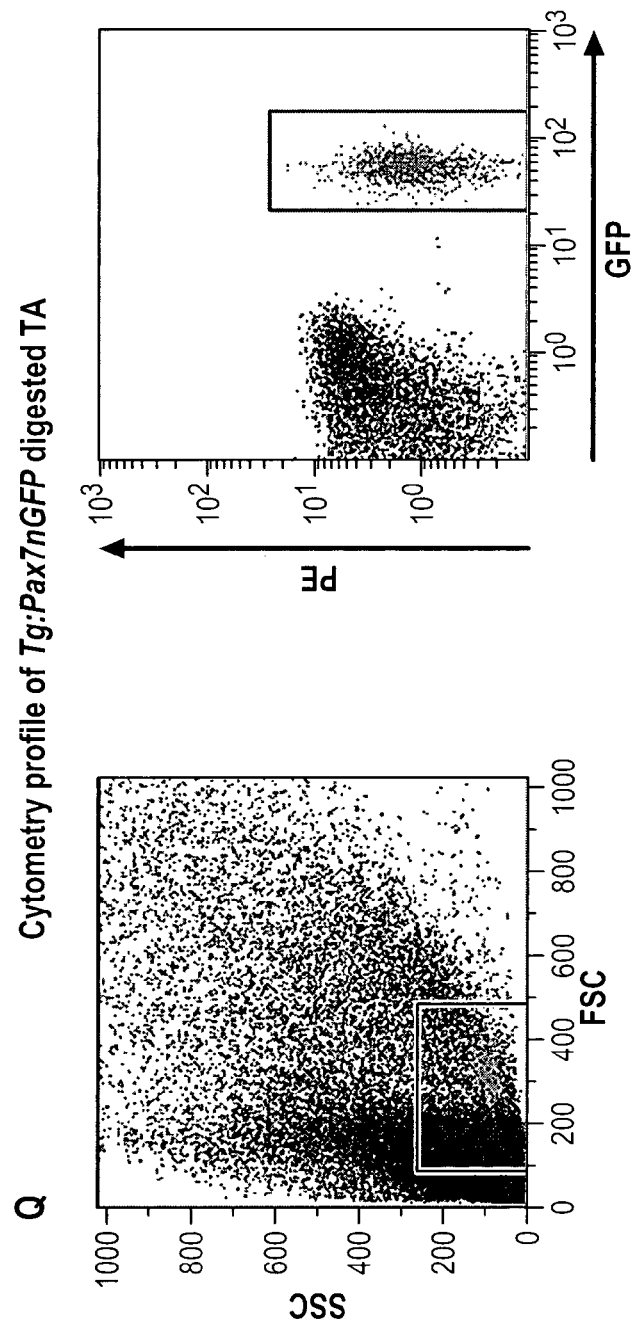
Figure 2:
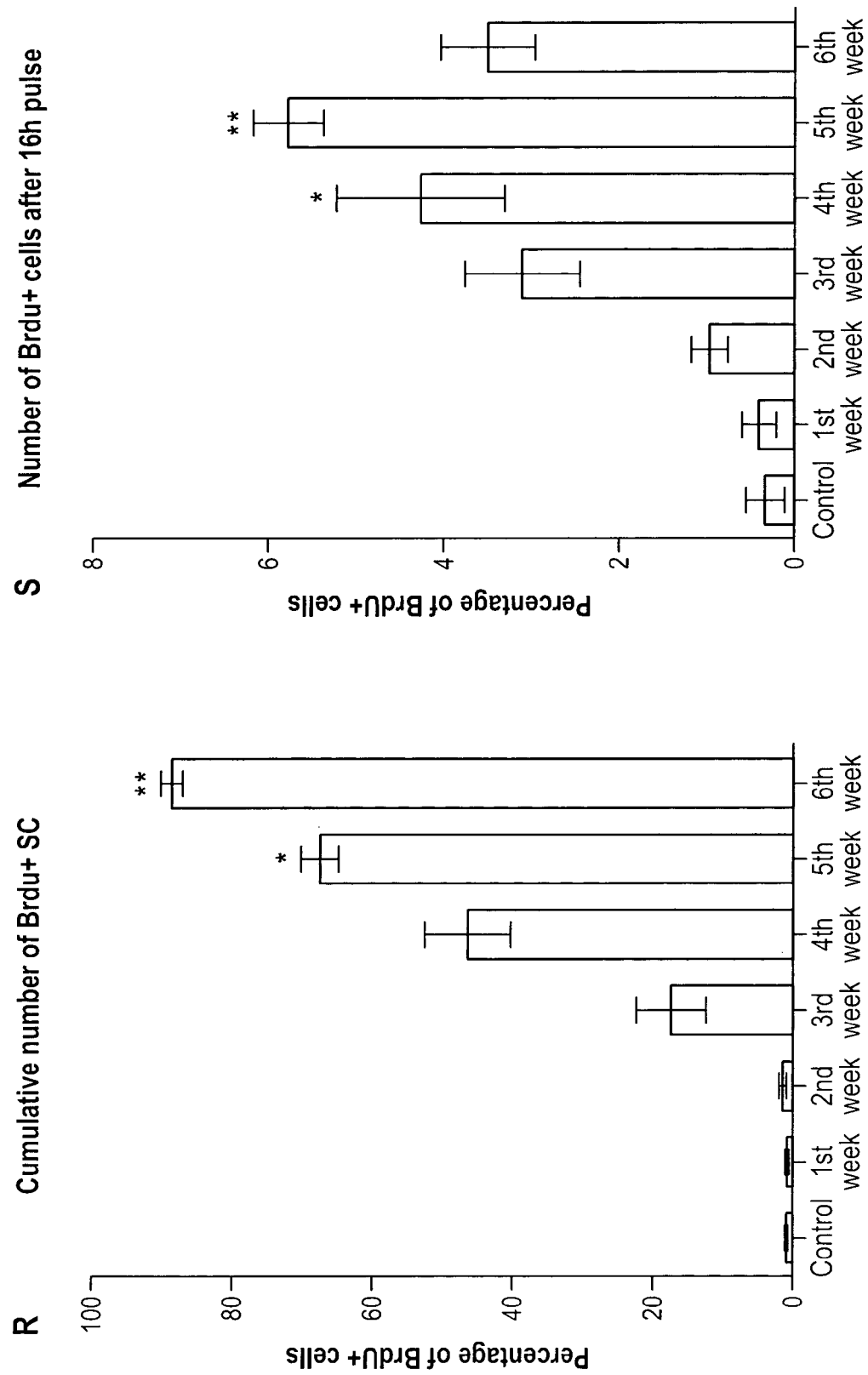
Figure 2:
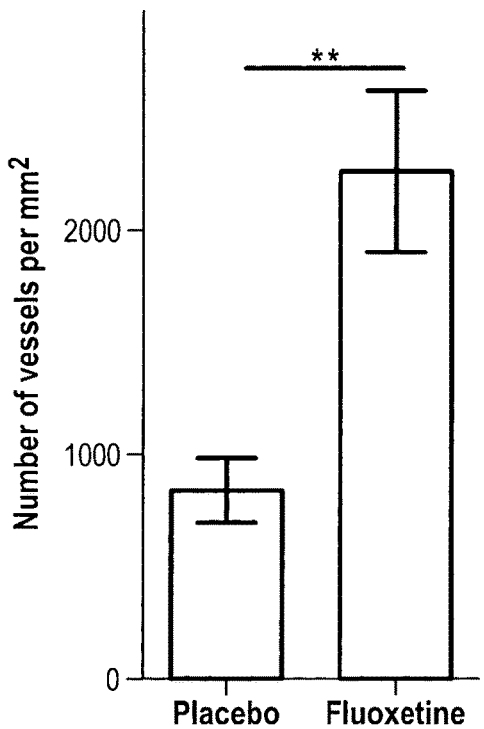
Figure 2:
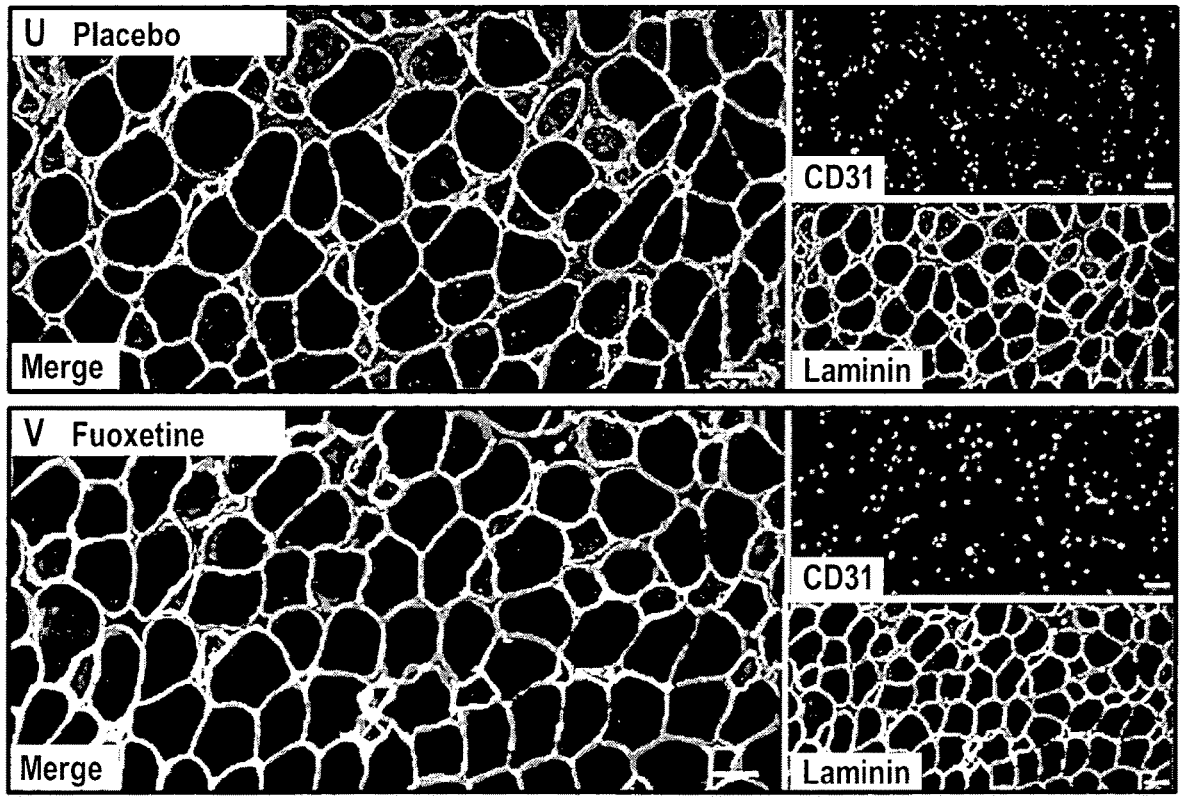

2.1.1. Fluoxetine Increases Vessel Number and Satellite Cells Number in the Skeletal Muscle In order to investigate the effect of fluoxetine on vessels number, intra peritoneal (I.P) or per os (P.O) administration of 18 mg/kg of fluoxetine was performed for either 3 or 6 weeks to Flk1$^{GFP/+}$ or TgPax7nGFP mouse (FIG. 2a), allowing the direct visualisation of endothelial cells and satellite cells (SC) respectively. Throughout the study, focus was made on the tibialis anterior (TA). In skeletal muscle, SC are central for muscle repair. By histological count, it was observed that the number of SC was higher when treated with fluoxetine (9.7±3.1SC per mm$^2$ in the placebo vs. 16.3±5.4SC in the treated, p=0.04) (FIGS. 2b-d and p-q). These results were confirmed by digesting the TA and counting the number of SC directly by cytometry using the Tg:Pax7nGFP mouse (Sambasivan et al., 2009) (p=0.02) (FIGS. 2p,q). SC are localized close to capillaries and angiogenesis is known to be crucial for muscle repair SC survival with cellular interplays between vessel cells and SC. The number of vessels was therefore quantified. In control Flk1$^{GFP/+}$ mouse (placebo), the number of vessels was of 870±213.1 vessels per mm$^2$ and increased after 3 weeks of I.P treatment (1103±110.2 vessels per mm$^2$), and even more after 6 weeks (1384±175.3 vessels per mm$^2$, p=0.008) (FIG. 2e). Neovessels presented with normal histological appearance associating a basal lamina and a permeable lumen sometimes containing red blood cells. The daily administration of fluoxetine I.P might cause unwanted peritoneal inflammation that could interfere with angiogenesis since inflammation and neovascularization are intertwined in some models (Sadat et al., 2014). Therefore, fluoxetine was administered P.O for 6 weeks: a similar increase in the number of vessels was observed (1256±62.2 vessels per mm$^2$ p=0.008, FIG. 2e-g). Those results were confirmed in another model, by administrating fluoxetine to C57Bl/6 mice P.O for 6 weeks and performing immuno-labelling of CD31+ cells on cryo-sectioned TA. 841±137 CD31+ cells per mm$^2$ were counted in the placebo-treated mice vs. 2260±361 CD31+ cells per mm$^2$ in the fluoxetine-treated mice, p=0.008 (FIG. 2t-v), confirming the previous observation. After delivery of fluoxetine 6 weeks in vivo the levels of IL-la, IL-1b, IL-2, and eotaxin are downregulated whereas IL-4 and IL-13 are upregulated (p=0.02). The other tested cytokines did not show any significant changes (Table 2).

TABLE 2

Fluoxetine decreases the basal levels of cytokines. The table below represents the plasmatic levels of cytokines in picograms per μl of plasma measured by Luminex ® assay in the placebo and fluoxetine treated mice.

| Cytokine | Quantity in Placebo (pg/μm) | Quantity in Fluoxetine treated (pg/μm) | Statistically significant | p value |
|---|---|---|---|---|
| IL-1a | 234.2 ± 33 | 150.8 ± 22.8 | * | 0.02 |
| IL-1b | 1398 ± 380 | 756.2 ± 205 | * | 0.02 |
| IL-2 | 48.30 ± 8.1 | 82.53 ± 11.7 | * | 0.02 |
| IL-4 | 52.71 ± 6.7 | 93.76 ± 9.9 | * | 0.02 |
| IL-5 | 21.13 ± 16.7 | 7.2 ± 3.2 | ns | 0.06 |
| IL-6 | 20.54 ± 8.4 | 10.68 ± 1.8 | ns | 0.11 |
| IL-9 | 89.02 ± 15.5 | 72.54 ± 14.8 | ns | 0.11 |
| IL-10 | 16.10 ± 7.8 | 36.60 ± 27.9 | ns | 0.34 |
| IL-12(p40) | 43.7 ± 43 | 59.7 ± 36 | ns | 0.48 |
| IL-12(p70) | 130.1 ± 53.7 | 118.2 ± 40 | ns | 0.48 |
| IL-13 | 626.6 ± 69.8 | 875.1 ± 147 | * | 0.03 |
| IL-17 | 48.3 ± 22.2 | 29.8 ± 15.3 | ns | 0.34 |
| Eotaxin | 44.10 ± 19 | 18.7 ± 4.6 | * | 0.02 |
| G-CSF | 3884 ± 1657 | 3066 ± 288 | ns | 0.8 |
| GM-CSF | 29189 ± 39901 | 8800 ± 1438 | ns | 0.34 |
| IFN-g | 32.78 ± 6.1 | 28.5 ± 8.9 | ns | 0.2 |
| KC | 8290 ± 10202 | 717 ± 502 | ns | 0.11 |
| MCP-1 | 73.5 ± 45.9 | 26.6 ± 20 | ns | 0.06 |
| MIP-1a | 64.6 ± 39 | 34.6 ± 17.3 | ns | 0.48 |
| MIP-1b | 570.4 ± 154 | 442.1 ± 49 | ns | 0.11 |
| RANTES | 120 ± 11 | 53.6 ± 27.1 | ns | 0.34 |
| TNF-a | 8318 ± 865 | 7846 ± 2171 | ns | 0.34 |
| FGF-basic | 1057 ± 141.3 | 1276 ± 618 | ns | 0.88 |
| MIG | 100 ± 8.1 | 83.4 ± 11 | * | 0.05 |
| PDGF-bb | 653 ± 256 | 401 ± 74 | ns | 0.34 |
| VEGF | 313.44 ± 91 | 2554 ± 1041 | * | 0.02 |

The p value is calculated using Mann-Whitney test.
n = 7 animals per condition.
*: p ≤ 0.05;
ns: non-statistically significant.

To further confirm the above results, an ex vivo Matrigel angiogenesis assay was used. To do so, a cold Matrigel was introduced subcutaneously, which solidifies and allows the penetration by host cells and the formation of new blood vessels in C57Bl/6 treated P.O for 6 weeks. The number of CD31 expressing cells was higher in the fluoxetine treated plugs (72.9±22.6 CD31+ cells per mm$^2$) compared with the placebo (25.20±13.8 CD31+ cells per mm$^2$, p=0.002) (FIGS. 2h-l); confirming the previous observation.

These data were further confirmed by in vitro HUVEC assay (human endothelial cells). C57Bl/6 mice were treated P.O for 6 weeks and plasma was extracted from blood. HUVEC cells were then plated on cytodex beads and cultured in either of the plasma. The growth of HUVEC incubated with plasma coming from treated animals was faster 4 days post plating (p≤0.0001) (FIGS. 2m-o).

Cell division was quantified after BrdU administration during the entire per os treatment with fluoxetine, and the results showed that 90% of the SC population was dividing (FIG. 2r). A short pulse of BrdU 16 h before death showed that most of the SCs were dividing between the third and the fifth week (FIG. 2s).

2.1.2. Fluoxetine Improves Muscle Regeneration Potential

To investigate if fluoxetine had a functional impact on muscles, notexin injury was performed after fluoxetine treatment (FIG. 3a) and the muscle ability to regenerate on Tg:Pax7nGFP mice was investigated (Sambasivan et al., 2009). The comparison 4 days and 14 days post injury of the muscles showed in both cases a better regeneration (FIG. 3b-j). Indeed, major differences were observed in the muscle regeneration features between placebo and fluoxetine treated mice. At 4 days post-injury treated animals showed a higher number of SC (459±283 in the treated vs. 177.2±49 in the placebo, p=0.04) (FIG. 3b-d) and more cells were already differentiating (p=0.0006) (FIG. 3e-g). 14 days post-injury in the placebo group, regenerating centro-nucleated fibers showed variable size (anisocytosis, 81±28.4 μm$^2$), multifocal endomysial infiltration by mononuclear inflammatory cells (9.14±3.9 Gr1+ cells and 12.6±3.9 F4/80+ cells per section), the presence of multiple large basophilic foci of calcium deposition (19±4 per mm$^2$), and mild fibrosis of the endomysium (6.4±2% of total muscle area) (FIGS. 3h-k). By contrast, in fluoxetine treated mice, regenerating fibers were bigger and showed less variable size (129±12.6 μm$^2$, p=0.005), less inflammatory cells (4.1±2.6 Gr1+ cells; p=0.018 and 4.7±2.7 F4/80 cells; p=0.0017), less calcium deposits (3.2±3 per mm$^2$ p=0.0006), and less endomysial fibrosis (2.2±0.7 of total muscle area p=0.007) (FIGS. 3h-k, and FIGS. 4a-d)). The number of fibers however remained the same (p=0.4, FIG. 4e). Twenty-eight days post-injury, the muscle was fully regenerated; no differences were observed between the two groups, except for a higher number of vessels (p=0.036) and SC (p=0.076) in fluoxetine treated animals (FIGS. 4f,g). These data were confirmed in vitro by plating SC from Tg:Pax7nGFP mouse in 20% plasma originating from C57Bl/6 treated mice or placebo. By live-videomicroscopy, it was observed that the first satellite cells division occurred faster (26.45 h±1.18 post-plating in fluoxetine treated plasma vs. 29.08 h±0.37 in control plasma p=0.02, with higher division rate (12.5±2.1 h in placebo vs. 8.7±0.7 h in fluoxetine; p=0.047) (FIGS. 4i,j). A higher number of myogenine positive cells 4 days post-plating was also observed (12±5.5% of total plated cells in the placebo vs. 34.75±6.3% in the fluoxetine treated; p=0.02, (FIG. 4k) as well as faster forming myofibers; confirming the observations made in vivo of a faster differentiation and repair of muscle fibers. Interestingly, together with this improved regeneration, a decrease in the inflammation of the muscle after injury was observed as previously (Table 3). For example, the pro-inflammatory cytokine IL-6 dropped from 4258±665pg/μl in the injured vs. 2459±920 pg/μl in the injured with fluoxetine treatment (p=0.02).

To further challenge the muscle, several rounds of injury were performed after fluoxetine treatment, in order to exacerbate the phenotype and insure that the satellite cells (SC) pool was not exhausted. The number of SC remained constant per TA even after 3 rounds of injury (FIG. 4h). At the histological level the muscle was well regenerated in the injured and re-injured cases (FIG. 3l), showing that the SC were still functional stem cells after fluoxetine treatment.

TABLE 3

Fluoxetine decreases the levels of cytokines after injury. The table represents the plasmatic levels of cytokines in picograms per µl of plasma measured by Luminex ® assay in the placebo and fluoxetine treated and notexin injured mice.

| Cytokine | Quantity in placebo 4 days PI (pg/µm) | Quantity in fluoxetine 4 days PI treated (pg/µm) | Statisifically significant | P value |
|---|---|---|---|---|
| IL-1a | 307.6 ± 180 | 107.6 ± 33.2 | * | 0.05 |
| IL-1b | 3698 ± 2202 | 2039 ± 435 | ns | 0.34 |
| IL-2 | 206.5 ± 187 | 47.33 ± 15 | * | 0.03 |
| IL-4 | 156.1 ± 52 | 303.9 ± 5 | * | 0.02 |
| IL-5 | 566 ± 82 | 265 ± 41 | * | 0.02 |
| IL-6 | 4258 ± 665 | 2459 ± 920 | * | 0.02 |
| IL-9 | 426.3 ± 89 | 241 ± 56 | * | 0.02 |
| IL-10 | 342 ± 36 | 176 ± 39 | * | 0.03 |
| IL-12(p40) | 336 ± 179 | 171 ± 84 | ns | 0.2 |
| IL-12(p70) | 987.2 ± 693 | 359 ± 240 | ns | 0.11 |
| IL-13 | 2028 ± 1242 | 691 ± 268 | * | 0.02 |
| IL-17 | 1800 ± 1075 | 1558 ± 525 | ns | 0.8 |
| Eotaxin | 10155 ± 6873 | 3692 ± 934 | ns | 0.11 |
| G-CSF | 7014 ± 7628 | 2689 ± 364 | ns | 0.34 |
| GM-CSF | 30928 ± 49630 | 3962 ± 2289 | ns | 0.2 |
| IFN-g | 149.2 ± 35.72 | 68.84 ± 44.6 | * | 0.02 |
| KC | 8290 ± 10202 | 717 ± 502 | * | 0.05 |
| MCP-1 | 21380 ± 21143 | 6560 ± 7168 | * | 0.05 |
| MIP-1a | 2492 ± 784 | 4214 ± 4861 | ns | 0.68 |
| MIP-1b | 1770 ± 1034 | 1337 ± 540 | ns | 0.68 |
| RANTES | 4658 ± 1870 | 2804 ± 826 | * | 0.05 |
| TNF-a | 7846 ± 2171 | 10386 ± 1266 | * | 0.02 |
| FGF-basic | 1115 ± 117 | 1618 ± 232 | * | 0.02 |
| MIG | 45730 ± 41234 | 28105 ± 38006 | ns | 0.2 |
| PDGF-bb | 2965 ± 317.6 | 1777 ± 148.5 | * | 0.02 |
| VEGF | 653.4 ± 203 | 3334 ± 59 | * | 0.02 |

The p value is calculated using Mann-Whitney test.
n = 4 animals used per condition.
PI: post-injury;
*: $p \leq 0.05$
ns: non-statistically significant.

2.1.3. Effects of Fluoxetine on Vessels and Satellite Cells is Obtained Through Stimulation of the 5-HT1 B Serotonin Receptor In order to understand how vessels were activated, endothelial cells (CD34+, CD31+, Sca-1+, CD45−) from digested muscle were FACS cell-sorted after 6 weeks P.O fluoxetine treatment (FIG. 5a). RT-qPCR was then performed on serotonin receptors subtypes to further characterize by which the endothelial cells could be activated (FIG. 5b). A 90±35 fold increase was observed in the 5-HT1 BR subtype in the treated vs. placebo mice (p=0.0035), and 30±13 (p=0.015) fold increase in 5-HT2 BR subtype in the fluoxetine treated animals (FIG. 5b). The other tested subtypes (5-HT1 AR, 5-HT1 DR, 5-HT1 FR, 5-HT2 AR, 5-HT2 CR) showed non-statistically significant increase (FIG. 5b). These data were confirmed using endothelial markers from digested muscle after 6 weeks P.O fluoxetine treatment (data not shown). The same observation was made in FACS cell-sorted SC from Tg:Pax7nGFP mice (FIG. 5b).

To investigate the role of the 5-HT1 BR, the GR127935 hydrochloride inhibitor (a 5-HT1 BR antagonist) was delivered in osmotic pump together with fluoxetine treatment P.O for 6 weeks and vessel count in Flk1$^{GFP/+}$ mice and SC count in Tg:Pax7nGFP mice were performed. The number of vessels was lower in fluoxetine and inhibitor treated Flk1$^{GFP/+}$ mice (1028±173 vessels per mm$^2$) compared with fluoxetine and PBS treated Flk1$^{GFP/+}$ mice (1949±576 vessels per mm$^2$, p=0.0159) (FIGS. 5i-k). The number of SC was also lower in fluoxetine and inhibitor treated Tg:Pax7nGFP mice (4674±1414 SC per TA) compared with fluoxetine and PBS treated Tg:Pax7nGFP mice (7283±2325 SC per TA p=0.04) (FIGS. 5f-h). Although a 30 fold increase of 5-HT2 B receptor was detected after fluoxetine treatment, no inhibition of fluoxetine effects were observed when antagonizing it with MDL100907 (a 5-HT2 BR antagonist) (FIGS. 6f,g).

After injury, the inhibition of 5-HT1 BR by GR127935 suppressed the beneficial effects of fluoxetine treatment with a lower number of SC (FIG. 6a) and differentiating cells (FIG. 5c), a lower fiber size (FIG. 5D) and higher calcium deposits (FIG. 6B) 14 days post-injury, a higher percentage of fibrosis (FIG. 5e) and a higher infiltration of immune Gr1 and F4/80 cells (FIG. 6c,d). After injury, the inhibition of 5-HT2 BR by MDL100907 did not suppress the beneficial effects of fluoxetine (FIG. 6e).

Those results were confirmed in vitro (FIG. 7a). The number of Pax7 positive cells decreased faster 4 days post-plating in plasma from fluoxetine treated animals (24%±6 in fluoxetine treated vs. 39.25%±8 in placebo p=0.02) (FIG. 7b) and was close to the one of the placebo when incubated with GR127935 (35.25%±6.2 p=0.32) (FIG. 7b). 14 days post-plating, a higher number of reserve cells (Pax7 positive cells that are quiescent in vitro) was detected in the plasma from fluoxetine-treated animals (9.4%±0.7) than in the placebo treated animals (4.4%±0.7, p=0.01), and when GR127935 was added in vitro the number of reserve cells dropped (4.5%±0.5, p=0.9) (FIGS. 7b,c). MyoD (an activation marker) expression did differ at any time investigated in the 3 tested conditions (FIG. 7d), however Myogenin (MyoG), a differentiation marker displayed a 3 times increase in expression when plated with plasma coming from fluoxetine-treated mice (p=0.0017) (FIG. 7e). This difference was lost when SC were plated with GR127935 (p=0.4) (FIG. 7e). The faster exit of quiescence and higher division rates were also lost when adding GR127935 in vitro (FIGS. 7f,g). The effects of the plasma from fluoxetine-treated animals were persistent when adding MDL100907 (FIGS. 7b-g). Importantly, in vitro, the direct addition of a 5-HT1B agonist in the culture media triggered the same effect as the addition of plasma from fluoxetine-treated mice (FIG. 7 h,i); we observed faster differentiation at early time points post plating and a higher rate of self-renewal at later time points post plating.

The same results were obtained when primary human myoblasts were plated in plasma from fluoxetine-treated mice, with a faster differentiation 4 days post-plating (p=0.05) (FIG. 7j) and a higher self-renewal of the cells 14 days post-plating (p=0.02) (FIG. 7k). Those effects were lost when antagonising 5-HT1 BR but not 5-HT2 BR (FIG. 7j,k).

2.1.4. Fluoxetine Improves the Mdx Phenotype

Fluoxetine was delivered P.O. for 6 weeks to Mdx mice (Bulfield G et al., 1983), a Duchenne muscular dystrophy mouse model. The fluoxetine treated Mdx mice exhibited less foci of necrotic fiber (2893±803 mm$^2$ in average) compared with non-treated Mdx control (5041±1629 mm$^2$ in average, p=0.04) (FIG. 8a). The fiber size was also overall bigger in Mdx treated-animals (4.241±0.9 pixels in treated vs. 3.192±0.3 in placebo p=0.051) (FIG. 8b). Accordingly, the number of regenerating foci decreased in the Mdx mice treated with fluoxetine (FIG. 8c-d). The number of vessels increased in the treated mice (1459±327 vessels per mm$^2$) when compared to the placebo (942.4±113 vessels per section, p=0.008) (FIG. 8e). Interestingly the number of cycling satellite cells also decreased, correlating with the decreased number of regenerative foci previously observed (FIG. 8f). The treated mice also displayed a lower level of cytokines (34.52±21 pg/ml of IL6, Table 4) compared with placebo (580±158 pg/ml of IL6, p=0.004) (FIG. 8g, Table 4). The same decrease was observed for other pro-inflammatory cytokines (data not shown). Of note, the level of IL10 (an anti-inflammatory cytokine) did not change in the treated animals (99.6±56 pg/ml of MO) compared with placebo (64.1±50, p=0.4) (FIG. 8h, Table 4). This observation is in line with the decreased infiltration of inflammatory cells observed in the muscle (9.6±3.7 Gr1+ cells observed per section in the placebo vs. 4±2.4 Gr1+ cells in the treated mice p=0.04) (FIG. 8i). Notably, when Mdx mice were treated with fluoxetine and a 5-HT1B inhibitor, the beneficial effects were lost (FIG. 9a-h).

At the functional level the total muscle force of fluoxetine treated mdx mice was increased by 56% (FIG. 9I) and isolated single fibers of the extensor digitorum longus (edl) force was also increased by 45% (FIG. 9J-K). This was confirmed on soleus muscle (data not shown).

TABLE 4

Fluoxetine decreases the levels of cytokines in a dystrophin mouse model Mdx. The table represents the plasmatic levels of cytokines in picograms per µl of plasma measured by Luminex ® assay in the placebo and fluoxetine treated Mdx mice.

| Cytokine | Quantity in Placebo Mdx (pg/µm) | Quantity in Fluoxetine Mdxl treated (pg/µm) | Statistically significant | P value |
| --- | --- | --- | --- | --- |
| IL-1a | 119.8 ± 54 | 28.8 ± 10.6 | *** | 0.0006 |
| IL-1b | 1174 ± 252 | 436 ± 86 | *** | 0.0006 |
| IL-2 | 50.11 ± 27 | 22.02 ± 15.13 | * | 0.04 |
| IL-3 | 63.8 ± 14 | 21.4 ± 23.7 | * | 0.01 |
| IL-4 | 56.46 ± 94 | 29.5 ± 27.3 | ns | 0.9 |
| IL-5 | 101.6 ± 101.8 | 10.59 ± 5.5 | *** | 0.0006 |
| IL-6 | 324 ± 343 | 12.9 ± 10.24 | ** | 0.0012 |
| IL-10 | 407.9 ± 167 | 176.5 ± 96 | ns | 0.06 |
| IL-12(p40) | 2015 ± 874 | 922 ± 414 | ** | 0.007 |
| IL-12(p70) | 2557 ± 839 | 182 ± 90 | ** | 0.002 |
| IL-13 | 1942 ± 459 | 1065 ± 380 | ** | 0.007 |
| IL-17 | 91.6 ± 39 | 21.2 ± 21 | ** | 0.001 |
| Eotaxin | 2398 ± 521 | 850.4 ± 565 | ** | 0.002 |
| G-CSF | 1369 ± 880 | 65.20 ± 43.6 | *** | 0.0006 |
| GM-CSF | 1272 ± 284 | 447 ± 199 | ** | 0.002 |
| IFN-g | 428.3 ± 193 | 24.7 ± 16 | *** | 0.0006 |
| KC | 2606 ± 898 | 30.68 ± 10.2 | *** | 0.0006 |
| MCP-1 | 2704 ± 522 | 339 ± 172 | *** | 0.0006 |
| MIP-1a | 415 ± 175 | 75.5 ± 12.6 | *** | 0.0006 |
| MIP-1b | 1978 ± 1219 | 91.48 ± 84 | *** | 0.0006 |
| RANTES | 223.3 ± 151 | 19.15 ± 6.3 | *** | 0.0006 |
| TNF-a | 9927 ± 1702 | 2355 ± 782 | *** | 0.0006 |
| FGF-basic | 139 ± 37 | 118.2 ± 85 | ns | 0.25 |
| MIG | 4320 ± 3003 | 1649 ± 624 | * | 0.01 |
| PDGF | 2005 ± 721 | 2984 ± 1573 | ns | 0.25 |
| VEGF | 88.2 ± 18.9 | 32.1 ± 22.3 | ** | 0.0041 |

The p value is calculated using Mann-Whitney test.
n = 7 animals used per condition.
* $p \leq 0.05$;
** $p \leq 0.01$;
*** $p \leq 0.001$;
ns: non-statistically significant.

2.2. Vortioxetine
2.2.1. Vortioxetine Increases Vessel Number in the Tibialis Anterior In order to investigate the effect of vortioxetine on vessels number, intra peritoneal (I.P) administration of 20 mg/kg of vortioxetine was performed for either 12 days, 3 or 6 weeks to C57Bl/6 mice (FIG. 10a). The number of CD31+ cells was counted by immunostaining. The number of vessels in the placebo is (863.5±115.6 vessels per mm$^2$) and increases after 12 days of I.P treatment (2274±926 vessels per mm$^2$, p=0.03), and even more after 3 weeks (2847±705 vessels per mm$^2$, p=0.02) (FIG. 10b). However, there was no statistically significant differences between 12 days and 3 weeks of treatment (p=0.49). Neovessels display a normal histological appearance associated with a basal lamina and a permeable lumen sometimes containing red blood cells. The daily administration of vortioxetine IP might cause unwanted peritoneal inflammation that could interfere with angiogenesis since inflammation and neovascularization are intertwined in some models. Vortioxetine was therefore administered per os (P.O) for 12 days: a similar increase in the number of vessels was observed (2451±595 vessels per mm$^2$ p=0.028, FIG. 10c). To further confirm those results, vortioxetine will be administered to Flk1$^{GFP/+}$ mice P.O and I.P for 12 days, and an ex vivo Matrigel angiogenesis assay and plasma from vortioxetine treated mice will be used on HUVEC (endothelial cells).

2.2.2. Vortioxetine Increases the Number of Satellite Cells

In order to count the number of satellite cells, the tibialis anterior (TA) of Tg:Pax7nGFP mice were digested and analysed by FACS in placebo and vortioxetine (12 days, 20 mg/Kg) treated mice. Cells were then counted by cytometry (FIG. 10d) per TA and a clear increase in SC number was observed in treated (8660 satellite cells±699) vs. non-treated (4444 satellite cells±802 p=0.008) mice (FIG. 10a). These data were confirmed by histological count on sections, where a two-fold increase was found on TA sections. After 3 weeks of vortioxetine treatment, the number of satellite cells was even higher (9351 satellite cells±706, p=0.0079) but no statistically significant differences were found between 12 days and 3 weeks of treatment (p=0.15). Vortioxetine was also administered P.O at 20 mg/kg: a similar increase in SC number has been observed, thereby confirming the I.P results (FIGS. 10d,e).

2.2.3. Vortioxetine Increases the Number of Vessels and Satellite Cells Via the Stimulation of the 5-HT1 B Receptor To investigate the role of the 5-HT1 BR, GR127935 hydrochloride inhibitor, a specific 5-HT1 BR antagonist, was delivered in osmotic pump together with vortioxetine treatment I.P for 12 days. The number of vessels was lower in vortioxetine and inhibitor treated Flk1$^{GFP/+}$ mice (928±207 vessels per mm$^2$) compared with vortioxetine and PBS treated Flk1$^{GFP/+}$ mice (2274±926 vessels per mm$^2$, p=0.028 (FIG. 11a). The number of SC was also lower in vortioxetine and inhibitor treated Tg:Pax7nGFP mice (5540±411 SC per TA) compared to vortioxetine only (FIG. 11b). No inhibition of vortioxetine effects was observed when antagonizing it with MDL100907, an inhibitor of the 5-HT2 B receptor (FIGS. 11a,b), neither for the vessels nor the SC number.

After injury, the inhibition of 5-HT1 BR by GR127935 repressed the beneficial effects of the vortioxetine 12 days-treatment: indeed, one could observe a lower number of SC and differentiating cells, a lower fiber size and higher calcium deposits 14 days post-injury, a higher percentage of fibrosis as well as a higher infiltration of immune Gr1 and F4/80 cells.

Those results were confirmed in vitro as shown in FIGS. 11c-e. Satellite cells were isolated from Tg:Pax7nGFP mice and cells were plated at 2.000 cells per cm$^2$. After overnight, vortioxetine was added at 10 µM. The number of Pax7 positive cells decreased faster 4 days post-plating (23%±2 in vortioxetine treated vs. 38.25%±6 in PBS p=0.02) (FIG. 11c) and was close to the control (PBS) when incubated with the GR127935 inhibitor (25.5%±4.2 p=0.32) (FIG. 11c). 14 days post-plating, a higher number of reserve cells (Pax7 positive cells that are quiescent in vitro) were detected in the vortioxetine-treated cells (9%±0.7) than in the PBS (3.5%±0.9, p=0.01), and when GR127935 inhibitor was added in vitro the number of reserve cells dropped (3.5%±0.9, p=0.9) (FIG. 11c). The expression of MyoD (an activation marker) did not differ at any time investigated in the 3 tested conditions (FIG. 11d). However, Myogenin (MyoG), a differentiation marker displayed a 2 times increase in expression, 4 days post-plating with vortioxetine (p=0.0017) (FIG. 11e). This difference in expression was lost when SC were plated with the GR127935 5-HT1 BR inhibitor (p=0.4) (FIGS. 11c-e). The positive effects of vortioxetine were lost when GR127935 was added in vitro together with vortioxetine (FIGS. 11c-e). These effects were however persistent when adding the 5-HT2 BR antagonist (FIGS. 11c-e). This means that the positive effects observed when plating vortioxetine in vitro with satellite cells is mediated via the 5HT1B receptor and not 5HT2B.

These in vitro experiments clearly demonstrate that, similarly to the observations made in vivo, vortioxetine directly acts on satellite cells and stimulate their differentiation, at a faster regeneration rate than fluoxetine. Most importantly, an increase in the number of self-renewing satellite cells is observed after 14 days in vitro, which highlights the capacity of vortioxetine to increase the pool of muscle stem cells.

2.3. Vortioxetine Derivatives 2.3.1. Histidine-Vortioxetine and Pyrrolidinium-Vortioxetine Increases the Number of Vessels and Satellite Cells To test whether, 2 derivatives of vortioxetine, namely histidine-vortioxetine and pyrrolidinium-vortioxetine, could have similar or improved effect compared to the unmodified vortioxetine, the in vitro approach as described in section 2.2.3 above was used and the differentiation cascade of satellite cells was investigated by assessing the expression pattern of Pax7 (a marker of stemness and quiescence) and Myogenin (MyoG, a marker of differentiation) as described above in section 2.2.3. To do so, satellite cells from Tg:Pax7-nGFP were isolated by FACS and plated at 2.000 cells per $cm^2$ (seeded overnight). The following day, the vortioxetine, its derivatives, or the control PBS was added at 10 μM and the cells were fixed at the indicated time points.

The differentiation rate of the cells was faster with vortioxetine, pyrrolidinium-vortioxetine and histidine-vortioxetine than with PBS (control). Indeed, after 4 days in PBS 38.2±6.7% of cells were still Pax7+, against 23.7±2.78% when cells were plated with vortioxetine (p≤0.001), 25.25±4% with pyrrolidinium-vortioxetine (p≤0.001) and 22.5±3.3% with histidine-vortioxetine (p≤0.0001) (FIG. 12a). The Myogenin staining data further confirmed this observation with 13.25±2% of cells MyoG+ in the PBS control against 34.5±2.5% with vortioxetine (p≤0.0001), 19.75±0.47% with pyrrolidinium-vortioxetine (p≤0.05) and 30±1.7% with histidine-vortioxetine (p≤0.0001) (FIG. 12b).

Taken together, these results demonstrate that, in vitro, the pyrrolidinium-vortioxetine and histidine-vortioxetine trigger a fast differentiation of satellite cells similar to vortioxetine.

Importantly, when assessing the self-renewal of satellite cells, it was observed that both pyrrolidinium-vortioxetine and histidine-vortioxetine displayed more Pax7+ cells 14 days post-plating (with medium changed every 4 days). Indeed, at the end of the differentiation process in vitro, 2±0.4% of cells were Pax7+ with PBS against 10.5±0.65% with vortioxetine, 12.5±1.9% with pyrrolidinium-vortioxetine (0.0.01), and 12.25±1.3% with histidine-vortioxetine (p≤0.05). This indicates that the number of self-renewing cells in vitro is higher with pyrrolidinium-vortioxetine and histidine-vortioxetine when compared with vortioxetine alone (FIGS. 12a,b; 20% increase). 20 mg/Kg Histidine-vortioxetine or Pyrrolidinium-vortioxetine was injected IP for 12 days in TgPax7nGFP mice: a doubling in the number of SCs was observed in the TA. These results indicates that those 2 derivatives have the same effect compared with vortioxetine (FIG. 12c,d).

3. Discussion

Antidepressant drugs of the selective serotonin reuptake inhibitor (SSRI) class (e.g., fluoxetine) are commonly used to treat a wide spectrum of mood disorders (Marsella et al., 1975). Interestingly, the use of fluoxetine to improve regeneration of other organs than brain has never been assessed.

The present results show that the administration of not only fluoxetine, but also of vortioxetine (a well-known atypical antidepressant), increased the number of vessels and, most importantly, of satellite cells in skeletal muscle. These results were confirmed using different approaches (genetics and immunostaining), routes of administration (intraperitoneal and per os) and different concentrations. These data were further confirmed ex vivo with more vessels invading the Matrigel plugs in fluoxetine treated mice. In vitro, the human endothelial cells HUVEC displayed more divisions when plated in plasma of mice treated with fluoxetine, when compared with plasma coming from placebo treated mice. Primary human satellite cells also displayed differentiation at early time points and higher self-renewal potential at late time points post-plating.

Crucially, fluoxetine or vortioxetine treated animals displayed a faster regeneration when injured, and this was sustainable through multiple rounds of injury. The faster regeneration was assessed both at the genetic (Myogenin expression) and histological level. Besides, the regeneration was faster with vortioxetine compared to fluoxetine (2 weeks instead of 6 weeks). When looking for the mechanism of action that could be involved in this improved regeneration, the speed of activation did not seem to bet involved, as MyoD was detected at the same time points both in vivo and in vitro in the treated and control mice. Instead, the initial number of satellite cells was almost doubled in vivo. In vitro, the satellite cells displayed more cell divisions and a faster differentiation when plated in fluoxetine treated mice plasma.

When assessing the self-renewal of satellite cells, it was further observed that both pyrrolidinium-vortioxetine and histidine-vortioxetine displayed better effect in vitro than vortioxetine alone 14 days post-plating. At early time points post-plating (4 days), it was observed that both pyrrolidinium-vortioxetine and histidine-vortioxetine displayed faster differentiation.

It is also shown that the delivery of fluoxetine or vortioxetine was triggering an exit of quiescence of the satellite cells. Indeed, more cells were detected after 6 weeks treatment and as these were BrdU+, it meant that those extra cells come from division of the existing cells (self-renewal). This could be at the root of the faster regeneration of muscle after an injury. Indeed, it is possible that the higher number of satellite cells explains the faster differentiation however their faster activation and division rate upon injury in vitro is more likely to explain the faster differentiation. This could mean that satellite cells, although quiescent, exit their dormant state and activate faster upon injury or when in need of activation.

The in vivo and in vitro data displayed herein are thus showing a 2 steps mode of action that could have different mechanisms depending on the cellular, physiological or pathological state. When dormant, the satellite cells could be activated by fluoxetine or vortioxetine or any 5-HT1B stimulation that would trigger their self-renewal in a controlled and limited manner. After the cellular activation, at one point in the cascade of differentiation the 5-HT1BR activation could trigger faster differentiation (either because the cell density is higher, or because, as showed, the direct activation of the 5-HT1B receptor triggers differentiation (not exclusive hypothesis)). Thus, the 5-HT1BR stimulation triggers exit of dormancy of satellite cells and increases cell rate division, self-renewal in normal physiological conditions but also differentiation when needed.

Delivery of fluoxetine also increased the levels serotonin receptors 5-HT1 BR by 90 fold in the endothelial and SC cells, and pharmaceutical delivery of 5-HT1 BR inhibitor cancelled the effects of fluoxetine, both on the increase of vessels and satellite cells number. In vitro, the fluoxetine increased the speed of differentiation and the number of reserve cells, while the addition of the inhibitor canceled those effects. This is a key point, as it shows that fluoxetine, or metabolites found in plasma generated in vivo by fluoxetine administration, can directly act on the SC by targeting the 5-HT1 B receptor.

The inhibition of 5-HT2 BR did not affect the results, indicating that the effect of fluoxetine from plasma treated mice or directly mediated by vortioxetine acts specifically on the 5-HT1 B receptor.

Duchenne muscular dystrophy (DMD) is the most common muscular dystrophy and an X-linked recessive, progressive muscle wasting disease caused by the absence of a functional dystrophin protein (Emery, 2002). The structural defects seen in DMD render myocytes with an increased susceptibility to mechanical stress, and together with important ischemia, it generates myocyte damage, which induces successive rounds of myofiber degeneration and regeneration, loss of calcium homeostasis, chronic inflammatory response, fibrosis, and myonecrosis. In individuals with DMD, these processes inevitably cause loss of ambulation shortly after the first decade and an abbreviated life with death in the third or fourth decade due to cardio-respiratory anomalies. There is no known cure for DMD, and although the culpable gene has been identified for more than twenty years, research on treatments has produced few clinically relevant results. Due to these characteristics targeting both vessels (ischemia) and satellite cells (muscle regeneration) could be of main interest.

After delivery of fluoxetine to dystrophic mice (Mdx), great variations in the muscle fiber size and centronucleated fibers were still observed but the number of necrotic foci dramatically decreased and the overall diameter of fibers was higher. By Luminex® assay, it was also showed that the global levels of cytokines, a well-known readout of inflammation in Mdx mouse, decreased. This was associated with a diminution of the number of infiltrated inflammatory cells.

Taken together, those results indicate that the delivery of fluoxetine, vortioxetine, or derivatives thereof, to dystrophic patients has the potential to decrease the progression of the dystrophy, by increasing muscle regeneration, more particularly the number of muscle stem cells (in addition to vessels). The present data show that this effect is directly mediated via the 5-HT1 B receptor which is expressed both on endothelial cells and muscle stem cells.

REFERENCES

Baroffio A, Hamann M et al. (1996). *Differentiation;* 60(1): 47-57.

Bauer J M, Kaiser M J, and Sieber C C (2008). *J Am Med Dir Assoc;* 9(8):545-51

Baumgartner R N, Koehler K M, Gallagher D, et al (1998). *Am. J. Epidemiol.;* 147 (8): 755-63

Beauchamp J R, Heslop L et al. (2000). *J Cell Biol;* 151(6): 1221-34.

Bentzinger C F, and Rudnicki M A (2014). *Nat Med.;* 20(3):234-5.

Bernet J D, Doles J D, Hall J K, Kelly Tanaka K, Carter T A, and Olwin B B (2014). *Nat Med.;* 20(3):265-71.

Bischoff R (1994). *Myology* (eds A. G. Engel and C. Frazini-Armstrong), pp. 97-118. McGraw-Hill, New York.

Bulfield G, Siller W G, Wight P A, and Moore K J (1984). *Proc Natl Acad Sci USA;* 81:1189-92.

Charge S B and Rudnicki M A (2004). *Physiol Rev;* 84(1): 209-38.

Cornelison D D and Wold B J (1997). *Dev Biol;* 191(2): 270-83.

Cosgrove B D, Gilbert P M, Porpiglia E, Mourkioti F, Lee S P, Corbel S Y, Llewellyn M E, Delp S L, and Blau H M (2014). *Nat Med.;* 20(3):255-64.

Emery A E (2002). *Lancet;* 359: 687-695.

Farmaco, 1989, 44, from p. 683.

Goodell M A, and Rando T A (2015). *Science;* 350(6265): 1199-204.

Grounds M D and Yablonka-Reuveni Z (1993). *Cell Biol Hum Dis Ser,* 3:210-256.

Hawke T J and Garry D J (2001). *J Appl Physiol;* 91:534: 551.

Jin H, Oksenberg D, Ashkenazi A, Peroutka S J, Duncan A M, Rozmahel R, Yang Y, Mengod G, Palacios J M, O'Dowd B F (1992). *J. Biol. Chem;* 267 (9): 5735-8.

Kelly R, Alonso S, Tajbakhsh S, Cossu G, Buckingham M (1995). *J Cell Biol.;* 129(2):383-96.

Kuang S, Kuroda K et al. (2007). *Cell;* 129(5): 999-1010.

Kuch C, Winnekendonk D et al. (1997). *Exp Cell Res;* 232(2): 331-8.

Kudryashova E, Kramerova I, and Spencer M J (2012). *J Clin Invest.;* 122(5):1764-76.

Kuroda N, Ohyama Y, Nakashima K, Nakashima K, and Akiyama S (1996). Chemical and Pharmaceutical Bulletin; 44(8): 1525-1529.

Kwak K B, Chung S S et al. (1993). *Biochim Biophys Acta;* 1175(3): 243-9.

Lepper C, Partridge T A & Fan C M (2001). *Development;* 138: 3639-3646.

Livak K J and Schmittgen T D (2001). *Methods* 25(4): 402-8.

Marsella A J, Sanborn K O, Kameoka V, Shizuru L & Brennan J (1975). *J Clin Psychol;* 31: 281-287.

Messier V, Karelis A D, Lavoie M E, Brochu M, Faraj M, Strychar I, and Rabasa-Lhoret R (2009). *Appl Physiol Nutr Metab.;* 34(1): 18-24.

Moss F O and Leblond C P (1971). *Anat. Rec.;* 170:421-435.

Mokrosz J L, Pietrasiewicz M, Duszynska B, and Cegla M (1992). *J. Med. Chem.;* 35 (13): 2369-2374.

Murphy M M, Lawson J A, Mathew S J, Hutcheson D A & Kardon G (2011). *Development;* 138: 3625-3637.

Nakaya K, Tanaka T, Shirataki Y, Shiozaki H, Funabiki K, Shibata K, Matsui M (2001). *Bulletin of the Chemical Society of Japan.;* 74(1): 173-177.

Rocheteau P, Gayraud-Morel B, Siegl-Cachedenier I, Blasco M A, Tajbakhsh S (2012). *Cell;* 148(1-2):112-25.

Romanelli M N, Manetti D, Scapecchi S, Borea P A, Dei S, Bartolini A, Ghelardini C, Gualtieri F, Guandalini L, and Varani K (2001). *J Med Chem.;* 44(23):3946-55.

Sadat U, Jaffer F A, Van Zandvoort MAMJ, Nicholls S J, Ribatti D and Gillard J H (2014). *Circulation;* 130:786-794.

Sambasivan R et al. (2009). *Dev Cell;* 16, 810-821.

Sambasivan R et al. (2011). *Development;* 138: 3647-3656 (2011).

Sanchez F M, Cuadra G I, Nielsen S J, Tanner A, Berges B K (2013). *Methods Mol Biol;* 1031:19-26.

Shi X and Garry D J (2006). *Genes & Development;* 20:1692-1708.

Schmuck K, Ullmer C, Engels P, Lübbert H (1994). *FEBS Lett;* 342(1):85-90.

Schulz E and Jaryszak D L (1985). *Mech. Ageing Dev.;* 30-63-72.

Smith C K, Janney M J et al. (1994). *J Cell Physiol;* 159(2): 379-85.

Smythe G M, Davies M J et al. (2001). *Cell Tissue Res;* 304(2): 287-94.

Yablonka-Reuveni Z and Rivera A J (1994). *Dev Biol;* 164(2): 588-603.

Vaittinen S, Lukka R et al. (2001). *J Neuropathol Exp Neurol;* 60(6): 588-97.

The invention claimed is:

1. A method, comprising:
contacting satellite cells with an effective amount of a direct 5-hydroxytryptamine 1B receptor (5-HT1 BR)-stimulating agent selected from a triptan, a vortioxetine, and an ergotamine, to thereby promote satellite cell proliferation by increasing division rate.

2. The method of claim 1, wherein the satellite cells are contacted in vitro.

3. The method of claim 2, wherein the satellite cells are contacted by administering an effective amount of the direct 5-hydroxytryptamine 1B receptor (5-HT1 BR)-stimulating agent to an isolated biological sample comprising satellite cells.

4. The method of claim 1, wherein the satellite cells are contacted by administering the direct 5-hydroxytryptamine 1B receptor (5-HT1 BR)-stimulating agent to a subject affected by a natural or by a pathological loss and/or damage and/or impairment of skeletal muscle tissue to thereby provide a therapeutic benefit to the subject.

5. The method of claim 4, wherein the subject has sarcopenia.

6. The method of claim 5, wherein the subject has cancer-induced sarcopenia.

7. The method of claim 1, wherein the agent is vortioxetine.

8. The method of claim 1, wherein the agent is a triptan.

9. The method of claim 8, wherein the triptan is selected from sumatriptan, rizatriptan, zolmitriptan, eletriptan, almotriptan, frovatriptan, naratriptan, avitriptan, and donitriptan.

10. The method of claim 1, wherein the agent is modified to comprise at least one positively charged chemical moiety.

11. The method of claim 10, wherein the positively charged chemical moiety is a quaternary ammonium group or a tertiary sulfonium group.

12. The method of claim 10, wherein the agent is a positively charged vortioxetine selected from the group consisting of salts of vortioxetine, vortioxetine coupled to a positively charged amino acid, pyrrolidinium-vortioxetine, pyperazinium-vortioxetine, dimethylammonium-vortioxetine, sulfonium-vortioxetine, N-oxide-vortioxetine, sulfoxide-vortioxetine, and phosphonium-vortioxetine.

13. The method of claim 10, wherein the agent is histidine-vortioxetine or pyrrolidinium-vortioxetine.

14. A method of promoting satellite cell proliferation by increasing division rate, comprising administering a pharmaceutical composition comprising at least one direct 5-hydroxytryptamine 1B receptor (5-HT1 BR)-stimulating agent selected from a triptan, a vortioxetine, and an ergotamine and at least one pharmaceutically acceptable excipient to the subject.

15. The method of claim 14, wherein the agent is vortioxetine.

16. The method of claim 14, wherein the agent is a triptan.

17. The method of claim 16, wherein the triptan is selected from sumatriptan, rizatriptan, zolmitriptan, eletriptan, almotriptan, frovatriptan, naratriptan, avitriptan, and donitriptan.

18. The method of claim 14, wherein the agent is modified to comprise at least one positively charged chemical moiety.

19. The method of claim 18, wherein the positively charged chemical moiety is a quaternary ammonium group or a tertiary sulfonium group.

20. The method of claim 18, wherein the agent is a positively charged vortioxetine selected from the group consisting of salts of vortioxetine, vortioxetine coupled to a positively charged amino acid, pyrrolidinium-vortioxetine, pyperazinium-vortioxetine, dimethylammonium-vortioxetine, sulfonium-vortioxetine, N-oxide-vortioxetine, sulfoxide-vortioxetine, and phosphonium-vortioxetine.

21. The method of claim 18, wherein the agent is histidine-vortioxetine or pyrrolidinium-vortioxetine.

22. A method of promoting muscle regeneration and/or delaying progression of at least one of natural or pathological loss, damage and impairment of skeletal muscle in a subject by increasing satellite cell division rate, comprising administering a pharmaceutical composition comprising at least one direct 5-hydroxytryptamine 1B receptor (5-HT1 BR)-stimulating agent selected from a triptan, a vortioxetine, and an ergotamine and at least one pharmaceutically acceptable excipient to the subject.

23. The method of claim 22, wherein the subject has a pathological loss of skeletal muscle tissue(s).

24. The method of claim 22, wherein the subject has a natural loss of skeletal muscle tissue(s).

25. The method of claim 22, wherein the subject has damage and/or impairment of skeletal muscle tissue(s).

26. The method of claim 22, wherein the subject has sarcopenia.

27. The method of claim 22, wherein the triptan is selected from sumatriptan, rizatriptan, zolmitriptan, eletriptan, almotriptan, frovatriptan, naratriptan, avitriptan, and donitriptan.

* * * * *